US008614296B2

(12) United States Patent
Kumar et al.

(10) Patent No.: US 8,614,296 B2
(45) Date of Patent: *Dec. 24, 2013

(54) HUMANIZED ANTIBODIES SPECIFIC FOR AMINO ACID SEQUENCE RGD OF AN EXTRACELLULAR MATRIX PROTEIN AND THE USES THEREOF

(75) Inventors: Shankar Kumar, Pleasanton, CA (US); J. Yun Tso, Menlo Park, CA (US); Naoya Tsurushita, Palo Alto, CA (US); Shigeyuki Kon, Hokkaido (JP); Toshimitsu Uede, Hokkaido (JP)

(73) Assignee: Gene Techno Science Co., Ltd., Hokkaido (JP)

( * ) Notice: Subject to any disclaimer, the term of this patent is extended or adjusted under 35 U.S.C. 154(b) by 39 days.

This patent is subject to a terminal disclaimer.

(21) Appl. No.: 12/989,208

(22) PCT Filed: Apr. 24, 2009

(86) PCT No.: PCT/JP2009/058604
§ 371 (c)(1),
(2), (4) Date: Jan. 3, 2011

(87) PCT Pub. No.: WO2009/131256
PCT Pub. Date: Oct. 29, 2009

(65) Prior Publication Data
US 2011/0091386 A1    Apr. 21, 2011

Related U.S. Application Data

(60) Provisional application No. 61/047,604, filed on Apr. 24, 2008.

(51) Int. Cl.
*C07K 16/00* (2006.01)
*C07K 16/46* (2006.01)
*C07K 16/28* (2006.01)

(52) U.S. Cl.
USPC ............... 530/387.1; 530/387.3; 530/388.22

(58) Field of Classification Search
None
See application file for complete search history.

(56) References Cited

U.S. PATENT DOCUMENTS

| 5,530,101 | A | * | 6/1996 | Queen et al. | 530/387.3 |
| 5,859,205 | A | * | 1/1999 | Adair et al. | 530/387.3 |
| 7,241,873 | B2 | * | 7/2007 | Uede et al. | 530/387.3 |
| 2004/0234524 | A1 | | 11/2004 | Uede et al. | |
| 2006/0002923 | A1 | | 1/2006 | Uede et al. | |
| 2011/0065899 | A1 | * | 3/2011 | Kon et al. | 530/387.3 |

FOREIGN PATENT DOCUMENTS

| EP | 1 375 518 A1 | 1/2004 |
| EP | 1 637 159 A1 | 3/2006 |
| WO | WO 97/11718 A1 | 4/1997 |
| WO | WO 00/63241 A2 | 10/2000 |
| WO | WO 01/71358 A1 | 9/2001 |
| WO | WO 02/081522 A1 | 10/2002 |
| WO | WO 03/027151 A1 | 4/2003 |
| WO | WO 2008/050907 A1 | 5/2008 |

OTHER PUBLICATIONS

Tsurushita et al., Design of humanized antibodies: From anti-Tac to Zenapax. Methods 36:69-83, 2005.*
Klimka et al., British Journal of Cancer (2000) 83:252-260.*
Beiboer et al., Guided selection of a pan carcinoma specific antibody reveals similar binding characteristics yet structural divergence between the original murine antibody and its human equivalent. J. Mol., Biol. (2000) 296:833-849.*
Brown et al. Tolerance of single, but not multiple, amino acid replacements in antibody VH CDR 2: a means of minimizing B cell wastage from somatic hypermutation? J. Immuno. May 1996, 3285-91.*
Paul, Fundamental Immunology, 3rd Edition, 1993, pp. 292-295.*
Eduardo Padlan, Anatomy of the antibody molecule. Mol Immunol. Feb. 1994;31(3):169-217.*
Green et al., "Antibody engineering via genetic engineering of the mouse: XenoMouse strains are a vehicle for the facile generation of therapeutic human monoclonal antibodies," Journal of Immunological Methods, 1999, 231:11-23.
Kon et al., "Mapping of Functional Epitopes of Osteopontin by Monoclonal Antibodies Raised Against Defined Internal Sequences," Journal of Cellular Biochemistry, Oct. 15, 2001, 84(2):420-432.
U.S. Appl. No. 12/312,022, filed Oct. 25, 2007, Shigeyuki et al.
Yamamoto et al,. "Successful treatment of collagen-induced arthritis in non-human primates by chimeric anti-osteopontin antibody," International Immunopharmacology, 2007, 7:1460-1470.
International Search Report and Written Opinion mailed Jul. 21, 2009, in PCT/JP2009/058604, 18 pages.
Frisch et al., "Integrins and anoikis," Curr. Opin. Cell Biol., 1997, 9:701-706.
Giancotti et al., "Integrin Signaling," Science, Aug. 13, 1999, 285:1028-1032.
Gu et al., "Laminin-10/11 and Fibronectin Differentially Regulate Integrin-dependent Rho and Rac Activation via p130$^{Ca5}$-Crkll-DOCK180 Pathway," J. Biol. Chem., Jul. 20, 2001, 276(29):27090-27097.
Gu et al., "Laminin-10/11 and Fibronectin Differentially Prevent Apoptosis Induced by Serum via Phosphatidylinositol 3-Kinase/Akt- and MEK1/ERK-dependent Pathways," J. Biol. Chem., May 31, 2002, 277(22):19922-19928.

(Continued)

Primary Examiner — Maher Haddad
(74) Attorney, Agent, or Firm — Foley & Lardner LLP

(57) ABSTRACT

The present invention provides humanized antibodies that immunospecifically recognize the RGD sequence. Some of these antibodies inhibit the biological functions of the RGD proteins, thereby exhibiting therapeutic effects on various disorders or diseases that are associated with RGD proteins, including cancer, e.g., the growth and metastasis of a cancer cell, and inflammatory diseases, e.g., rheumatoid arthritis, osteoarthritis, hepatitis, endometriosis, bronchial asthma, fibrosis, diabetes, arteriosclerosis, multiple sclerosis, granuloma, an inflammatory bowel disease (ulcerative colitis and Crohn's disease), an autoimmune disease, and so forth.

10 Claims, 41 Drawing Sheets

(56) References Cited

OTHER PUBLICATIONS

Vassilev et al., "Inhibition of Cell Adhesion by Antibodies to Arg-Gly-Asp (RGD) in Normal Immunoglobulin for Therapeutic Use (Intravenous Immunoglobulin, IVIg)," Blood, Jun. 1, 1999, 93(11):3624-3631.

Casset et al., "A peptide mimetic of an anti-CD4 monoclonal antibody by rational design," Biochemical and Biophysical Research Communications, 2003, 307:198-205.

Chen et al., "Selection and Analysis of an Optimized Anti-VEGF Antibody: Crystal Structure of an Affinity-matured Fab in Complex with Antigen," Journal of Molecular Biology, 1999, 293:865-881.

DePascalis et al., "Grafting of 'Abbreviated' Complementarity-Determining Regions Containing specificity-Determining Residues Essential for Ligand Contact to Engineer a Less Immunogenic Humanized Monoclonal Antibody," Journal of Immunology, 2002, 169:3076-3084.

Holm et al., "Functional mapping and single chain construction of the anti-cytokeratin 8 monoclonal antibody TS1," Molecular Immunology, 2007, 44:1075-1084.

MacCallum et al., "Antibody-antigen Interactions: Contact Analysis and Binding Site Topography," J. Mol. Biol., 1996, 262:732-745.

U.S. Appl. No. 13/497,692, filed Mar. 22, 2012, Kumar et al.

Rudikoff et al., "Single amino acid substitution altering antigen-binding specificity," Proc. Natl. Acad. Sci. USA, Mar. 1982, 79:1979-1983.

Vajdos et al., "Comprehensive Functional Maps of the Antigen-binding Site of an Anti-ErbB2 Antibody Obtained with Shotgun Scanning Mutagenesis," J. Mol. Biol., 2002, 320:415-428.

Wu et al., "Humanization of a Murine Monoclonal Antibody by Simultaneous Optimization of Framework and CDR Residues," J. Mol. Biol., 1999, 294:151-162.

Johnson et al., "The Kabat Database and a Bioinformatics Example," Methods in Molecular Biology, 2004, 248:11-25.

Osbourn et al., "Current methods for the generation of human antibodies for the treatment of autoimmune diseases," Drug Discovery Today, Sep. 2003, 8(18):845-851.

Almagro et al., "Humanization of antibodies," Frontiers in Bioscience, Jan. 1, 2008, 13:1619-1633.

\* cited by examiner

Fig. 6

Heavy Chain

```
                                    CDRH1                    CDRH2
33E10  1:VKLQESGGGLVQPGGSLSLSCAAS GFTFTDYYMI- WVRQPPGKALE WLGFIRNKANGYTTE :60
35B6   1:VKLQESGTELVKPGASVKLSCKAS GYTFTNYWMH- WVKQRPGQGLE WIGNINPRN-GDSN- :59

33E10 61:YSASVKG RFTISRDNSQSILYLQMNALRAEDSATYYCAR G-A-----Y- WGQGTTVTVSS :113
35B6  60:YNEKFRS KASLTVDKSSSTVYMQLSSLTSEDSAVYYCAR --G---YFDV WGQGTTVTVSS :113
                                                    CDRH3
```

Fig. 7

Light Chain

```
                        CDRL1                              CDRL2
33E10  1: DVLMTQTPLSLPVSLGDQASISC RSSQSIVHSNGNTYLE WYLQKPGQSPKLLIY RVSNRF :60
35B6   1: DIQMTQSPSSMYASLGERVSITC KASQDIN-----SYLS WFQQKSGKSPKTLIY RAN-RL :54

33E10 61: S- GVPDRFSGSGSGTDFTLKISRVEAEDLGVYYCF QGSFVPW TFGGGTKLEIKR:113
35B6  55: VD GVPSRFSGSGSGQDFSLTISSLEYEDMGIYYCL QYDEFPH TFGSGTKLEIKR:108
                                             CDRL3
```

Fig. 15

```
ATGAAGTTGTGGCTGAACTGGATTTTCCTTGTAACACTTTTAAATGGTTTCCAGTGTGAG
 M  K  L  W  L  N  W  I  F  L  V  T  L  L  N  G  F  Q  C  E

GTGAAGCTGGTGGAGTCTGGAGGAGGCTTGGTACAGCCTGGGGGTTCTCTGAGTCTCTCC
 V  K  L  V  E  S  G  G  G  L  V  Q  P  G  G  S  L  S  L  S

TGTGCAGCTTCTGGATTCACCTTCACTGATTACTACATGATCTGGGTCCGCCAGCCTCCA
 C  A  A  S  G  F  T  F  T  D  Y  Y  M  I  W  V  R  Q  P  P

GGGAAGGCACTTGAGTGGTTGGGTTTTATTAGAAACAAAGCTAATGGTTACACAACAGAG
 G  K  A  L  E  W  L  G  F  I  R  N  K  A  N  G  Y  T  T  E

TACAGTGCATCTGTGAAGGGTCGGTTCACCATCTCCAGAGATAATTCCCAAAGCATCCTC
 Y  S  A  S  V  K  G  R  F  T  I  S  R  D  N  S  Q  S  I  L

TATCTTCAAATGAATGCCCTGAGAGCTGAGGACAGTGCCACTTATTACTGTGCAAGGGGG
 Y  L  Q  M  N  A  L  R  A  E  D  S  A  T  Y  Y  C  A  R  G

GCTTACTGGGGCCAAGGGACTCTGGTCACTGTCTCTGCA
 A  Y  W  G  Q  G  T  L  V  T  V  S  A
```

Fig. 16

```
ATGAAGTTGCCTGTTAGGCTGTTGGTGCTGATGTTCTGGATTCCTGCTTCCAGCAGTGAT
 M   K   L   P   V   R   L   L   V   L   M   F   W   I   P   A   S   S   S   D

GTTTTGATGACCCAAACTCCACTCTCCCTGCCTGTCAGTCTTGGAGATCAAGCCTCCATC
 V   L   M   T   Q   T   P   L   S   L   P   V   S   L   G   D   Q   A   S   I

TCTTGCAGATCTAGTCAGAGCATTGTACATAGTAATGGAAACACCTATTTAGAATGGTAC
 S   C   R   S   S   Q   S   I   V   H   S   N   G   N   T   Y   L   E   W   Y

CTGCAGAAACCAGGCCAGTCTCCAAAGCTCCTGATCTACAGAGTTTCCAACCGATTTTCT
 L   Q   K   P   G   Q   S   P   K   L   L   I   Y   R   V   S   N   R   F   S

GGGGTCCCAGACAGGTTCAGTGGCAGTGGATCAGGGACAGATTTCACACTCAAGATCAGC
 G   V   P   D   R   F   S   G   S   G   S   G   T   D   F   T   L   K   I   S

AGAGTGGAGGCTGAGGATCTGGGAGTTTATTACTGCTTTCAAGGTTCATTTGTTCCGTGG
 R   V   E   A   E   D   L   G   V   Y   Y   C   F   Q   G   S   F   V   P   W

ACGTTCGGTGGAGGCACCAAGCTGGAAATCAAA
 T   F   G   G   G   T   K   L   E   I   K
```

Fig. 17

```
SpeI
ACTAGTACCACCATGAAGTTGTGGCTGAACTGGATTTTCCTTGTAACACTTTTAAATGGT
         M   K   L   W   L   N   W   I   F   L   V   T   L   L   N   G

TTCCAGTGTGAGGTGAAGCTGGTGGAGTCTGGAGGAGGCTTGGTACAGCCTGGGGGTTCT
 F   Q   C   E   V   K   L   V   E   S   G   G   G   L   V   Q   P   G   G   S

CTGAGTCTCTCCTGTGCAGCTTCTGGATTCACCTTCACTGATTACTACATGATCTGGGTC
 L   S   L   S   C   A   A   S   G   F   T   F   T   D   Y   Y   M   I   W   V

CGCCAGCCTCCAGGGAAGGCACTTGAGTGGTTGGGTTTTATTAGAAACAAAGCTAATGGT
 R   Q   P   P   G   K   A   L   E   W   L   G   F   I   R   N   K   A   N   G

TACACAACAGAGTACAGTGCATCTGTGAAGGGTCGGTTCACCATCTCCAGAGATAATTCC
 Y   T   T   E   Y   S   A   S   V   K   G   R   F   T   I   S   R   D   N   S

CAAAGCATCCTCTATCTTCAAATGAATGCCCTGAGAGCTGAGGACAGTGCCACTTATTAC
 Q   S   I   L   Y   L   Q   M   N   A   L   R   A   E   D   S   A   T   Y   Y

TGTGCAAGGGGGGCTTACTGGGGCCAAGGGACTCTGGTCACTGTCTCTGCAGGTGAGTCC
 C   A   R   G   A   Y   W   G   Q   G   T   L   V   T   V   S   A

HindIII
TAACTTCAAGCTT
```

Fig. 18

```
NheIGCTAGCACCACCATGAAGTTGCCTGTTAGGCTGTTGGTGCTGATGTTCTGGATTCCTGCT
        M  K  L  P  V  R  L  L  V  L  M  F  W  I  P  A

TCCAGCAGTGATGTTTTGATGACCCAAACTCCACTCTCCCTGCCTGTCAGTCTTGGAGAT
 S  S  S  D  V  L  M  T  Q  T  P  L  S  L  P  V  S  L  G  D

CAAGCCTCCATCTCTTGCAGATCTAGTCAGAGCATTGTACATAGTAATGGAAACACCTAT
 Q  A  S  I  S  C  R  S  S  Q  S  I  V  H  S  N  G  N  T  Y

TTAGAATGGTACCTGCAGAAACCAGGCCAGTCTCCAAAGCTCCTGATCTACAGAGTTTCC
 L  E  W  Y  L  Q  K  P  G  Q  S  P  K  L  L  I  Y  R  V  S

AACCGATTTTCTGGGGTCCCAGACAGGTTCAGTGGCAGTGGATCAGGGACAGATTTCACA
 N  R  F  S  G  V  P  D  R  F  S  G  S  G  S  G  T  D  F  T

CTCAAGATCAGCAGAGTGGAGGCTGAGGATCTGGGAGTTTATTACTGCTTTCAAGGTTCA
 L  K  I  S  R  V  E  A  E  D  L  G  V  Y  Y  C  F  Q  G  S

TTTGTTCCGTGGACGTTCGGTGGAGGCACCAAGCTGGAAATCAAACGTAAGTAGAATCCA
 F  V  P  W  T  F  G  G  G  T  K  L  E  I  K

EcoRI
AAGAATTC
```

Fig. 20

```
                      1          2          3          4
            123456789 0123456789 0123456789 0123456789 0123456789
33E10       EVKLVESGG GLVQPGGSLS LSCAASGFTF TDYYMIWVRQ PPGKALEWLG
Hu33E10     EVQLVESGG GLVQPGGSLR LSCAASGFTF TDYYMIWVRQ APGKGLEWLG
U03400      EVQLVESGG GLVQPGGSLR LSCAASGFTF S-----WVRQ APGKGLEWVG 5               6          7           8
            0122223456789 0123456789 0123456789 0122223456789
                 abc                                  abc
33E10       FIRNKANGYTTEY SASVKGRFTI SRDNSQSILY LQMNALRAEDSAT
Hu33E10     ------------- ------RFTI SRDNAKNSLY LQMNSLRAEDTAV
U03400      ------------- ------RFTI SRDNAKNSLY LQMNSLRAEDTAV 1          1
                 9      0          1
            0123456789 0123456789 0123
33E10       YYCARG---- -AYWGQGTLV TVSA
Hu33E10     YYCARG---- -AYWGQGTMV TVSS
U03400      YYCAR----- ---WGQGTMV TVSS
```

Fig. 21

```
                        1          2               3
               123456789 0123456789 012345677777789 0123456789
                                         abcde
33E10          DVLMTQTPL SLPVSLGDQA SISCRSSQSIVHSNG NTYLEWYLQK
Hu33E10        DIVMTQSPL SLPVTPGEPA SISCRSSQSIVHSNG NTYLEWYLQK
X72452 DIVMTQSPL SLPVTPGEPA SISC----------- -----WYLQK 4          5          6          7
               0123456789 0123456789 0123456789 0123456789
33E10          PGQSPKLLIY RVSNRFSGVP DRFSGSGSGT DFTLKISRVE
Hu33E10        PGQSPQLLIY RVSNRFSGVP DRFSGSGSGT DFTLKISRVE
X72452 PGQSPQLLIY -------GVP DRFSGSGSGT DFTLKISRVE 1
                   8          9         0
               0123456789 0123456789 01234567
33E10          AEDLGVYYCF QGSFVPWTFG GGTKLEIK
Hu33E10        AEDVGVYYCF QGSFVPWTFG QGTKVEIK
X72452 AEDVGVYYC- --------FG QGTKVEIK
```

Fig. 22

```
JNJ220    GGGACTAGTACCACCATGAAG
JNJ206    GGGACTAGTACCACCATGAAGTTGTGGCTGAACTGGATTTTCCTTGTAACACTT
JNJ207    CAGCTGCACTTCACACTGGAAACCATTTAAAAGTGTTACAAGGAAAATCCA
JNJ208    TTCCAGTGTGAAGTGCAGCTGGTGGAGTCTGGAGGAGGCTTGGTACAGCCT
JNJ209    AGCTGCACAGGAGAGTCTCAGAGAACCCCCAGGCTGTACCAAGCCTCCTCC
JNJ210    CTGAGACTCTCCTGTGCAGCTTCTGGATTCACCTTCACTGATTACTACATG
JNJ211    TCCCTTCCCTGGAGCCTGGCGGACCCAGATCATGTAGTAATCAGTGAAGGT
JNJ212    CGCCAGGCTCCAGGGAAGGGACTTGAGTGGTTGGGTTTTATTAGAAACAAA
JNJ213    TGCACTGTACTCTGTTGTGTAACCATTAGCTTTGTTTCTAATAAAACCCAA
JNJ214    TACACAACAGAGTACAGTGCATCTGTGAAGGGTCGGTTCACCATCTCCAGA
JNJ215    TTGAAGATAGAGTGAGTTCTTGGCATTATCTCTGGAGATGGTGAACCGACC
JNJ216    AAGAACTCACTCTATCTTCAAATGAACTCCCTGAGAGCTGAGGACACGGCC
JNJ217    CCAGTAAGCGCCCCTTGCACAGTAATACACGGCCGTGTCCTCAGCTCTCAG
JNJ218    TGTGCAAGGGGCGCTTACTGGGGCCAAGGGACTATGGTCACTGTCTCTTCA
JNJ219    GGGAAGCTTGGAAAGCCCATCTTACCTGAAGAGACAGTGACCATAGT
JNJ221    GGGAAGCTTGGAAAGCCCATC
```

Fig. 23

```
JNJ116    GGGCTAGCACCACCATGAGG
JNJ193    GGGCTAGCACCACCATGAGGACCCCTGCTCAGTTTCTTGGAATCTTGTTGCTC
JNJ194    CACAATATCACATTTGATACCTGGAAACCAGAGCAACAAGATTCCAAGAAA
JNJ195    GGTATCAAATGTGATATTGTGATGACCCAATCTCCACTCTCCCTGCCTGTC
JNJ196    GCAAGAGATGGAGGCTGGCTCTCCAGGAGTGACAGGCAGGGAGAGTGGAGA
JNJ197    GAGCCAGCCTCCATCTCTTGCAGATCTAGTCAGAGCATTGTACATAGTAAT
JNJ198    CTGCAGGTACCATTCTAAATAGGTGTTTCCATTACTATGTACAATGCTCTG
JNJ199    TATTTAGAATGGTACCTGCAGAAACCAGGCCAGTCTCCACAGCTCCTGATC
JNJ200    GACCCCAGAAAATCGGTTGGAAACTCTGTAGATCAGGAGCTGTGGAGACTG
JNJ201    TCCAACCGATTTTCTGGGGTCCCAGACAGGTTCAGTGGCAGTGGATCAGGG
JNJ202    CACTCTGCTGATCTTGAGTGTGAAATCTGTCCCTGATCCACTGCCACTGAA
JNJ203    ACACTCAAGATCAGCAGAGTGGAGGCTGAGGATGTCGGAGTTTATTACTGC
JNJ204    GAACGTCCACGGAACAAATGAACCTTGAAAGCAGTAATAAACTCCGACATC
JNJ205    TCATTTGTTCCGTGGACGTTCGGTCAAGGCACCAAAGTGGAAATCAAACGTGAGTAG
JNJ206    GGGACTAGTACCACCATGAAGTTGTGGCTGAACTGGATTTTCCTTGTAACACTT
JNJ101    GGGGAATTCTTTAAATTCTACTCACGTTTGATTTCCA
JNJ117    GGGGAATTCTTTAAATTCTA
```

Fig. 24

```
  SpeI
GGGACTAGTACCACC ATG AAG TTG TGG CTG AAC TGG ATT TTC CTT GTA ACA CTT TTA AAT GGT
              ► M   K   L   W   L   N   W   I   F   L   V   T   L   L   N   G
─────────────────────────────────────────────────────────────────────────────
──────────────────►    ◄──────────
      JNJ220             JNJ206              JNJ207

PvuII
TTC CAG TGT GAA GTG CAG CTG GTG GAG TCT GGA GGA GGC TTG GTA CAG CCT GGG GGT TCT
► F   Q   C   E   V   Q   L   V   E   S   G   G   G   L   V   Q   P   G   G   S
─────────────────────────────────────────────────────────────────────────────
                    ──────────────JNJ208──────────────►    ◄──────────
                                                              JNJ209

CTG AGA CTC TCC TGT GCA GCT TCT GGA TTC ACC TTC ACT GAT TAC TAC ATG ATC TGG GTC
► L   R   L   S   C   A   A   S   G   F   T   F   T   D   Y   Y   M   I   W   V
─────────────────────────────────────────────────────────────────────────────
                    ──────────────JNJ210──────────────►    ◄──────────
                                                              JNJ211

CGC CAG GCT CCA GGG AAG GGA CTT GAG TGG TTG GGT TTT ATT AGA AAC AAA GCT AAT GGT
► R   Q   A   P   G   K   G   L   E   W   L   G   F   I   R   N   K   A   N   G
─────────────────────────────────────────────────────────────────────────────
                    ──────────────JNJ212──────────────►    ◄──────────
                                                              JNJ213

TAC ACA ACA GAG TAC AGT GCA TCT GTG AAG GGT CGG TTC ACC ATC TCC AGA GAT AAT GCC
► Y   T   T   E   Y   S   A   S   V   K   G   R   F   T   I   S   R   D   N   A
─────────────────────────────────────────────────────────────────────────────
                    ──────────────JNJ214──────────────►    ◄──────────
                                                              JNJ215

AAG AAC TCA CTC TAT CTT CAA ATG AAC TCC CTG AGA GCT GAG GAC ACG GCC GTG TAT TAC
► K   N   S   L   Y   L   Q   M   N   S   L   R   A   E   D   T   A   V   Y   Y
─────────────────────────────────────────────────────────────────────────────
                    ──────────────JNJ216──────────────►    ◄──────────
                                                              JNJ217

TGT GCA AGG GGC GCT TAC TGG GGC CAA GGG ACT ATG GTC ACT GTC TCT TCA GGTAAGATGGGC
► C   A   R   G   A   Y   W   G   Q   G   T   M   V   T   V   S   S              ◄──────
                                                                                    JNJ221
─────────────────────────────────────────────────────────────────────────────
                    ──────────────JNJ218──────────────►    
                                                              JNJ219

HindIII
TTTCCAAGCTTCCC
──────────────
──────────────
```

Fig. 25

```
     NheI
     GGGCTAGCACCACC ATG AGG ACC CCT GCT CAG TTT CTT GGA ATC TTG TTG CTC TGG TTT CCA
                  ▶  M   R   T   P   A   Q   F   L   G   I   L   L   L   W   F   P
     ────────────────────────▶       JNJ193 ◀──────────────────────────────────────
     ──────────JNJ116──────▶                                JNJ194

GGT ATC AAA TGT GAT ATT GTG ATG ACC CAA TCT CCA CTC TCC CTG CCT GTC ACT CCT GGA
   ▶  G   I   K   C   D   I   V   M   T   Q   S   P   L   S   L   P   V   T   P   G
     ─────────────────────────────────────────▶       JNJ195 ◀─────────────────────
                                         JNJ196

GAG CCA GCC TCC ATC TCT TGC AGA TCT AGT CAG AGC ATT GTA CAT AGT AAT GGA AAC ACC
   ▶  E   P   A   S   I   S   C   R   S   S   Q   S   I   V   H   S   N   G   N   T
     ─────────────────────────────────────────▶       JNJ197 ◀─────────────────────
                                         JNJ198

TAT TTA GAA TGG TAC CTG CAG AAA CCA GGC CAG TCT CCA CAG CTC CTG ATC TAC AGA GTT
   ▶  Y   L   E   W   Y   L   Q   K   P   G   Q   S   P   Q   L   L   I   Y   R   V
     ─────────────────────────────────────▶       JNJ199 ◀─────────────────────────
                                         JNJ200

TCC AAC CGA TTT TCT GGG GTC CCA GAC AGG TTC AGT GGC AGT GGA TCA GGG ACA GAT TTC
   ▶  S   N   R   F   S   G   V   P   D   R   F   S   G   S   G   T   D   F
     ─────────────────────────────────────▶       JNJ201 ◀─────────────────────────
                                         JNJ202

ACA CTC AAG ATC AGC AGA GTG GAG GCT GAG GAT GTC GGA GTT TAT TAC TGC TTT CAA GGT
   ▶  T   L   K   I   S   R   V   E   A   E   D   V   G   V   Y   Y   C   F   Q   G
     ─────────────────────────────────────▶       JNJ203 ◀─────────────────────────
                                         JNJ204

TCA TTT GTT CCG TGG ACG TTC GGT CAA GGC ACC AAG GTG GAA ATC AAA CGTGAGTAGAATTTAAA
   ▶  S   F   V   P   W   T   F   G   Q   G   T   K   V   E   I   K
     ─────────────────────────────────────▶       JNJ205       ◀──────────────
                                                           JNJ101 ◀──────
                                                                      JNJ117

EcoRI
     GAATTCCCC
     ─────────
     ─────────
```

Fig. 26

```
SpeIACTAGTACCACCATGAAGTTGTGGCTGAACTGGATTTTCCTTGTAACACTTTTAAATGGT
           M  K  L  W  L  N  W  I  F  L  V  T  L  L  N  G

TTCCAGTGTGAAGTGCAGCTGGTGGAGTCTGGAGGAGGCTTGGTACAGCCTGGGGGTTCT
 F  Q  C  E  V  Q  L  V  E  S  G  G  G  L  V  Q  P  G  G  S

CTGAGACTCTCCTGTGCAGCTTCTGGATTCACCTTCACTGATTACTACATGATCTGGGTC
 L  R  L  S  C  A  A  S  G  F  T  F  T  D  Y  Y  M  I  W  V

CGCCAGGCTCCAGGGAAGGGACTTGAGTGGTTGGGTTTTATTAGAAACAAAGCTAATGGT
 R  Q  A  P  G  K  G  L  E  W  L  G  F  I  R  N  K  A  N  G

TACACAACAGAGTACAGTGCATCTGTGAAGGGTCGGTTCACCATCTCCAGAGATAATGCC
 Y  T  T  E  Y  S  A  S  V  K  G  R  F  T  I  S  R  D  N  A

AAGAACTCACTCTATCTTCAAATGAATTCCCTGAGAGCTGAGGACACGGCCGTGTATTAC
 K  N  S  L  Y  L  Q  M  N  S  L  R  A  E  D  T  A  V  Y  Y

TGTGCAAGGGGCGCTTACTGGGGCCAAGGGACTATGGTCACTGTCTCTTCAGGTAAGATG
 C  A  R  G  A  Y  W  G  Q  G  T  M  V  T  V  S  S

HindIII
GGCTTTCCAAGCTT
```

Fig. 27

```
NheIGCTAGCACCACCATGAGGACCCCTGCTCAGTTTCTTGGAATCTTGTTGCTCTGGTTTCCA
        M   R   T   P   A   Q   F   L   G   I   L   L   W   F   P

GGTATCAAATGTGATATTGTGATGACCCAATCTCCACTCTCCCTGCCTGTCACTCCTGGA
 G   I   K   C   D   I   V   M   T   Q   S   P   L   S   L   P   V   T   P   G

GAGCCAGCCTCCATCTCTTGCAGATCTAGTCAGAGCATTGTACATAGTAATGGAAACACC
 E   P   A   S   I   S   C   R   S   S   Q   S   I   V   H   S   N   G   N   T

TATTTAGAATGGTACCTGCAGAAACCAGGCCAGTCTCCACAGCTCCTGATCTACAGAGTT
 Y   L   E   W   Y   L   Q   K   P   G   Q   S   P   Q   L   L   I   Y   R   V

TCCAACCGATTTTCTGGGGTCCCAGACAGGTTCAGTGGCAGTGGATCAGGGACAGATTTC
 S   N   R   F   S   G   V   P   D   R   F   S   G   S   G   S   G   T   D   F

ACACTCAAGATCAGCAGAGTGGAGGCTGAGGATGTCGGAGTTTATTACTGCTTTCAAGGT
 T   L   K   I   S   R   V   E   A   E   D   V   G   V   Y   Y   C   F   Q   G

TCATTTGTTCCGTGGACGTTCGGTCAAGGCACCAAAGTGGAAATCAAACGTGAGTAGAAT
 S   F   V   P   W   T   F   G   Q   G   T   K   V   E   I   K

EcoRI
TTAAAGAATTC
```

Fig. 28

```
ATGGGATGGAGCTGTATCATCCTCTTTTTGGTAGCAGCAGCTACAGGTGTCCACTCCCAG
 M  G  W  S  C  I  I  L  F  L  V  A  A  A  T  G  V  H  S  Q

GTCCAACTGCAGCAGCCTGGGACTGAACTGGTGAAGCCTGGGGCTTCAGTGAAGCTGTCC
 V  Q  L  Q  Q  P  G  T  E  L  V  K  P  G  A  S  V  K  L  S

TGTAAGGCTTCTGGCTACACCTTCACCAACTACTGGATGCACTGGGTGAAGCAGAGGCCT
 C  K  A  S  G  Y  T  F  T  N  Y  W  M  H  W  V  K  Q  R  P

GGACAAGGCCTTGAGTGGATTGGAAATATTAATCCTAGAAATGGTGATTCTAACTACAAT
 G  Q  G  L  E  W  I  G  N  I  N  P  R  N  G  D  S  N  Y  N

GAGAAGTTCAGGAGCAAGGCCTCACTGACTGTAGACAAATCCTCCAGCACAGTCTACATG
 E  K  F  R  S  K  A  S  L  T  V  D  K  S  S  S  T  V  Y  M

CAGCTCAGTAGCCTGACATCTGAGGACTCTGCGGTCTATTATTGTGCAAGAGGGTACTTC
 Q  L  S  S  L  T  S  E  D  S  A  V  Y  Y  C  A  R  G  Y  F

GATGTCTGGGGCACAGGGACCACGGTCACCGTCTCCTCA
 D  V  W  G  T  G  T  T  V  T  V  S  S
```

Fig. 29

```
ATGAGGACCCCTGCTCAGTTTCTTGGAATCTTGTTGCTCTGGTTTCCAGGTATCAAATGT
 M   R   T   P   A   Q   F   L   G   I   L   L   W   F   P   G   I   K   C

GACATCAAGATGACCCAGTCTCCATCTTCCATGTATGCATCTCTAGGAGAGAGTCTCT
 D   I   K   M   T   Q   S   P   S   S   M   Y   A   S   L   G   E   R   V   S

ATCACTTGCAAGGCGAGTCAGGACATTAATAGCTATTTAAGCTGGTTCCAGCAGAAATCA
 I   T   C   K   A   S   Q   D   I   N   S   Y   L   S   W   F   Q   Q   K   S

GGGAAATCTCCTAAGACCCTGATCTATCGTGCAAACAGATTGGTAGATGGGGTCCCATCA
 G   K   S   P   K   T   L   I   Y   R   A   N   R   L   V   D   G   V   P   S

AGGTTCAGTGGCAGTGGATCTGGGCAAGATTTTTCTCTCACCATCAGCAGCCTGGAGTAT
 R   F   S   G   S   G   S   G   Q   D   F   S   L   T   I   S   S   L   E   Y

GAAGACATGGGAATTTATTATTGTCTACAGTATGATGAGTTTCCATTCACGTTCGGCTCG
 E   D   M   G   I   Y   Y   C   L   Q   Y   D   E   F   P   F   T   F   G   S

GGGACAAAGTTGGAAATAAAA
 G   T   K   L   E   I   K
```

Fig. 30

```
SpeI
ACTAGTACCACCATGGGATGGAGCTGTATCATCCTCTTTTTGGTAGCAGCAGCTACAGGT
          M  G  W  S  C  I  I  L  F  L  V  A  A  A  T  G

GTCCACTCCCAGGTCCAACTGCAGCAGCCTGGGACTGAACTGGTGAAGCCTGGGGCTTCA
 V  H  S  Q  V  Q  L  Q  Q  P  G  T  E  L  V  K  P  G  A  S

GTGAAGCTGTCCTGTAAGGCTTCTGGCTACACCTTCACCAACTACTGGATGCACTGGGTG
 V  K  L  S  C  K  A  S  G  Y  T  F  T  N  Y  W  M  H  W  V

AAGCAGAGGCCTGGACAAGGCCTTGAGTGGATTGGAAATATTAATCCTAGAAATGGTGAT
 K  Q  R  P  G  Q  G  L  E  W  I  G  N  I  N  P  R  N  G  D

TCTAACTACAATGAGAAGTTCAGGAGCAAGGCCTCACTGACTGTAGACAAATCCTCCAGC
 S  N  Y  N  E  K  F  R  S  K  A  S  L  T  V  D  K  S  S

ACAGTCTACATGCAGCTCAGTAGCCTGACATCTGAGGACTCTGCGGTCTATTATTGTGCA
 T  V  Y  M  Q  L  S  S  L  T  S  E  D  S  A  V  Y  Y  C  A

AGAGGGTACTTCGATGTCTGGGGCACAGGGACCACGGTCACCGTCTCCTCAGGTAAGCTG
 R  G  Y  F  D  V  W  G  T  G  T  T  V  T  V  S  S

HindIII
GCTTTTTTAAGCTT
```

Fig. 31

```
NheIGCTAGCACCACCATGAGGACCCCTGCTCAGTTTCTTGGAATCTTGTTGCTCTGGTTTCCA
         M  R  T  P  A  Q  F  L  G  I  L  L  L  W  F  P

GGTATCAAATGTGACATCAAGATGACCCAGTCTCCATCTTCCATGTATGCATCTCTAGGA
 G  I  K  C  D  I  K  M  T  Q  S  P  S  S  M  Y  A  S  L  G

GAGAGAGTCTCTATCACTTGCAAGGCGAGTCAGGACATTAATAGCTATTTAAGCTGGTTC
 E  R  V  S  I  T  C  K  A  S  Q  D  I  N  S  Y  L  S  W  F

CAGCAGAAATCAGGGAAATCTCCTAAGACCCTGATCTATCGTGCAAACAGATTGGTAGAT
 Q  Q  K  S  G  K  S  P  K  T  L  I  Y  R  A  N  R  L  V  D

GGGGTCCCATCAAGGTTCAGTGGCAGTGGATCTGGGCAAGATTTTCTCTCACCATCAGC
  G  V  P  S  R  F  S  G  S  G  S  G  Q  D  F  S  L  T  I  S

AGCCTGGAGTATGAAGACATGGGAATTTATTATTGTCTACAGTATGATGAGTTTCCATTC
 S  L  E  Y  E  D  M  G  I  Y  Y  C  L  Q  Y  D  E  F  P  F

EcoRI
ACGTTCGGCTCGGGGACAAAGTTGGAAATAAAACGTAAGTAGACTTTTGCGAATTC T  F  G  S
 G  T  K  L  E  I  K
```

Fig. 33

```
                   1          2          3          4
          123456789 0123456789 0123456789 0123456789 0123456789
35B6      QVQLQQPGT ELVKPGASVK LSCKASGYTF TNYWMHWVKQ RPGQGLEWIG
Hu35B6    QVQLVQSGA EVKKPGASVK VSCKASGYTF TNYWMHWVRQ APGQGLEWIG
Z47230    QVQLVQSGA EVKKPGASVK VSCKASGYTF T-----WVRQ APGQGLEWMG 5          6          7          8
          01223456789 0123456789 0123456789 0122223456789
          a                                abc
35B6      NINPRNGDSNY NEKFRSKASL TVDKSSSTVY MQLSSLTSEDSAV
Hu35B6    NINPRNGDSNY NEKFRSKASL TVDKSTSTVY MELSSLRSEDTAV
Z47230    ----------- ------RVTM TRDTSTSTVY MELSSLRSEDTAV 1          1
            9       0          1
          0123456789 0123456789 0123
35B6      YYCARGYF-- -DVWGTGTTV TVSS
Hu35B6    YYCARGYF-- -DVWGQGTTV TVSS
Z47230    YYCAR----- ---WGQGTTV TVSS
```

Fig. 34

```
                        1          2          3
               123456789 0123456789 0123456789 0123456789
35B6            DIKMTQSPS SMYASLGERV SITCKASQDI NSYLSWFQQK
Hu35B6 DIQMTQSPS SLSASVGDRV TITCKASQDI NSYLSWFQQK
X72479 DIQMTQSPS SLSASVGDRV TITC------ -----WFQQK 4          5          6          7
               0123456789 0123456789 0123456789 0123456789
35B6            SGKSPKTLIY RANRLVDGVP SRFSGSGSGQ DFSLTISSLE
Hu35B6 PGKAPKTLIY RANRLVDGVP SRFSGSGSGQ DFTLTISSLQ
X72479 PGKAPKSLIY -------GVP SKFSGSGSGT DFTLTISSLQ 1
                8          9          0
               0123456789 0123456789 01234567
35B6            YEDMGIYYCL QYDEFPFTFG SGTKLEIK
Hu35B6 PEDFATYYCL QYDEFPFTFG QGTKLEIK
X72479 PEDFATYYC- --------FG QGTKLEIK
```

Fig. 35

| | |
|---|---|
| JNJ220 | GGGACTAGTACCACCATGAAG |
| JNJ206 | GGGACTAGTACCACCATGAAGTTGTGGCTGAACTGGATTTTCCTTGTAACACTT |
| JNJ234 | CAGTTGGACCTGACACTGGAAACCATTTAAAAGTGTTACAAGGAAAATCCA |
| JNJ235 | TTCCAGTGTCAGGTCCAACTGGTGCAGTCTGGGGCTGAAGTGAAGAAGCCT |
| JNJ236 | AGCCTTACAGGACACCTTCACTGAAGCCCCAGGCTTCTTCACTTCAGCCCC |
| JNJ237 | GTGAAGGTGTCCTGTAAGGCTTCTGGCTACACCTTCACCAACTACTGGATG |
| JNJ238 | GCCTTGTCCAGGGGCCTGTCGCACCCAGTGCATCCAGTAGTTGGTGAAGGT |
| JNJ239 | CGACAGGCCCCTGGACAAGGCCTTGAGTGGATTGGAAATATTAATCCTAGA |
| JNJ240 | GAACTTCTCATTGTAGTTAGAATCACCATTTCTAGGATTAATATTTCCAAT |
| JNJ241 | TCTAACTACAATGAGAAGTTCAGGAGCAAGGCCTCACTGACTGTAGACAAA |
| JNJ242 | ACTGAGCTCCATGTAGACTGTGCTCGTGGATTTGTCTACAGTCAGTGAGGC |
| JNJ243 | ACAGTCTACATGGAGCTCAGTAGCCTGAGATCTGAGGACACTGCGGTCTAT |
| JNJ244 | CCAGACATCGAAGTACCCTCTTGCACAATAATAGACCGCAGTGTCCTCAGA |
| JNJ245 | AGAGGGTACTTCGATGTCTGGGGCCAAGGGACCACGGTCACCGTCTCCTCA |
| JNJ246 | GGGAAGCTTGAGTGGCCATTCTTACCTGAGGAGACGGTGACCGTGGT |
| JNJ247 | GGGAAGCTTGAGTGGCCATTC |

Fig. 36

```
JNJ116   GGGCTAGCACCACCATGAGG
JNJ193   GGGCTAGCACCACCATGAGGACCCCTGCTCAGTTTCTTGGAATCTTGTTGCTC
JNJ222   CTGGATGTCACATTTGATACCTGGAAACCAGAGCAACAAGATTCCAAGAAA
JNJ223   GGTATCAAATGTGACATCCAGATGACCCAGTCTCCATCTTCCCTGTCTGCA
JNJ224   GCAAGTGATAGTGACTCTGTCTCCTACAGATGCAGACAGGGAAGATGGAGA
JNJ225   GACAGAGTCACTATCACTTGCAAGGCGAGTCAGGACATTAATAGCTATTTA
JNJ226   AGCTTTCCCTGGTTTCTGCTGGAACCAGCTTAAATAGCTATTAATGTCCTG
JNJ227   CAGCAGAAACCAGGGAAAGCTCCTAAGACCCTGATCTATCGTGCAAACAGA
JNJ228   ACTGAACTTTGATGGGACCCCATCTACCAATCTGTTTGCACGATAGATCAG
JNJ229   GGGGTCCCATCAAAGTTCAGTGGCAGTGGATCTGGGCAAGATTTTACTCTC
JNJ230   AAAGTCTTCAGGCTGCAGGCTGCTGATGGTGAGAGTAAAATCTTGCCCAGA
JNJ231   AGCCTGCAGCCTGAAGACTTTGCAACTTATTATTGTCTACAGTATGATGAG
JNJ232   CTTTGTCCCCTGGCCGAACGTGAATGGAAACTCATCATACTGTAGACAATA
JNJ233   ACGTTCGGCCAGGGGACAAAGTTGGAAATCAAACGTGAGTAGAA
JNJ101   GGGGAATTCTTTAAATTCTACTCACGTTTGATTTCCA
JNJ117   GGGGAATTCTTTAAATTCTA
```

Fig. 37

```
       SpeI
       GGGACTAGTACCACC ATG AAG TTG TGG CTG AAC TGG ATT TTC CTT GTA ACA CTT TTA AAT GGT
                        M   K   L   W   L   N   W   I   F   L   V   T   L   L   N   G
       ─────────────────────────────────────────────────────────────▶
       ──────────────▶   ◀──────────────
            JNJ220            JNJ206                      JNJ234

TTC CAG TGT CAG GTC CAA CTG GTG CAG TCT GGG GCT GAA GTG AAG AAG CCT GGG GCT TCA
        F   Q   C   Q   V   Q   L   V   Q   S   G   A   E   V   K   K   P   G   A   S
       ────────────────────────────────▶   ◀────────────────────────
                         JNJ235                         JNJ236

GTG AAG GTG TCC TGT AAG GCT TCT GGC TAC ACC TTC ACC AAC TAC TGG ATG CAC TGG GTG
        V   K   V   S   C   K   A   S   G   Y   T   F   T   N   Y   W   M   H   W   V
       ────────────────────────────────▶        ◀───────────────────
                         JNJ237                              JNJ238

CGA CAG GCC CCT GGA CAA GGG CTT GAG TGG ATT GGA AAT ATT AAT CCT AGA AAT GGT GAT
        R   Q   A   P   G   Q   G   L   E   W   I   G   N   I   N   P   R   N   G   D
       ────────────────────────────────▶       ◀────────────────────
                         JNJ239                             JNJ240

TCT AAC TAC AAT GAG AAG TTC AGG AGC AAG GCC TCA CTG ACT GTA GAC AAA TCC ACG AGC
        S   N   Y   N   E   K   F   R   S   K   A   S   L   T   V   D   K   S   T   S
       ────────────────────────────────▶        ◀───────────────────
                         JNJ241                              JNJ242

ACA GTC TAC ATG GAG CTC AGT AGC CTG AGA TCT GAG GAC ACT GCG GTC TAT TAT TGT GCA
        T   V   Y   M   E   L   S   S   L   R   S   E   D   T   A   V   Y   Y   C   A
       ────────────────────────────────▶        ◀───────────────────
                         JNJ243                              JNJ244

AGA GGG TAC TTC GAT GTC TGG GGC CAA GGG ACC ACG GTC ACC GTC TCC TCA GGTAAGAATGGC
        R   G   Y   F   D   V   W   G   Q   G   T   T   V   T   V   S   S              ◀JNJ247
       ────────────────────────────────▶        ◀───────────────────
                         JNJ245                              JNJ246

HindIII
       CACTCAAGCTTCCC
       ──────────────
       ──────────────
```

Fig. 38

```
        NheI
        GGGGCTAGCACCACC ATG AGG ACC CCT GCT CAG TTT CTT GGA ATC TTG TTG CTC TGG TTT CCA
                      ▶ M   R   T   P   A   Q   F   L   G   I   L   L   L   W   F   P
        ─────────────────────────────────────────────────────────────────────▶
        ─────────────────▶              ◀──────────────────────────
              JNJ116             JNJ193                    JNJ222

GGT ATC AAA TGT GAC ATC CAG ATG ACC CAG TCT CCA TCT TCC CTG TCT GCA TCT GTA GGA
      ▶  G   I   K   C   D   I   Q   M   T   Q   S   P   S   S   L   S   A   S   V   G
                              ───────────────────────────────────────────▶
                                         JNJ223            ◀────────────────────
                                                                   JNJ224

GAC AGA GTC ACT ATC ACT TGC AAG GCG AGT CAG GAC ATT AAT AGC TAT TTA AGC TGG TTC
      ▶  D   R   V   T   I   T   C   K   A   S   Q   D   I   N   S   Y   L   S   W   F
        ──────────────────────────────────────────▶
                        JNJ225                    ◀──────────────────
                                                            JNJ226

CAG CAG AAA CCA GGG AAA GCT CCT AAG ACC CTG ATC TAT CGT GCA AAC AGA TTG GTA GAT
      ▶  Q   Q   K   P   G   K   A   P   K   T   L   I   Y   R   A   N   R   L   V   D
        ──────────────────────────────────────────▶
                        JNJ227                    ◀──────────────────
                                                            JNJ228

GGG GTC CCA TCA AAG TTC AGT GGC AGT GGA TCT GGG CAA GAT TTT ACT CTC ACC ATC AGC
      ▶  G   V   P   S   K   F   S   G   S   G   S   G   Q   D   F   T   L   T   I   S
        ──────────────────────────────────────────▶
                        JNJ229                    ◀──────────────────
                                                            JNJ230

PstI
        AGC CTG CAG CCT GAA GAC TTT GCA ACT TAT TAT TGT CTA CAG TAT GAT GAG TTT CCA TTC
      ▶  S   L   Q   P   E   D   F   A   T   Y   Y   C   L   Q   Y   D   E   F   P   F
        ──────────────────────────────────────────▶
                        JNJ231                    ◀──────────────────
                                                            JNJ232

EcoRI
        ACG TTC GGC CAG GGG ACA AAG TTG GAA ATC AAA CGTGAGTAGAATTTAAAGAATTCCC
      ▶  T   F   G   Q   G   T   K   L   E   I   K
        ────────────────────────────▶
                    JNJ233                ◀──────────
                                              JNJ101   ◀──────
                                                         JNJ117
```

Fig. 39

```
SpeIACTAGTACCACCATGAAGTTGTGGCTGAACTGGATTTTCCTTGTAACACTTTTAAATGGT
        M  K  L  W  L  N  W  I  F  L  V  T  L  L  N  G

TTCCAGTGTCAGGTCCAACTGGTGCAGTCTGGGGCTGAAGTGAAGAAGCCTGGGGCTTCA
 F  Q  C  Q  V  Q  L  V  Q  S  G  A  E  V  K  K  P  G  A  S

GTGAAGGTGTCCTGTAAGGCTTCTGGCTACACCTTCACCAACTACTGGATGCACTGGGTG
 V  K  V  S  C  K  A  S  G  Y  T  F  T  N  Y  W  M  H  W  V

CGACAGGCCCCTGGACAAGGGCTTGAGTGGATTGGAAATATTAATCCTAGAAATGGTGAT
 R  Q  A  P  G  Q  G  L  E  W  I  G  N  I  N  P  R  N  G  D

TCTAACTACAATGAGAAGTTCAGGAGCAAGGCCTCACTGACTGTAGACAAATCCACGAGC
 S  N  Y  N  E  K  F  R  S  K  A  S  L  T  V  D  K  S  T  S

ACAGTCTACATGGAGCTCAGTAGCCTGAGATCTGAGGACACTGCGGTCTATTATTGTGCA
 T  V  Y  M  E  L  S  S  L  R  S  E  D  T  A  V  Y  Y  C  A

AGAGGGTACTTCGATGTCTGGGGCCAAGGGACCACGGTCACCGTCTCCTCAGgtaagaat
 R  G  Y  F  D  V  W  G  Q  G  T  T  V  T  V  S  S HindIII
GGCCACTCAAGCTT
```

Fig. 40

```
NheIGCTAGCACCACCATGAGGACCCCTGCTCAGTTTCTTGGAATCTTGTTGCTCTGGTTTCCA
          M  R  T  P  A  Q  F  L  G  I  L  L  L  W  F  P

GGTATCAAATGTGACATCCAGATGACCCAGTCTCCATCTTCCCTGTCTGCATCTGTAGGA
 G  I  K  C  D  I  Q  M  T  Q  S  P  S  S  L  S  A  S  V  G

GACAGAGTCACTATCACTTGCAAGGCGAGTCAGGACATTAATAGCTATTTAAGCTGGTTC
 D  R  V  T  I  T  C  K  A  S  Q  D  I  N  S  Y  L  S  W  F

CAGCAGAAACCAGGGAAAGCTCCTAAGACCCTGATCTATCGTGCAAACAGATTGGTAGAT
 Q  Q  K  P  G  K  A  P  K  T  L  I  Y  R  A  N  R  L  V  D

GGGGTCCCATCAAAGTTCAGTGGCAGTGGATCTGGGCAAGATTTTACTCTCACCATCAGC
 G  V  P  S  K  F  S  G  S  G  S  G  Q  D  F  T  L  T  I  S

AGCCTGCAGCCTGAAGACTTTGCAACTTATTATTGTCTACAGTATGATGAGTTTCCATTC
 S  L  Q  P  E  D  F  A  T  Y  Y  C  L  Q  Y  D  E  F  P  F

EcoRI
ACGTTCGGCCAGGGGACAAAGTTGGAAATCAAACGTGAGTAGAATTTAAAGAATTC
 T  F  G  Q  G  T  K  L  E  I  K
```

US 8,614,296 B2

HUMANIZED ANTIBODIES SPECIFIC FOR AMINO ACID SEQUENCE RGD OF AN EXTRACELLULAR MATRIX PROTEIN AND THE USES THEREOF

CROSS-REFERENCE TO RELATED APPLICATIONS

This application is a National Stage application of PCT/JP2009/058604, filed Apr. 24, 2009, which claims priority from U.S. Provisional Application No. 61/047,604, filed Apr. 24, 2008.

1. FIELD OF THE INVENTION

The present invention relates to humanized antibodies that immunospecifically recognize amino acid sequence RGD (Arg-Gly-Asp) of an extracellular matrix protein and to their therapeutic and diagnostic uses for various diseases or disorders including cancer, inflammatory diseases, autoimmune diseases, infectious disease, bone disease and the like.

Throughout this provisional application, several publications (including patents and patent applications) are referenced herein. Disclosure of these publications in their entirety is hereby incorporated by reference into this provisional application to more fully describe the state of the art to which the present invention pertains.

2. BACKGROUND OF THE INVENTION

Cell adhesion plays an important role in sustaining life of multicellular organisms. Cell adhesions of multicellular organisms are classified into cell-extracellular matrix (hereinafter abbreviated as "ECM") adhesion and cell-cell adhesion. It has been elucidated that cell-ECM adhesion is mediated by integrins and cell-cell adhesion is mediated by cadherins, claudins and nectins.

Transmembrane adhesion proteins, such as integrins, constitute cell-ECM adhesions. Integrin forms heterodimer of α and β chains. At least 18 types of α chain, 8 types of β chain and 24 types of αβ heterodimer have been identified and confirmed so far. Each type of integrin recognizes a specific ligand. Transmembrane adhesion proteins including integrins relate to, in addition to cell adhesions, intracellular signal transductions from ECM into a cell and regulation of proliferation, mobility and differentiation (F. G. Giancotti, et. al., Science, 285, 1028-1032, 1999).

Many proteins are known as ECM proteins which are classified into collagens (such as type I-XIX), non-collagenous glycoproteins (such as osteopontin (OPN), vitronectin, fibronectin, von Willebrand Factor, laminin, tenascin, fibrinogen, thrombospondin), elastins and proteoglycans. These ECM proteins bind to corresponding integrins and activate intracellular signal transduction pathways to regulate cytoskeletal organization, mobility, proliferation, differentiation, and the like. ECM protein-bound integrin regulates these signal activating pathways by transmitting specific signals depending on the type of ECM protein. The RGD sequence is commonly observed in cell adhesion region of many ECM proteins and exhibits various functions by binding to integrins. The RGD sequence of ECM proteins has been viewed as a possible target for drugs, and a number of small molecule compounds and artificial peptides have been provided.

Some types of integrins such as α3β1 integrin, α5β1 integrin, α8β1 integrin, αvβ1 integrin, αvβ3 integrin, αvβ5 integrin, αvβ6 integrin, αvβ8 integrin have been known to bind to the RGD sequence. The interaction between α5β1 integrin and its specific ligand fibronectin has inspired investigations into the mechanisms of integrin mediated signal transduction. Such investigations show that α5β1 integrin regulates not only cell adhesion and cell mobility, but also cell differentiation and cell mortality. (S. M. Frisch et al., Curr. Opin. Cell Biol., 9, 701-706, 1997). It has also been shown that α5β1 integrin is highly expressed on tumor cells and relates to malignant alteration of cancer. Each integrin mediated signal differs depending on binding ECM proteins, for example, stimulation by growth factor activates growth of fibronectin-bound endothelial cells, but inhibits growth of laminin-1 bound endothelial cells. Also, the signal transmitted from laminin-10/11 to α3β1 integrin is different from the signal transmitted from fibronectin to α5β1 integrin, and significantly enhances mobility of cancerous cells (J. Gu et al., J. Biol. Chem., 276, 27090-27097, 2001) and significantly avoids apoptosis by blood starvation (J. Gu et al., J. Biol. Chem., 277, 19922-19928, 2002). High expression of RGD sequence binding αv integrins has been observed in the osteoclastic cells and neovascular, and inhibition of the RGD sequence and the αv integrins has been viewed as a target for a therapeutic drug for osteoporosis and cancer. It has been indicated that α5β1 integrin is highly expressed on tumor cells and relates to malignant alteration of cancer. From these findings, anti-α5β1 integrin antibody (Volocimab), anti-α4 integrin antibody (Natalizumab), and anti-αvβ3 integrin antibody (Vitaxin) have been developed as antagonistic anti-integrin antibody drugs which inhibit interaction between integrin and ECM protein.

Meanwhile, some ECM proteins such as collagen, osteopontin (OPN), vitronectin, fibronectin, von Willebrand Factor, laminin, tenascin, fibrinogen and thrombospondin have been known to include RGD sequence. Also, some virus and some bacterium have been known to possess RGD sequence to adhere to cells. OPN is an acidic glycoprotein with binding properties to calcium which is contained rich in bone. It is reported that OPN plays an important role in cell adhesion, cell migration, tumor formation, immune response and complement mediated cellular lysis. Outcomes of OPN knockout mice and anti-OPN neutralizing antibodies indicate that OPN relates to hepatitis, autoimmune disease (such as rheumatoid arthritis), and metastasis of cancer. It has been noted that an inhibitor of binding of ECM proteins to cells may be used for treating osteoporosis or cancer. Thus, in addition to the above-mentioned antagonistic drugs targeted to integrins, antagonistic drugs targeted to the ECM proteins which are binding partner of the integrins have been developed.

3. SUMMARY OF THE INVENTION

Although drugs such as small molecules that inhibit the RGD sequence mediated interaction with integrin, antibodies against OPN, and antibodies against integrins have been reported, there are no reports regarding an antibody which specifically recognizes the RGD sequence. Since the RGD sequence is one of the conserved sequences in ECM proteins, an antibody which specifically recognizes the RGD sequence may have an effect in both human and therapeutic model animals, and, hence, may be considered as a very useful active ingredient for the development of a therapeutic agent. Hence, there is a need for such an antibody which specifically recognizes the RGD sequence.

Previously, the inventors isolated mouse monoclonal antibodies that immunospecifically recognize the RGD sequence and are produced by hybridoma clones 33E10 and 35B6 (Depository Accession Nos. FERM BP-10440 and FERM BP-10441, respectively). Herein, the hybridoma clone designations are interchangeably used as the designations of the monoclonal antibodies produced by the clones. All of these mouse anti-RGD antibodies were of IgG1 isotype. These monoclonal antibodies were observed to interfere with RGD sequence-mediated binding between ECM and a cell by binding to the RGD sequence of ECM proteins such as osteopontin. Thus, these anti-RGD antibodies may exhibit therapeutic or diagnostic effects on the RGD sequence-related disease such as cancer, e.g., the growth or metastasis of cancer cells, and inflammatory diseases, e.g., rheumatoid arthritis, osteoarthritis, infectious disease, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, osteoporosis, and the like.

However, since these monoclonal antibodies are of mouse origin, possible adverse effects due to their immunogenicity in humans have hampered their direct applications to diagnostic or therapeutic uses in humans. In order to reduce the immunogenicity, the present inventors have prepared a humanized antibody that have biological activities corresponding to those exhibited by the original mouse anti-RGD antibody from which said humanized antibody was derived.

Accordingly, the present invention provides a humanized antibody or an antigen-binding fragment thereof, which immunospecifically recognizes the RGD sequence, said antibody or an antigen-binding fragment thereof comprising an antigen-binding region partially derived from a non-human origin and partially derived from a human origin. In some embodiment, the humanized antibody or the antigen-binding fragment thereof of the present invention comprises a complementarity determining region (hereinafter abbreviated as "CDR") derived from a non-human source (donor) such as 33E10 and 35B6 monoclonal antibodies, and a framework region (hereinafter abbreviated as "FR") derived from a human source (acceptor). Said humanized antibody or an antigen-binding fragment thereof may inhibit the binding between the RGD sequence and a ligand thereof.

In specific embodiments, said humanized antibody or an antigen-binding fragment thereof that immunospecifically recognizes the RGD sequence comprises: (i) a heavy chain (hereinafter abbreviated as "H-chain") comprising at least one H-chain FR (hereinafter abbreviated as "FRH") derived from a variable region (hereinafter abbreviated as "V-region") of a human H-chain, and at least one H-chain CDR (hereinafter abbreviated as "CDRH") derived from at least one of the CDRHs of a non-human antibody that immunospecifically recognizes the RGD sequence; or (ii) a light chain (hereinafter abbreviated as "L-chain") comprising at least one L-chain FR (hereinafter abbreviated as "FRL") derived from a V-region of a human L-chain, and at least one L-chain CDR (hereinafter abbreviated as "CDRL") derived from at least one of the CDRLs of a non-human antibody that immunospecifically recognizes the RGD sequence; or both (i) and (ii) above. In one embodiment, at least one of the CDRHs and/or at least one of the CDRLs of the humanized antibody of the present invention may be derived from a monoclonal antibody produced by a hybridoma selected from the group consisting of Depository Accession Nos. FERM BP-10440 and FERM BP-10441. In preferred embodiments, the humanized antibody or an antigen-binding fragment thereof of the present invention comprises: (i) at least one FRH derived from a human FRH, and at least one CDRH comprising an amino acid sequence selected from the group consisting of the amino acid sequences of SEQ ID NOS:1, 2 and 3; or (ii) at least one FRL derived from a human FRL, and at least one CDRL comprising an amino acid sequence selected from the group consisting of the amino acid sequences of SEQ ID NOS. 4, 5 and 6; or (iii) both (i) and (ii) above. In some embodiments, said humanized antibody or an antigen-binding fragment thereof of the present invention may comprise SEQ ID NO:1 at CDRH1, SEQ ID NO:2 at CDRH2 and SEQ ID NO:3 at CDRH3. In some embodiments, said humanized antibody or an antigen-binding fragment thereof of the present invention may comprise SEQ ID NO:4 at CDRL1, SEQ ID NOS: 5 at CDRL2 and SEQ ID NOS: 6 at CDRL3. Preferably, said humanized antibody or an antigen-binding fragment thereof of the present invention comprises SEQ ID NO:1 at CDRH1, SEQ ID NO:2 at CDRH2, SEQ ID NO:3 at CDRH3, SEQ ID NO:4 at CDRL1, SEQ ID NO:5 at CDRL2 and SEQ ID NO:6 at CDRL3.

In some specific embodiments, said humanized antibody or an antigen-binding fragment thereof of the present invention comprises a FRH derived from a V-region of a human H-chain encoded by GenBank Accession No. X65891 (SEQ ID NO:13) or a FRL derived from a V-region of a human κ-L-chain encoded by GenBank Accession No. X72441 (SEQ ID NO:18). In some embodiments, the FRH of the humanized antibody of the present invention comprises at least one amino acid sequence selected from the group consisting of the amino acid sequences of SEQ ID NOS: 14, 15, 16 and 17 (amino acid sequences of FRH1, FRH2, FRH3 and FRH4 of X65891, respectively). In some embodiments, the FRL of the humanized antibody of the present invention comprises at least one amino acid sequence selected from the group consisting of the amino acid sequences of SEQ ID NOS: 19, 20, 21 and 22 (amino acid sequences of FRL1, FRL2, FRL3 and FRL4 of X72441, respectively). In one of the most preferred embodiment, the humanized antibody or an antigen-binding fragment thereof of the present invention comprises: (i) a V-region of H-chain (hereinafter abbreviated as "VH") comprising the amino acid sequence of SEQ ID NO:24; or (ii) a V-region of L-chain (hereinafter abbreviated as "VL") comprising the amino acid sequence of SEQ ID NO:26; or (iii) both (i) and (ii) above.

In the other embodiments, the humanized antibody or an antigen-binding fragment thereof of the present invention comprises: (i) at least one FRH derived from a human FRH, and at least one CDRH comprising an amino acid sequence selected from the group consisting of the amino acid sequences of SEQ ID NOS:7, 8 and 9; or (ii) at least one FRL derived from a human FRL, and at least one CDRL comprising an amino acid sequence selected from the group consisting of the amino acid sequences of SEQ ID NOS:10, 11 and 12; or (iii) both (i) and (ii) above. In some embodiments, said humanized antibody or an antigen-binding fragment thereof of the present invention may comprise SEQ ID NO:7 at CDRH1, SEQ ID NO:8 at CDRH2 and SEQ ID NO:9 at CDRH3. In some embodiments, said humanized antibody or an antigen-binding fragment thereof, of the present invention comprises SEQ ID NO:10 at CDRL1, SEQ ID NO:11 at CDRL2 and SEQ ID NO:12 at CDRL3. Preferably, said humanized antibody or an antigen-binding fragment thereof of the present invention comprises SEQ ID NO:7 at CDRH1, SEQ ID NO:8 at CDRH2, SEQ ID NO:9 at CDRH3, SEQ ID NO:10 at CDRL1, SEQ ID NO:11 at CDRL2 and SEQ ID NO:12 at CDRL3.

In some specific embodiments, said humanized antibody or an antigen-binding fragment thereof of the present invention comprises a FRH derived from a V-region of a human H-chain encoded by GenBank Accession No. X65891 (SEQ ID NO:13) or a FRL derived from a V-region of a human κ-L-chain encoded by GenBank Accession No. X72441

(SEQ ID NO:18). In some embodiments, the FRH of the humanized antibody of the present invention comprises at least one amino acid sequence selected from the group consisting of the amino acid sequences of SEQ ID NOS: 14, 15, 16 and 17 (amino acid sequences of FRH1, FRH2, FRH3 and FRH4 of X65891, respectively). In some embodiments, the FRL of the humanized antibody of the present invention comprises at least one amino acid sequence selected from the group consisting of the amino acid sequences of SEQ ID NOS: 19, 20, 21 and 22 (amino acid sequences of FRL1, FRL2, FRL3 and FRL4 of X72441, respectively). In one of the most preferred embodiment, the humanized antibody or an antigen-binding fragment thereof of the present invention comprises: (i) a VH comprising the amino acid sequence of SEQ ID NO:28; or (ii) a VL comprising the amino acid sequence of SEQ ID NO:30; or (iii) both (i) and (ii) above.

The present invention further provides an isolated nucleic acid molecule comprising a nucleotide sequence encoding the humanized antibody or an antigen-binding fragment thereof of the present invention which immunospecifically recognizes the RGD sequence. Specifically, the present invention provides an isolated nucleic acid molecule comprising a nucleotide sequence encoding a humanized H-chain comprising at least one amino acid sequence selected from the group consisting of SEQ ID NOS:1, 2, 3, 7, 8 and 9, or a humanized L-chain comprising at least one amino acid sequence selected from the group consisting of SEQ ID NOS: 4, 5, 6, 10, 11 and 12, or both said humanized H-chain and said humanized L-chain. In preferred specific embodiments, such an isolated nucleic acid molecule comprises the nucleotide sequence of SEQ ID NO:23, which encodes a VH, or a nucleotide sequence encoding the amino acid sequence of SEQ ID NO:24. In some preferred specific embodiments, such an isolated nucleic acid molecule comprises the nucleotide sequence of SEQ ID NO:25, which encodes a VL, or a nucleotide sequence encoding the amino acid sequence of SEQ ID NO:26. Preferably, the isolated nucleic acid molecule of the present invention comprises the nucleotide sequences both of SEQ ID NO:23 and SEQ ID NO:25. In preferred specific embodiments, the isolated nucleic acid molecule of the present invention further comprises a nucleotide sequence encoding a signal peptide of donor origin, such as the amino acid sequences of SEQ ID NOS:32 and 34, or of heterologous origin.

In the other preferred specific embodiments, such an isolated nucleic acid molecule comprises the nucleotide sequence of SEQ ID NO:27, which encodes a VH, or a nucleotide sequence encoding the amino acid sequence of SEQ ID NO:28. In some preferred specific embodiments, such an isolated nucleic acid molecule comprises the nucleotide sequence of SEQ ID NO:29 which encodes a VL, or a nucleotide sequence encoding the amino acid sequence of SEQ ID NO:30. Preferably, the isolated nucleic acid molecule of the present invention comprises the nucleotide sequences both of SEQ ID NO:27 and SEQ ID NO:29. In preferred specific embodiments, the isolated nucleic acid molecule of the present invention further comprises a nucleotide sequence encoding a signal peptide of donor origin, such as the amino acid sequences of SEQ ID NOS:36 and 38, or of heterologous origin.

The present invention further provides a vector, e.g., an expression vector, comprising a nucleotide sequence encoding a H-chain or a L-chain, or both, of the humanized antibody or an antigen-binding fragment thereof of the present invention that immunospecifically recognizes the RGD sequence. In such a vector, the nucleotide sequence of the present invention may be operably linked to one or more regulatory elements. The nucleotide sequence of the present invention may include a nucleotide sequence encoding a signal peptide native to a non-human donor antibody from which a CDR is derived, or a signal peptide of heterologous origin.

Furthermore, the present invention provides a host cell comprising the nucleic acid molecule of the present invention, including a vector comprising the nucleic acid molecule of the present invention. In one embodiment, the present invention provides an isolated host cell comprising a first nucleic acid molecule encoding a humanized H-chain of the present invention and a second nucleic acid molecule encoding a humanized L-chain of the present invention, said first and second nucleic acid molecules are each operably linked to a regulatory element in such a way that the biologically functional humanized antibody or antigen-binding fragment thereof of the present invention is expressed.

Accordingly, the present invention further provides a method for preparing the humanized antibody or an antigen-binding fragment thereof of the present invention, comprising culturing the host cell of the invention under conditions so that the humanized antibody or an antigen-binding fragment thereof is expressed; and collecting the produced humanized antibody.

The present invention further provides a composition comprising at least one of the humanized antibodies or an antigen-binding fragment thereof of the present invention. In addition, the present invention provides a pharmaceutical composition for preventing or treating a disorder or disease that is associated with the RGD-proteins, comprising at least one of the humanized antibodies or an antigen-binding fragment thereof of the present invention, and a pharmaceutically acceptable carrier. Either of said compositions can further comprise another active compound that can additively or synergistically ameliorate the disorder or disease. Said active compounds include, but not limited to, anti-inflammatory compounds, chemotherapeutic compounds and the like. Said active compounds also include small molecule compounds and antibodies or an antigen-binding fragment thereof, such as human α4 integrin specific antibody or human α9 integrin specific antibody.

In another aspect, the present invention provides a method for preventing or treating a disorder or disease that is associated with or involves the RGD-proteins, said method comprising administering a prophylactically or therapeutically effective amount of at least one of the humanized antibodies or an antigen-binding fragment thereof of the present invention to a subject in need thereof. For such uses, the humanized antibody or an antigen-binding fragment thereof of the present invention may be conjugated to a therapeutic moiety that enhances the biological effect of the humanized antibody or an antigen-binding fragment thereof. Examples of such a therapeutic moiety include another antibody, cytotoxins that are cytostatic or cytocidal, radioactive elements, and/or other therapeutic agents, including anti-inflammatory agents, antibiotics and the like.

In yet another aspect, the present invention provides a method for diagnosing a disorder or disease, in a subject, that is associated with or involves RGD-proteins, said method comprising administering a diagnostically effective amount of the humanized antibody or an antigen-binding fragment thereof of the present invention to a subject to be examined. For such diagnostic uses, the humanized antibody of the present invention may be labeled with detectable markers, such as radioactive elements.

3.1. Definitions

As used herein, the term "antibody" refers to an antibody molecule capable of immunospecifically binding to a desired antigen or a desired sequence (such as the RGD sequence), and encompasses an antibody molecule as a whole or a fragment thereof, including an antigen-binding fragment.

The term "an antigen-binding fragment" used herein refers to any fragment of an antibody that retains an ability to immunospecifically bind to a target polypeptide, protein or sequence, in particular the RGD sequence, which includes single chain antibodies, Fab fragments, F(ab')₂ fragments, disulfide-linked Fvs and fragments containing either a VL and/or a VH or a CDR that specifically binds to a target polypeptide, protein or sequence. Thus, such antigen-binding fragments of humanized antibody may or may not include partial or full-length human constant regions. Various methods for obtaining the antibody fragments described above are well known in the art.

The term "immunospecifically recognize" used herein refers to an ability of an antibody or an antigen-binding fragment thereof to bind specifically to a target polypeptide, protein or sequence, in particular, human RGD sequence. Such an antibody does not non-specifically bind to other polypeptides or proteins. However, an antibody or an antigen-binding fragment thereof that immunospecifically binds to the target polypeptide or protein (e.g., RGD-protein) may cross-react with other antigens. For example, the humanized antibody or an antigen-binding fragment thereof of the present invention that immunospecifically recognizes human RGD-proteins may cross-react with murine RGD-proteins. Preferably, an antibody or an antigen-binding fragment thereof that immunospecifically recognizes RGD-proteins does not cross-react with other antigens.

The term "derived from a human source" or "derived from a non-human source" used herein refers to an antibody portion whose amino acid sequence is derived from a corresponding portion of a human antibody or of a non-human antibody, respectively.

The term "an acceptor sequence" used herein refers to a nucleotide sequence or an amino acid sequence of FRs from a human antibody VH or VL that serves as an acceptor for CDRs from a donor antibody which is usually a non-human antibody.

4. BRIEF DESCRIPTION OF THE FIGURES

FIG. 1 discloses SEQ ID NOS 177, 176, 169, 169, 158, 158, 178, 172, 172, 169, 158 and 172, respectively, in order of appearance.

FIG. 2 discloses SEQ ID NOS 177, 176, 169, 169, 158, 158, 178, 172, 172, 169, 158 and 172, respectively, in order of appearance.

FIG. 3 discloses SEQ ID NOS 176, 176, 170, 173, 170 and 173, respectively, in order of appearance.

FIG. 4 discloses SEQ ID NOS 176, 176, 171, 174, 171 and 174, respectively, in order of appearance.

FIG. 6 shows the result of CDRH analysis of anti RGD monoclonal antibodies. In this Figure, the amino acid (F) at position 99 of 33E10 (SEQ ID NO: 179) and the amino acid (F) at position 98 of 35B6 (SEQ ID NO: 180) may be K or R.

FIG. 7 shows the result of CDRL analysis of anti RGD monoclonal antibodies (SEQ ID NOS 181-182, respectively, in order of appearance).

FIG. 12A indicates the number of metastasis cells and FIG. 12B indicates the change of weight.

FIG. 13A indicates the size of cancer, FIG. 13B indicates the number of metastasis cells, and FIG. 13C indicates the change of weight.

FIG. 15 shows the nucleotide sequence of mouse 33E10 VH cDNA SEQ ID NO: 183) is shown along with the deduced amino acid sequence (SEQ ID NO: 46). Amino acid residues are shown in single letter code. The signal peptide sequence is in italic. The N-terminal amino acid residue (E) of the mature VH is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

FIG. 16 shows the nucleotide sequence of mouse 33E10 VL cDNA (SEQ ID NO: 184) is shown along with the deduced amino acid sequence (SEQ ID NO: 49). Amino acid residues are shown in single letter code. The signal peptide sequence is in italic. The N-terminal amino acid residue (D) of the mature VL is double-underlined. CDR sequences according to the definition of Kabat et al. (1991) are underlined.

FIG. 17 shows the nucleotide sequence of the designed 33E10 VH gene (SEQ ID NO: 45) flanked by SpeI and HindIII sites (underlined) is shown along with the deduced amino acid sequence (SEQ ID NO: 46). Amino acid residues are shown in single letter code. The signal peptide sequence is in italic. The N-terminal amino acid residue (E) of the mature VH is double-underlined. CDR sequences according to the definition of Kabat et al. (1991) are underlined. The intron sequence is in italic.

FIG. 18 shows the nucleotide sequence of the designed 33E10 VL gene (SEQ ID NO: 48) flanked by NheI and EcoRI sites (underlined) is shown along with the deduced amino acid sequence (SEQ ID NO: 49). Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 19:
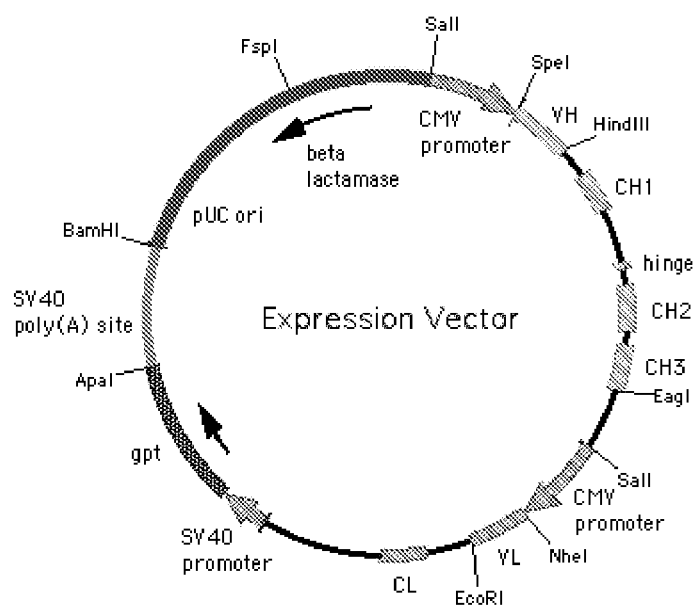

FIG. 19 shows Schematic structure of pCh33E10 and pHu33E10 (collectively Expression Vector). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the E. coli xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene (beta lactamase).

FIG. 20 shows the alignment of the amino acid sequences of 33E10 VH (SEQ ID NO: 40), humanized 33E10 (Hu33E10) VH (SEQ ID NO: 24) and human acceptor U03400 (GenBank accession number) (SEQ ID NO: 185) is shown. Amino acid residues are shown in single letter code. Numbers above the sequences indicate the positions according to Kabat et al. (1991). CDR sequences defined by Kabat et al. (Sequences of Proteins of Immunological Interests, Fifth edition, NIH Publication No. 91-3242, U.S. Department of Health and Human Services, 1991) are underlined. Double-underlined residues were predicted to contact with the CDRs and the mouse residues were retained at these locations in the humanized form. CDR residues in U03400 are omitted in the Figure.

FIG. 21 shows the alignment of the amino acid sequences of 33E10 VL (SEQ ID NO: 43), humanized 33E10 (Hu33E10) VL (SEQ ID NO: 26) and human acceptor X72452 (GenBank accession number) (SEQ ID NO: 186) is shown. Amino acid residues are shown in single letter code. Numbers above the sequences indicate the positions according to Kabat et al. (1991). CDR sequences defined by Kabat et al. (1991) are underlined. CDR residues in X72452 are omitted in the Figure.

FIG. 22 shows oligonucleotides (SEQ ID NOS 91-106, respectively, in order of appearance) used for construction of the Hu33E10 VH gene.

FIG. 23 shows the oligonucleotides (SEQ ID NOS 107-123, respectively, in order of appearance) used for construction of the Hu33E10 VL gene.

FIG. 24 shows the oligonucleotides used for construction of the Hu33E10 VH gene (full-length coding nucleotide sequence disclosed as SEQ ID NO: 51 and coded amino acid sequence disclosed as SEQ ID NO: 187). An arrow denotes the position and orientation (5' to 3') of each oligonucleotide. Amino acid residues are shown in single letter code.

FIG. 25 shows oligonucleotides used for construction of the Hu33E10 VL gene (full-length coding nucleotide sequence disclosed as nucleotides 2-437 of SEQ ID NO: 53 and coded amino acid sequence disclosed as SEQ ID NO: 188). An arrow denotes the position and orientation (5' to 3') of each oligonucleotide. Amino acid residues are shown in single letter code.

FIG. 26 shows the nucleotide sequence of the Hu33E10 VH gene (SEQ ID NO: 52) flanked by SpeI and HindIII sites (underlined) is shown along with the deduced amino acid sequence (SEQ ID NO: 187). Amino acid residues are shown in single letter code. The signal peptide sequence is in italic. The N-terminal amino acid residue (E) of the mature VH is double-underlined. CDR sequences according to the definition of Kabat et al. (1991) are underlined. The intron sequence is in italic.

FIG. 27 shows the nucleotide sequence of the Hu33E10 VL gene (SEQ ID NO: 54) flanked by NheI and EcoRI sites (underlined) is shown along with the deduced amino acid sequence (SEQ ID NO: 188). Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

FIG. 28 shows the nucleotide sequence of mouse 35B6 VH cDNA (SEQ ID NO: 189 is shown along with the deduced amino acid sequence (SEQ ID NO: 62). Amino acid residues are shown in single letter code. The signal peptide sequence is in italic. The N-terminal amino acid residue (Q) of the mature VH is double-underlined. CDR sequences according to the definition of Kabat et al. (Sequences of Proteins of Immunological Interests, Fifth edition, NIH Publication No. 91-3242, U.S. Department of Health and Human Services, 1991) are underlined.

FIG. 29 shows the nucleotide sequence of mouse 35B6 VL cDNA (SEQ ID NO: 190 is shown along with the deduced amino acid sequence (SEQ ID NO: 65). Amino acid residues are shown in single letter code. The signal peptide sequence is in italic. The N-terminal amino acid residue (D) of the mature VL is double-underlined. CDR sequences according to the definition of Kabat et al. (1991) are underlined.

FIG. 30 shows the nucleotide sequence of the designed 35B6 VH gene (SEQ ID NO: 61) flanked by SpeI and HindIII sites (underlined) is shown along with the deduced amino acid sequence (SEQ ID NO: 62). Amino acid residues are shown in single letter code. The signal peptide sequence is in italic. The N-terminal amino acid residue (Q) of the mature VH is double-underlined. CDR sequences according to the definition of Kabat et al. (1991) are underlined. The intron sequence is in italic.

FIG. 31 shows the nucleotide sequence of the designed 35B6 VL gene (SEQ ID NO: 64) flanked by NheI and EcoRI sites (underlined) is shown along with the deduced amino acid sequence (SEQ ID NO: 65). Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 32:
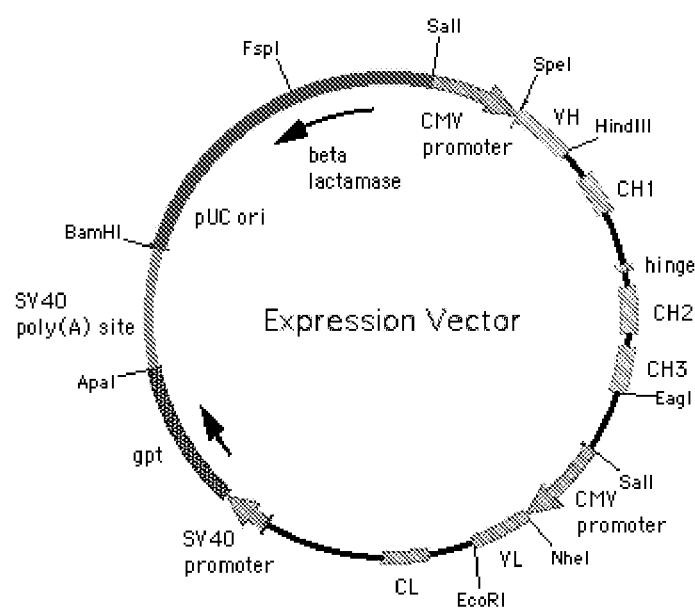

FIG. 32 shows the schematic structure of pCh35B6 and pHu35B6 (collectively Expression Vector). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the E. coli xanthine guanine phosphoribosyl transferase gene (gpt), and a segment containing the SV40 polyadenylation site (SV40 poly(A) site). Finally, the plasmid contains a part of the plasmid pUC19, comprising the bacterial origin of replication (pUC ori) and beta-lactamase gene (beta lactamase).

FIG. 33 shows the alignment of the amino acid sequences of 35B6 VH (SEQ ID NO: 56), humanized 35B6 (Hu35B6) VH (SEQ ID NO: 28) and human acceptor Z47230 (GenBank accession number) (SEQ ID NO: 191) is shown. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in Z47230 are omitted in the Figure.

FIG. 34 shows the alignment of the amino acid sequences of 35B6 VL (SEQ ID NO: 59), humanized 35B6 (Hu35B6) VL (SEQ ID NO: 192) and human acceptor X72479 (GenBank accession number) (SEQ ID NO: 193) is shown. Amino acid residues are shown in single letter code. Numbers above the sequences indicate the positions according to Kabat et al. (1991). CDR sequences defined by Kabat et al. (1991) are underlined. Double-underlined residues were predicted to contact with the CDRs and the mouse residues were retained at these locations in the humanized form. CDR residues in X72479 are omitted in the Figure.

FIG. 35 shows the oligonucleotides (SEQ ID NOS 91-92 and 130-143, respectively, in order of appearance) used for construction of the Hu35B6 VH gene.

FIG. 36 shows the oligonucleotides (SEQ ID NOS 107-108, 144-155 and 122-123, respectively, in order of appearance) used for construction of the Hu35B6 VL gene.

FIG. 37 shows the oligonucleotides used for construction of the Hu35B6 VH gene (full-length coding nucleotide sequence disclosed as SEQ ID NO: 67 and coded amino acid sequence disclosed as SEQ ID NO: 194). An arrow denotes the position and orientation (5' to 3') of each oligonucleotide. Amino acid residues are shown in single letter code.

FIG. 38 shows oligonucleotides used for construction of the Hu35B6 VL gene (full-length coding nucleotide sequence disclosed as SEQ ID NO: 69 and coded amino acid sequence disclosed as SEQ ID NO: 195). An arrow denotes the position and orientation (5' to 3') of each oligonucleotide. Amino acid residues are shown in single letter code.

FIG. 39 shows the nucleotide sequence of the Hu35B6 VH gene (SEQ ID NO: 68) flanked by SpeI and HindIII sites (underlined) is shown along with the deduced amino acid sequence (SEQ ID NO: 194). Amino acid residues are shown in single letter code. The signal peptide sequence is in italic. The N-terminal amino acid residue (Q) of the mature VH is double-underlined. CDR sequences according to the definition of Kabat et al. (1991) are underlined. The intron sequence is in italic.

FIG. 40 shows the nucleotide sequence of the Hu35B6 VL gene (SEQ ID NO: 70) flanked by NheI and EcoRI sites (underlined) is shown along with the deduced amino acid sequence (SEQ ID NO: 195). Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic.

Figure 41A:
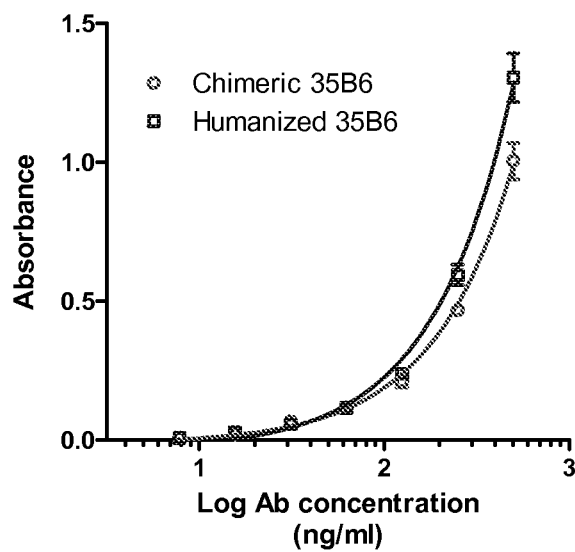
Figure 41B:
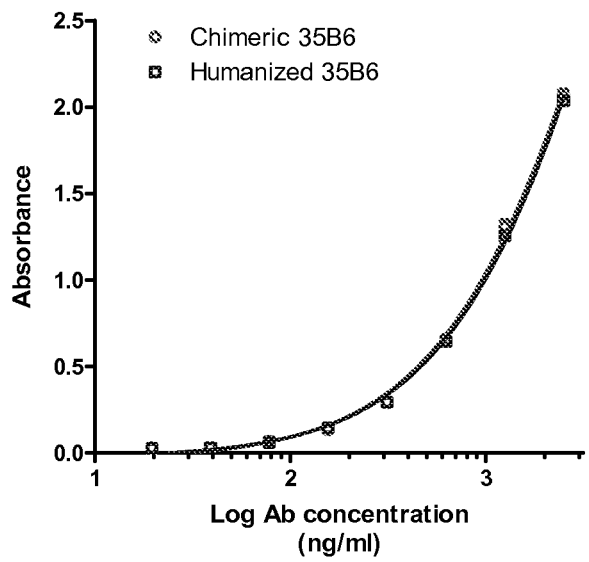

FIG. 41A-41B shows the binding of chimeric and humanized 35B6 antibodies to hOPN-BSA was analyzed by ELISA. Each antibody was tested at the starting concentration of 2.5 µg/ml (FIG. 41A) or 1.0 µg/ml (FIG. 41B) and serial 2-fold dilutions. Experiments were carried out in triplicate. The mean absorbance value with standard deviation at each antibody concentration is shown in FIG. 41A-41B.

5. DETAILED DESCRIPTION OF THE INVENTION

5.1. Preparation of Antibodies Against the RGD Sequence

Antibodies that immunospecifically recognize the RGD sequence may be generated by any suitable method known in the art.

RGD-protein or peptides which includes cell adhesive "RGD" sequence (hereinafter abbreviated as "RGD-peptides") in the present invention or may be (1) derived from human ECMs that express RGD-protein or from all tissues where these ECMs are present, (2) recombinant proteins or peptides which are obtained by expression of the DNA (preferably cDNA) encoding the RGD-protein or RGD-peptide by transfecting into bacteria, yeast, cell lines such as animal cells, etc., or (3) synthetic proteins or peptides.

The RGD-peptides used as an antigen in the present invention may be able to produce antibodies against the RGD sequence by immunization. The RGD-peptides include the RGD-peptides an amino acid sequence CVDVPNG RGDSLAYGLR (SEQ ID NO: 157) which is a cell adhesive sequence of murine ECM protein. The RGD-proteins or the RGD-peptides include such as OPN, vitronectin, fibronectin, von Willebrand Factor, collagens, laminin, tenascin, fibrinogen, thrombospondin and RGD including fragment thereof. Artificial or natural variations such as substitutions, deletions, modifications and additions of the amino acid can be applied to the said proteins or said peptides as far as the proteins or the peptides include the RGD-sequence. The variant proteins or peptides may comprise an amino acid sequence, wherein multiple amino acids, preferably 1 to 10 amino acids and more preferably 1 to several (e.g., 1 to 5) amino acids are substituted deleted, modified, added or inserted.

Herein, the RGD-peptide comprises at least about 5 amino acids, preferably about 5 to 50 amino acids, and more preferably about 10 to 20 amino acids. The RGD-proteins or the RGD-peptides as an antigen in the present invention can be produced by using methods well known in the art, such as chemical synthesis method, cell culture method, gene recombinant method and its proper modification. For example, the RGD-peptide can be obtained by cleaving ECM protein with protease appropriately. The RGD-protein or the RGD-peptide can be derived from mammal such as murine, rat, rabbit, swine, bovine, monkey and human. Any methods well known in the art can be used for preparing the RGD-protein or the RGD-peptide which can be used for preparing an anti-RGD antibody.

Examples of the methods for producing variant polypeptides include a synthetic oligonucleotide site-directed mutagenesis (gapped duplex method), a point mutagenesis method which involves introducing a point mutation at random by treatment with nitrite or sulfite, a method which involves preparing a deletion mutant with Ba131 enzyme, or other enzymes, a cassette mutagenesis, a linker scanning method, a miss incorporation method, a mismatch primer method, a DNA segment synthesis method, and the like.

The RGD-peptide can be bound with other biologic macromolecule such as thyrogloblin, Keyhole Limpet Haemocyanin (KLH), bovine serum albumin (BSA), ovalbumin (OVA) or bovine globulin, preferably thyrogloblin. The method for binding RGD-peptide to a biologic macromolecule may be achieved by using coupling reagent such as a binding reagent having active ester group and maleic imide group (the active ester group binds to amino group of a protein or a peptide and the maleic imide group binds to thiol group of a protein or a peptide; S. Yoshirake et al., Eur. J. Biochem., 101, 395-399, 1979), by using mixed anhydride method (B. F. Erlanger et al., J. Biol. Chem., 234, 1090-1094, 1954), or by using active ester method (A. E. Kant et al., J. Agric. Food Chem., 42, 301-309, 1994). The method for binding RGD-peptide to a biologic macromolecule is preferably achieved by using coupling reagent.

As an antigen, a cell per se that overexpresses the RGD-protein or the RGD-peptide can be also used. Cells overexpressing the RGD-protein or the RGD-peptide may be prepared by recombinant DNA technologies well known in the art.

Using appropriate antigens prepared as described above, antibodies specific for the RGD sequence may be prepared by various methods well known in the art. Polyclonal antibodies to the RGD sequence can be produced by various procedures well known in the art. For example, an antigen of interest can be administered to various host animals including, but not limited to, rabbits, mice, rats, etc., to induce the production of antisera containing polyclonal antibodies specific for the antigen. Various adjuvants may be used to increase the immunological response, depending on the host species, which include but are not limited to, Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*. Such adjuvants are also well known in the art.

Monoclonal antibodies can be prepared by using a wide variety of techniques known in the art including the use of hybridoma, recombinant and phage display technologies, or a combination thereof. For example, monoclonal antibodies can be produced by using hybridoma techniques including those known in the art and taught in, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated by reference in their entirety). The term "monoclonal antibody" as used herein is not limited to antibodies produced through hybridoma technology. The term "monoclonal antibody" refers to an antibody derived from a single clone, and includes any eukaryotic, prokaryotic or phage clone, but not limited to the method it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells (e.g., P3U1, P3X63-Ag8, P3X63-Ag8-U1, P3NS1-Ag4, SP2/0-Ag14, P3X63-Ag8-653, etc.). Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments what recognize specific epitopes may be generated by known techniques. For example, Fab and $F(ab')_2$ fragments may be produced by proteolytic cleavage of immunoglobulin molecules, using enzymes such as papain (to produce Fab fragments) or pepsin (to produce $F(ab')_2$ fragments). $F(ab')_2$ fragments contain the complete L-chain, and the V-region, the CH1 region and the hinge region of the H-chain.

The antibodies of the invention or an antigen-binding fragment thereof may be produced by any method known in the art for synthesis of antibodies, in particular, by chemical synthesis or preferably by recombinant expression techniques.

The nucleotide sequence encoding an antibody may be obtained from any information available to those skilled in the art (i.e., from Genbank, the literature, or by routine cloning and sequence analysis). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A+RNA, isolated from any tissue or cells expressing the antibody, such as hybridoma cells selected to express an antibody) by PCR amplification using synthetic primers hybridizable to the and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

5.2. Preparation of Recombinant Antibodies

The nucleotide sequence of the antibody may be manipulated by using methods well known in the art for the manipulation of nucleotide sequences, e.g., recombinant DNA techniques, site directed mutagenesis, PCR and the like (see, for example, the techniques described in Sambrook et al., supra; and Ausubel et al., eds., 1998, Current Protocols in Molecular Biology, John Wiley & Sons, NY, which are both incorporated by reference herein in their entirety). Antibodies may be introduced mutations such as substitutions, deletions and/or insertions of amino acid at epitope-binding domain regions or at any portion to enhance or reduce biological activities.

An expression vector containing a nucleotide sequence that encodes the antibody can be used for recombinant expression of an antibody or an antigen-binding fragment thereof. The vector including a nucleotide sequence encoding an antibody molecule, a H-chain and/or a L-chain of an antibody or a portion thereof for production of the antibody or an antigen-binding fragment thereof may be produced by recombinant DNA technology using techniques well known in the art as discussed in the previous sections. Methods which are well known to those skilled in the art can be used to construct expression vectors containing antibody or an antigen-binding fragment thereof coding sequences and appropriate transcriptional and translational control signals. These methods include, for example, in vitro recombinant DNA techniques, synthetic techniques, and in vivo genetic recombination. The nucleotide sequence encoding the VH, the VL, both of the VH and the VL, an antigen-binding fragment of the VH and/or VL, or one or more CDRs of an antibody may be cloned into such a vector for expression. Such a sequence may be fused with a polynucleotide encoding a signal peptide which may be native or a heterologous to the original antibody. The expression vector thus-prepared can be then introduced into appropriate host cells for the expression of the antibody. Accordingly, the invention includes host cells containing a polynucleotide encoding a humanized antibody or an antigen-binding fragment thereof that immunospecifically recognizes the RGD sequence.

The host cell may be co-transfected with two expression vectors of the invention, wherein the first vector encodes a H-chain derived polypeptide and the second vector encodes a L-chain derived polypeptide. The two vectors may contain identical selectable markers which enable equal expression of H-chain and L-chain polypeptides or different selectable markers to ensure maintenance of both plasmids. Alternatively, a single vector may be used which encodes, and is capable of expressing, both of H-chain and L-chain polypeptides. The coding sequences for the H-chain and L-chain may comprise cDNA or genomic DNA.

In another embodiment, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phages used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., J. Immunol. Methods, 182:41-50, 1995; Ames et al., J. Immunol. Methods, 184:177-186, 1995; Kettleborough et al., Eur. J. Immunol., 24:952-958, 1994; Persic et al., Gene, 187:9-18, 1997; Burton et al., Advances in Immunology, 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques, 12(6):864-869, 1992; and Sawai et al., AJRI, 34:26-34, 1995; and Better et al., Science, 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., Methods in Enzymology, 203:46-88, 1991; Shu et al., PNAS, 90:7995-7999, 1993; and Skerra et al., Science, 240:1038-1040, 1988.

Once an antibody molecule of the invention has been produced by any methods described above, it may then be purified by any method known in the art for purification of an immunoglobulin molecule, for example, by chromatography (e.g., ion exchange, affinity, particularly by affinity for the specific antigen after Protein A or Protein G purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

For some uses, including in vivo use of antibodies in humans and in vitro detection assays, it may be preferable to use chimeric, humanized, or human antibodies. Chimeric antibodies and humanized antibodies are discussed in details in Section 5.3, infra.

Antibodies fused or conjugated to other compounds or heterologous polypeptides may be used in in vitro immunoassays, in purification methods (e.g., affinity chromatography), as well as in vivo therapeutic or diagnostic uses. See e.g., PCT publication Number WO 93/21232; EP 439,095; Naramura et al., Immunol. Lett., 39:91-99, 1994; U.S. Pat. No. 5,474,981; Gillies et al., PNAS, 89:1428-1432, 1992; and Fell et al., J. Immunol., 146:2446-2452, 1991, which are incorporated herein by reference in their entirety. For example, antibodies can be labeled in various ways using a known method or commercially available kit (e.g., biotin labeling, FITC labeling, APC labeling). As another example, antibodies may be conjugated to a therapeutic moiety that enhances the biological effect of the antibodies in vivo. Examples of such a therapeutic moiety include another antibody, cytotoxins that are cytostatic or cytocidal, radioactive element, and/or other therapeutic agents, including anti-inflammatory agents, antibiotics, and the like. In the present invention, the humanized anti-RGD antibody may be conjugated to another antibody to form a bispecific antibody. As another example, the humanized antibody of the present invention may be labeled with detectable markers, such as radioactive elements, for in vivo diagnostic uses.

5.3. Chimeric and Humanized Antibodies

A chimeric antibody is a molecule in which different portions of the antibody are derived from different animal species, such as antibodies having a V-region derived from a murine monoclonal antibody and a constant region derived from a human immunoglobulin. Methods for producing chimeric antibodies are known in the art. See e.g., Morrison, Science, 229:1202, 1985; Oi et al., BioTechniques, 4:214 1986; Gillies et al., J. Immunol. Methods, 125:191-202, 1989; U.S. Pat. Nos. 5,807,715; 4,816,567; and 4,816,397, which are incorporated herein by reference in their entirety.

A humanized antibody is a molecule that binds a desired antigen and comprises a V-region containing one or more CDRs derived from a non-human species and one or more FRs derived from a human immunoglobulin molecule. The typical methods for humanizing non-human antibodies have been described in various references, such as those: by Queen et al., 1989, Proc. Natl. Acad. Sci. USA 86:10029-10033 and U.S. Pat. Nos. 5,585,089 and 5,693,762; by Riechmann et al., Nature, 332:323, 1988; and by Tsurushita et al., Methods 36:69-83, 2005, all of which are incorporated herein by reference in their entirety). For example, the reference by Tsurushita et al. (2005, supra; hereafter "Tsurushita") provides a practical and instructive protocol for the humanization of mouse monoclonal antibodies based on the antibody-humanization method originally developed by Queen et al. (1989, supra). The general protocol disclosed in Tsurushita is briefly summarized below.

5.3.1. General Protocol for Preparing Humanized Antibodies

Cloning and Sequencing of Mouse V Genes

Various methods are available for cloning cDNAs encoding the VH and the VL of a target mouse monoclonal antibody. For example, 5' RACE (rapid amplification of cDNA ends) method using SMART RACE cDNA Amplification Kit (BD Biosciences, CA) or the GeneRacer Kit (Invitrogen, CA) has been commonly used. A gene-specific primer for 5' RACE can be prepared based on the isotypes of the H-chain and the L-chain of the target monoclonal antibody so that it can bind immediately downstream of the VH and VL. Thus, 5' RACE primer may be designed to be specific for each subtype in mouse, such as γ1, γ2a, γ2b or γ3. Alternatively, a common primer for all subtypes may be designed based on the consensus or highly homologous region among the subtypes. In Tsurushita, the following 5' RACE primers are disclosed as examples:

```
                                          (SEQ ID NO: 82)
(i) 5'-GCCAGTGGATAGACTGATGG-
(for cloning of mouse γ1, γ2a, γ2b and γ3 H-chains)
                                          (SEQ ID NO: 83)
(ii) 5'-GATGGATACAGTTGGTGCAGC-
(for cloning of mouse K L-chains).
```

PCR-amplified V-region gene fragments can be directly cloned into a plasmid vector, for example, using the Zero Blunt TOPO PCR Cloning Kit (Invitrogen), and their DNA sequences determined. The obtained sequences should be confirmed by, for example, comparing their encoding amino acid sequences with those of the target monoclonal antibody determined by the N-terminal amino acid sequencing, using, for example a Model 241 Protein Sequencer (Hewlett-Packard, CA). Typically, the determination of at least 15-20 amino acid residues at the N-terminus of the target antibody, for example, by Edman degradation, is sufficient to confirm the authenticity of the cloned DNA sequences. Tsurushita cautions that when glutamine, which is one of the two most common N-terminal amino acid in mouse, is the N-terminal amino acid, it might have been converted to pyroglutamine and blocks the sequencing at the N-terminus. In that case, it is necessary to deblock the N-terminus to obtain the sequence.

Three-Dimensional Modeling of V-Regions

Based on the sequences of the VH and the VL, the framework residues of the target antibody that are potentially important for maintaining the conformational structure of the CDRs, are first identified by the method, for example, described by R. Levy et al., 1989, *Biochemistry* 28:7168-7175; and by B. Zilber et al., 1990, *Biochemistry* 29:10032-10041. Typically, each of the VH and VL is divided into 14 structurally meaningful segments, which are β strands and loop-like structures comprising the domain structure of the immunoglobulin superfamily. The amino acid sequence of each of the segments from the target antibody is aligned with the corresponding segments of antibodies of known structures, in the PDB database (see H. M. Berman et al., 2000, *Nucleic Acids Res.* 28:235-342). By multiple sequence alignment, a corresponding segment having the highest sequence homology to each of the target segment is selected and the three-dimensional model of the V-region is constructed. In order to optimize the structure, the model is subjected to multiple cycles of conjugate gradient energy minimization (e.g., using ENCAD, or as described by Press et al., 1990, in "*Numerical Recipes*, Cambridge University Press, Cambridge; AMBER by Weiner et al., 1981, *J. Comp. Chem.* 2:287-303; 3D-JIG-SAW available at BioMolecularModelling or "BMM" web site run by Cancer Research UK; or SWISS-MODEL available at ExPASy Proteomics Server web site run by Swiss Institute of Bioinformatics, Geneva).

Selection of Human Frameworks

In parallel with modeling the structure of the V-regions, the amino acid sequences deduced from the cDNA cloning of the mouse VH and VL, respectively, are compared to human V-region sequences in the databases, for example, the Kabat database (see Johnson et al., 2000, *Nucleic Acids Res.* 28:214-218.), GenBank, and so forth. Human FRs that have overall sequence identity of at least about 65%, at least about 70%, at least about 75%, at least about 80%, at least about 85%, at least about 90%, or at least 95% identity, with the mouse sequence, can be searched using, for example, the Smith-Waterman algorithm (by Gusfield, 1997, in "*Algorithms on Strings, Trees, and Sequences*", Cambridge University Press, Cambridge), or BLAST (by Karlin et al., 1990, *Proc. Natl. Acad. Sci. USA* 87:2264-2268), and the like. These human sequences may be based on cDNA-based and protein-derived sequences; however, the use of germline is often preferable as it may be useful in eliminating potential immunogenicity associated with somatic hypermutations in cDNA-based, protein-derived sequences. In the alternative, as described in Queen et al. (1989, supra), the use of a consensus framework sequence can also identify and remove such hypermutated residues in the framework obtained from cDNA-based or protein-derived sequences. In the case where a germline VH segment is used as an acceptor framework, VH segments encoded on chromosome 14, rather than 15 and 16, should be used as only those on chromosome 14 produce functional VH.

Design of Humanized V-Regions

According to Queen et al. (1989, supra), it is necessary to identify framework amino acids within about 4-6 Å of the CDRs as these residues are considered to be potential key framework residues that support the correct CDR structures. Such a process can be achieved using a computer program, such as RASMOL available at Molecular Visualization Freeware web site supported by National Science Foundation (NSF), that calculates interatomic distances from the atomic coordinates or, through manual inspection of a computer model. If amino acids at key framework positions are different between mouse donor and human acceptor sequences, those of mouse donor usually replace the human residues. However, if such residues have minimal contribution to support the CDR structures, the corresponding human residues are typically used. Also, if the selected human acceptor contains "atypical" amino acids, which occur in less than about 10-20% of the V region sequences, they may be the result of somatic hypermutation during affinity maturation and should be replaced with the donor residues in order to avoid potential immunogenicity in humans.

In addition, other factors, such as residues of potential N-linked glycosylation signals, need to be carefully considered in order to design humanized V regions (see Tsurushita for details).

Humanized antibodies may contain a human constant region or a portion thereof from the human κ or λ L-chain, and/or the γ1, γ2, γ3, γ4, μ, α1, α2, δ, or ε H-chain of human antibodies, or variants thereof, depending on the effector functions required or to be eliminated for therapeutic uses. For example, a Fc portion of the constant region containing a mutation may be fused to the V-region of the chimeric or humanized antibody of the present invention so as to reduce the binding of the antibody to Fc receptors and/or to reduce its ability to fix complement (see, for example, Winter et al., GB 2,209,757 B; Morrison et al., WO 89/07142, Morgan et al., WO 94/29351). Such manipulations of antibody molecules can be carried out by recombinant DNA technology as described in Section 5.2.

Preferably the resulting chimeric or humanized antibody has the same specificity as the non-human donor antibody and an affinity similar to or at least about ⅓, at least about ½, or at least about ⅔, of that of the non-human donor antibody. In another aspect, the resulting chimeric or humanized antibody has an affinity constant of at least about $1 \times 10^7$ $M^{-1}$, preferably at least about $1 \times 10^8$ $M^{-1}$, and most preferably at least about $1 \times 10^9$ $M^{-1}$.

In addition to the general protocol described above, antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592, 106; EP 519,596; Padlan, Molecular Immunology, 28(4/5): 489-498, 1991; Studnicka et al., Protein Engineering, 7(6): 805-814, 1994; Roguska et al., Proc Natl. Acad. Sci. USA, 91:969-973, 1994), and chain shuffling (U.S. Pat. No. 5,565, 332), all of which are hereby incorporated by reference in their entirety.

5.3.2. Additional Considerations for Preparing Humanized Antibodies as Pharmaceuticals To offer humanized antibodies as pharmaceuticals, an efficient and consistent production system therefore needs to be prepared. For example, an appropriate expression vector for humanized antibodies is prepared by inserting H-chain and L-chain sequences, and a high-productivity cell line transfected with the expression vector can be obtained as a seed cell for a master cell bank (MCB), which serves as a stable and semi-permanent source for a working cell bank (WCB). Humanized antibodies can be then prepared by culturing working cells from the WCB and collecting the culture medium.

Various expression vectors with appropriate regulatory genes can be used for the preparation of such a production cell line. As a host cell, those commonly used for expressing mammalian proteins can be used for the expression of humanized antibodies. Examples of such host cells include, but are not limited to, Chinese Hamster Ovary (CHO) cells, SP2/0-Ag14.19 cells, NS0 cells, and the like. The productivity of humanized antibodies can be maximized by selecting the best combination of an expression vector and a host cell. Furthermore, the composition of culture media should be explored in order to select suitable media, from various serum-free culture media and supplements, so that the expression of humanized antibodies by the host cell can be optimized.

Based on the efficiency and the final yield, the humanized antibodies produced by the host cell can be purified from the culture supernatant using various methods well known in the art, including affinity chromatography, ion-exchange chromatography, hydrophobic interaction chromatography, and the like.

5.4. Pharmaceutical Composition and Therapeutic Uses

The present invention provides a pharmaceutical composition comprising the humanized antibody or an antigen-binding fragment thereof, described above, that immunospecifically recognizes the RGD sequence. The pharmaceutical composition comprising the humanized antibody of the present invention as an active ingredient can be used as an agent for preventing and/or treating a disorder or disease that is associated with RGD proteins, including, but not limited to, cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like.

The pharmaceutical composition comprising the humanized antibody of the present invention can also be used to treat chronic rejection after organ transplantation, and an autoimmune disease such as systemic autoimmune disease, erythematosus, uveitis, Behcet's disease, polymyositis, glomerular proliferative nephritis, sarcoidosis, and the like.

The preventive and/or therapeutic agent for preventing or treating the disorders or diseases described above, comprising the humanized antibody of the present invention, has low toxicity and can be administered to humans orally or parenterally, directly as a liquid preparation by mixing in a suitable solvent, or as a pharmaceutical composition in an appropriate dosage form.

The pharmaceutical composition used for the administration described above contains the aforesaid antibody or salts thereof and pharmaceutically acceptable carriers, diluents or excipients. Such a composition is provided in a dosage form suitable for oral or parenteral administration.

The dose may vary depending upon the age and the size of a subject to be administered, target disease, conditions, route of administration, and the like. When the antibody is used for preventing and/or treating, for example, rheumatoid arthritis in an adult patient, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu and Wu, 1987, J. Biol. Chem. 262:4429 4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, by means of nasal spray, or by means of an implant, said implant being of a porous, non porous, or gelatinous material, including membranes, such as sialastic membranes, or fibers. In one embodiment, administration can be by direct injection at the site (or former site) infected tissues.

In another embodiment, the pharmaceutical composition can be delivered in a vesicle, in particular a liposome (see Langer, 1990, Science 249:1527-1533; Treat et al., in Liposomes in the Therapy of Infectious Disease and Cancer, Lopez Berestein and Fidler (eds.), Liss, New York, pp. 353-365 (1989); Lopez-Berestein, ibid., pp. 317-327; see generally ibid.).

In yet another embodiment, the pharmaceutical composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

Examples of the composition for oral administration include solid or liquid dosage forms, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, and the like.

The injectable preparations may include dosage forms for intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage form in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibodies described above.

The present invention also relates to an inhibitor and/or promoter for cell and/or tissue remodeling, which comprises an RGD sequence-binding functional molecule (e.g., integrins, etc.) as an active ingredient; and a method for inhibiting and/or promoting cell and/or tissue remodeling, which comprises contacting the RGD protein expressing cell and/or tissue (e.g., a tumor cell, neutrophil, smooth muscle, etc.) with the RGD protein binding functional molecule. The dose, method for administration, pharmaceutical preparation, etc. of the active ingredient in such a therapeutic agent can be appropriately determined by referring to the foregoing description of medicaments comprising the humanized antibodies of the present invention.

As described above, the present invention further provides a method for preventing or treating a disorder or disease that is associated with or involves RGD proteins, said method comprising administering an effective amount of at least one of the humanized antibodies of the present invention to a subject in need thereof.

5.5. Diagnostic Uses

The pharmaceutical composition comprising the humanized antibody of the present invention can be used as a diagnostic agent for cancer, (e.g., the growth or metastasis of cancer cells) and/or an inflammatory disease (e.g., rheumatoid arthritis, osteoarthritis, hepatitis, bronchial asthma, fibrosis, diabetes mellitus, arteriosclerosis, multiple sclerosis, granuloma, etc.), or as a diagnostic agent for chronic rejection after organ transplantation, an autoimmune disease such as systemic autoimmune disease, erythematosus, uveitis, Behcet's disease, polymyositis, glomerular proliferative nephritis, sarcoidosis, and so forth. The humanized antibodies of the present invention are capable of specifically recognizing the RGD sequence and hence can be used to quantify the RGD proteins in a test fluid, especially for quantification by the sandwich immunoassay, competitive assay, immunometry, nephrometry, etc., immunostaining, or the like. In applying these immunological methods to the assay methods of the present invention, it is not required to set forth any particular conditions, procedures, etc. It is sufficient to construct assay systems by adding ordinary technical consideration in the art to conventional conditions and procedures. For details of these general technical means, reference can be made to reviews, texts or the like.

As described above, the RGD proteins may be quantified with high sensitivity by using the antibodies of the present invention. The humanized antibodies of the present inventions are particularly useful for diagnosing various diseases associated with the RGD proteins by applying the method for quantifying the RGD proteins in vivo. For instance, where an increase or decrease in the expression level of the RGD proteins is detected, it can be diagnosed that it is highly likely that one now suffers from diseases associated with the RGD protein, e.g., cancer or an inflammatory disease, or it is highly likely that one will suffer from these diseases in the future. Thus, the present invention also provides a method for diagnosing a disorder or disease associated with or involve the RGD proteins in a subject, said method comprising administering an effective amount of at least one of the humanized antibodies of the present invention or both to a subject in need thereof. Required dosages for such an in vivo diagnosis may be less than those required for therapeutic uses and can be determined by one skilled in the art according to routine procedures.

The humanized antibodies of the present invention can also be used for specifically detecting the RGD proteins present in a test fluid such as a body fluid, a tissue, etc. The humanized antibodies can also be used for preparation of antibody columns for purification of the RGD proteins, for detection of the RGD proteins contained in each fraction upon purification or for analysis of behaviors of the RGD proteins in cells to be tested.

6. EXAMPLES

The following examples illustrate preparation of monoclonal antibodies that immunospecifically recognize the RGD sequence, sequencing of the V-regions of the monoclonal antibodies, epitope mapping and other characterization of the antibodies and chimerization and the humanization of such antibodies, as well as the characterization of the resulting chimeric and humanized antibodies. These examples should not be construed as limiting the scope of the invention.

6.1. Preparation of Mouse Antibody Against the RGD Sequence

Mouse monoclonal antibodies against the RGD sequence were prepared according to the subtractive immunization method (by Williams C. V., et al., 1992, *Biotechniques* 12:842-847). Antigen was prepared as a synthetic peptide of an amino acid sequence CVDVPNGRGDSLAYGLR (SEQ ID NO: 157) which includes the RGD sequence and an amino acid sequence SLAYGLR (SEQ ID NO: 158) which are cell adhesive sequence of ECM protein. The antigen peptide was coupled to thyroglobulin via EMCS (Dojin), which was immunized to mice as antigen with adjuvant. Hybridomas were prepared by the methods well known in the art (see, for example, Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981). After 4 times immunization, splenic cells were collected and fused with myeloma cell X63-Ag8-653. Then hybridoma clones producing monoclonal antibodies that were immunospecifically reactive with RGD sequence were selected by using HAT medium and by screening of culture supernatant with ELISA (antigen peptide solid phase). Eight hybridoma clones 4P11, 11M6, 25H15, 29R5, 30C17, 33E10, 35B6 and 38I8 were established as hybridoma clones producing monoclonal antibodies immunospecifically recognizing RGD sequence were isolated. Antibodies were purified form supernatant of the hybridoma by using antigen peptide column prepared by using thiol sepharose beads (Amasham Bioscience).

6.2. Epitope Analysis for Anti-the RGD Sequence Monoclonal Antibodies

Peptides of amino acid sequence of CLPVKTDSGS-SEEKLY (mOPN1) (SEQ ID NO: 159), CVDVPNGRGD-SLAYGLR (mOPN5) (SEQ ID NO: 157), CVDVPNGRGDS (SEQ ID NO: 160), CPNGRGD (SEQ ID NO: 161), CGRGDSLAYGLR (SEQ ID NO: 162) CGDSLAYG (SEQ ID NO: 163), CGDSLAYGLR (SEQ ID NO: 164) and CSLAYGLR (SEQ ID NO: 165) which include murine OPN derived partial peptide, a peptide of amino acid sequence CVDTYDGRGDSVVYGLRS (SEQ ID NO: 166) and CSV-VYGLR (SEQ ID NO: 167) which include human OPN derived partial peptide, and a peptide of amino acid sequence CGRGDS (SEQ ID NO: 168) which include common peptide sequence of human OPN and murine OPN were coupled to BSA (Sigma corporation) via EMCS (Dojin) and used for ELISA.

A 96 well plate was immobilized with peptides (10 μg/ml) or proteins (5 μg/ml) by cultivating at 37° C. for an hour, blocked with 0.1% BSA/PBS/0.05% NaN$_3$ solution, and then reacted with various concentrations of antibodies at 37° C. for an hour. Next, the plate was reacted with HRP labeled anti-murine IgG antibody (Jackson ImmunoResearch Laboratories, Inc.) as secondary antibody at 37° C. for 30 minutes, added OPD as chromogen, added 1N H$_2$SO$_4$ to stop the reaction, and then detected absorbance at 490 nm.

As shown in FIG. 1, FIG. 2, FIG. 3, FIG. 4 and FIG. 5, monoclonal antibodies 4P11, 11M6, 25H5, 35B6 and 33E10 bind to mOPN5 and hOPN5, and recognize murine and human partial peptide of RGD protein. Monoclonal antibody 33E10 recognized GRGDS (SEQ ID NO: 169), VDVPN-GRGDS (SEQ ID NO: 170) and PNGRGD (SEQ ID NO: 171), but not SLAYGLR (SEQ ID NO: 158) or SVVYGLR (SEQ ID NO: 172) which includes a sequence following RGD of OPN. Monoclonal antibody 33E10 recognizes the RGD sequence commonly included in GRGDS (SEQ ID NO: 169), VDVPNGRGDS (SEQ ID NO: 170) and PNGRGD (SEQ ID NO: 171) and is able to bind to both human and murine peptides. Monoclonal antibody 35B6 recognized GRGDSLAYGLR (SEQ ID NO: 173), GDSLAYG (SEQ ID NO: 174) and GDSLAYGLR (SEQ ID NO: 175), but not GRGDS (SEQ ID NO: 169), VDVPNGRGDS (SEQ ID NO: 170) or PNGRGD (SEQ ID NO: 171). Monoclonal antibody 35B6 recognizes the sequence following the RGD including GD. Monoclonal antibodies 29R5, 30C17 and 38I8 were slightly reactive with GRGDS (SEQ ID NO: 169), SLAYGLR (SEQ ID NO: 158) and SVVYGLR (SEQ ID NO: 172), but only react with mOPN5—indicating that these monoclonal antibodies recognize VDVPNGRGDSLAYGLR (SEQ ID NO: 176) of murine OPN.

6.3. CDR Analysis of Anti-RGD Antibodies

The amino acid sequences of CDRs of monoclonal antibodies 33E10 and 35B6 were determined by following procedures. RNAs were extracted using RNeasy Mini kit (Qiagen) from the corresponding hybridomas and cDNAs were prepared using First-strand cDNA synthesis kit. H-chain cDNA of the antibody was extended by PCR using Heavy primer amplification kit (Amasham Bioscience), cloned into pCRII-TOPO vector (invitrogen), and then the cDNA sequence and the amino acid sequence were determined. The CDR was determined by ABG: Directory of 3D structures of antibodies (http://www.ibt.unam.mx/vir/structure/structures.html). The CDRs of V-chain and L-chain are as follows (also shown in FIG. 6 and FIG. 7).

```
(H-chain)
[CDRH1]
33E10: GFTFTDYYMI            (SEQ ID NO: 1)

35B6:  GYTFTNYWMH            (SEQ ID NO: 7)

[CDRH2]
33E10: WLGFIRNKANGYTTEYSASVKG (SEQ ID NO: 2)

35B6:  WIGNINPRNGDSNYNEKFRS   (SEQ ID NO: 8)
```

-continued

[CDRH3]
33E10: GAY                              (SEQ ID NO: 3)

35B6:  GYFDV                            (SEQ ID NO: 9)

(L-chain)
[CDRL1]
33E10: RSSQSIVHSNGNTYLE                 (SEQ ID NO: 4)

35B6:  KASQDINSYLS                      (SEQ ID NO: 10)

[CDRL2]
33E10: RVSNRFS                          (SEQ ID NO: 5)

35B6:  RANRLVD                          (SEQ ID NO: 11)

[CDRL3]
33E10: GSFVPW                           (SEQ ID NO: 6)

35B6:  YDEFPF                           (SEQ ID NO: 12)

In the present example, CDRs were determined by ABG. However, it is well known in the art that other programs may be used for determining the CDRs and may result in different sequences to some extent.

6.4. Binding Ability to ECM Protein Having RGD Sequence

Each of a human OPN (hOPN) or a murine OPN (mOPN) was purified from culture supernatant of CHO-K1 cells introduced hOPN gene or mOPN gene respectively by using anti-OPN antibody column. A human vitronectin (hereinafter abbreviated as "VN") was obtained by AGC TECHNO GLASS Co., Ltd. A human fibronectin (hereinafter abbreviated as "FN"), human thrombospondin and murine laminin were obtained from Sigma Corporation.

Binding ability of the monoclonal antibodies 33E10 and 35B6 to ECM proteins was detected by ELISA using 96 well plate immobilized with hOPN, mOPN, FN, VN or laminin obtained above. A 96 well plate was immobilized with peptides (10 μg/ml) or proteins (5 μg/ml) by cultivating at 37° C. for an hour, blocked with 0.1% BSA/PBS/0.05% $NaN_3$ solution, and then reacted with various concentrations of antibodies at 37° C. for an hour. Next, the plate was reacted with HRP labeled anti-murine IgG antibody (Jackson ImmunoResearch Laboratories, Inc.) as secondary antibody at 37° C. for 30 minutes, added OPD as chromogen, added 1N $H_2SO_4$ to stop the reaction, and then detected absorbance at 490 nm.

Figure 1:
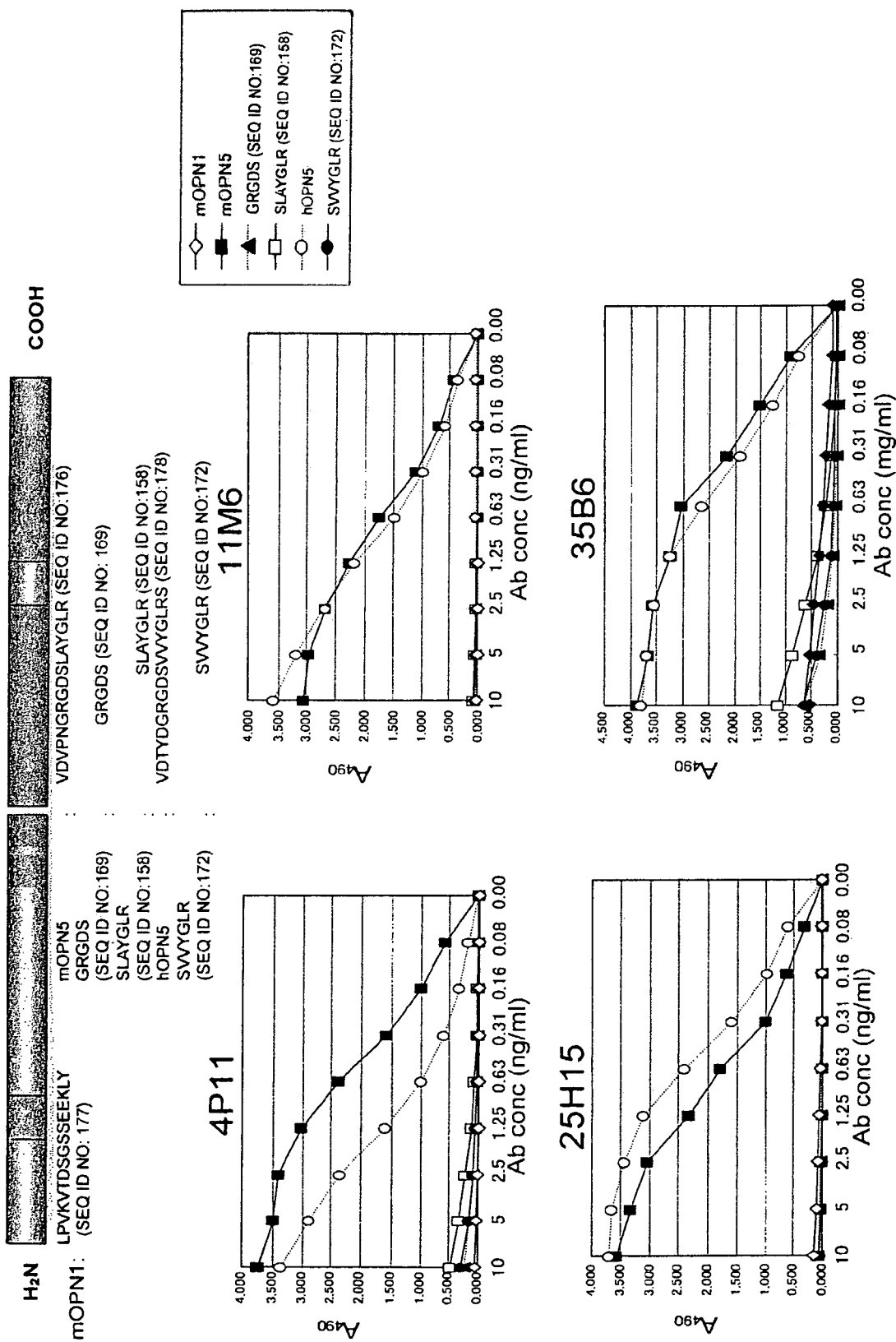
FIG. 1 shows the result of epitope analysis of monoclonal antibodies 4P11, 11M6, 25H15 and 35B6 by using partial peptides of murine OPN.
Figure 2:
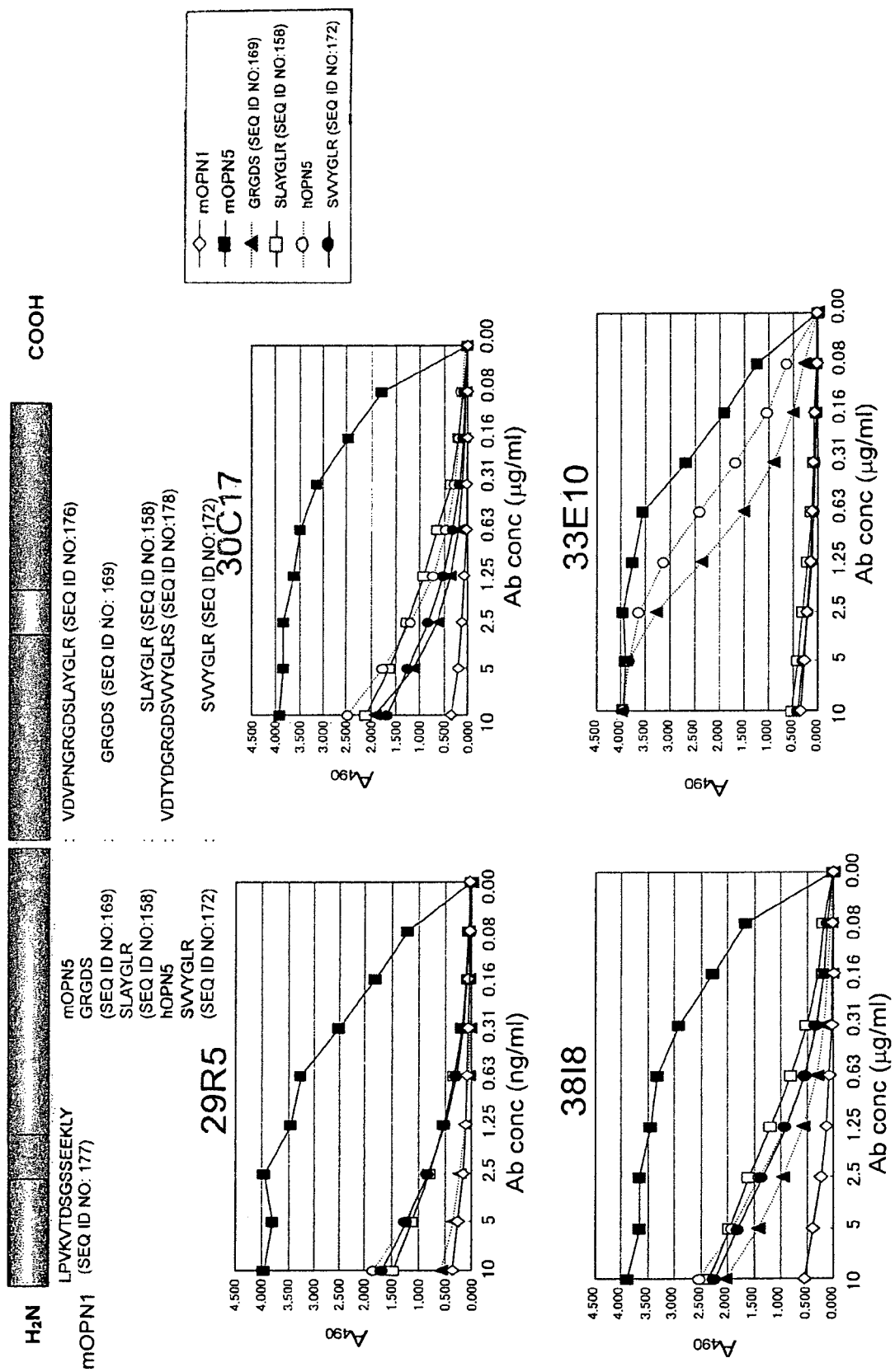
FIG. 2 shows the result of epitope analysis of monoclonal antibodies 29R5, 30C7, 33E10 and 38I8 by using partial peptides of murine OPN and human OPN.
Figure 3:
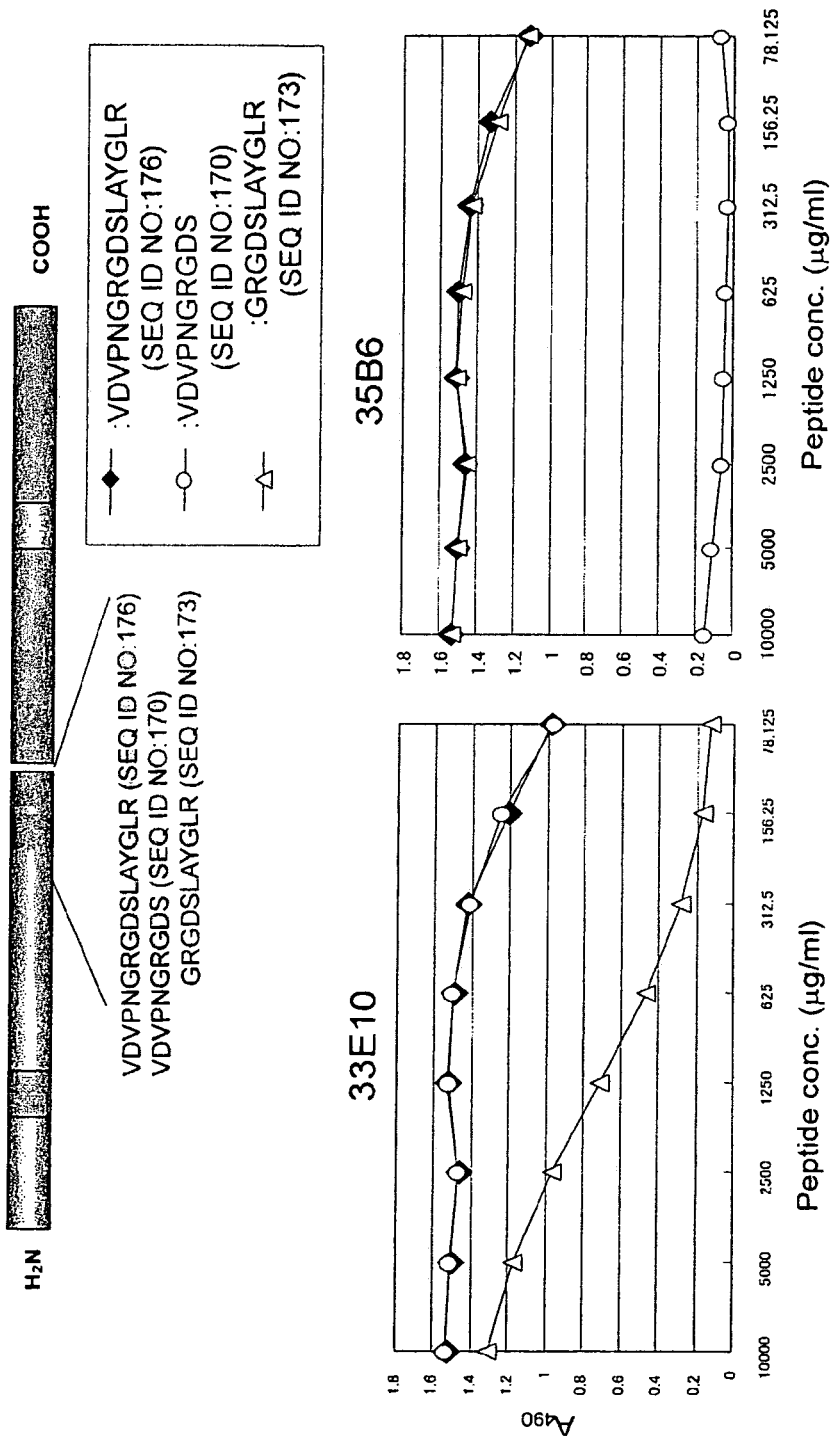
FIG. 3 shows the result of epitope analysis of monoclonal antibodies 33E10 and 35B6 by using partial peptides of murine OPN which include the RGD sequence.
Figure 4:
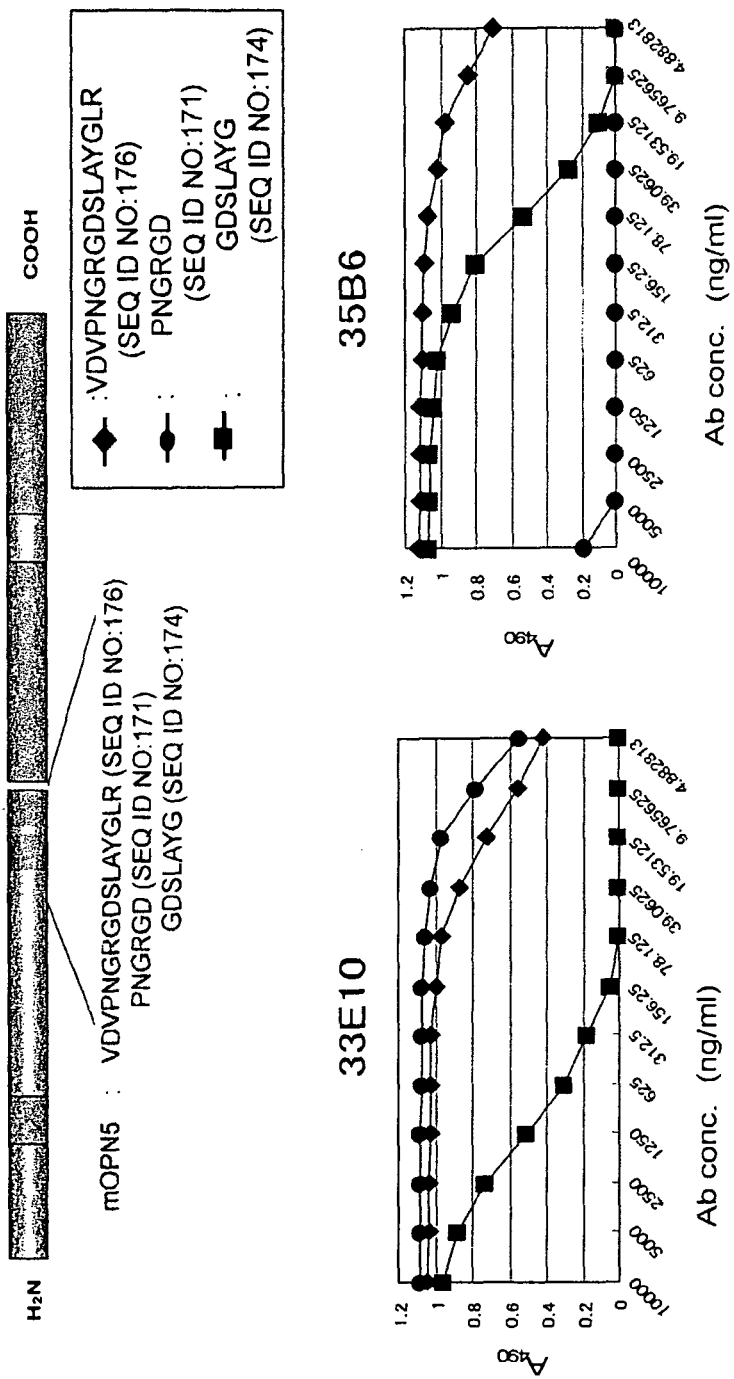
FIG. 4 shows the result of epitope analysis of monoclonal antibodies 33E10 and 35B6 by using partial peptides of murine OPN.
Figure 5:
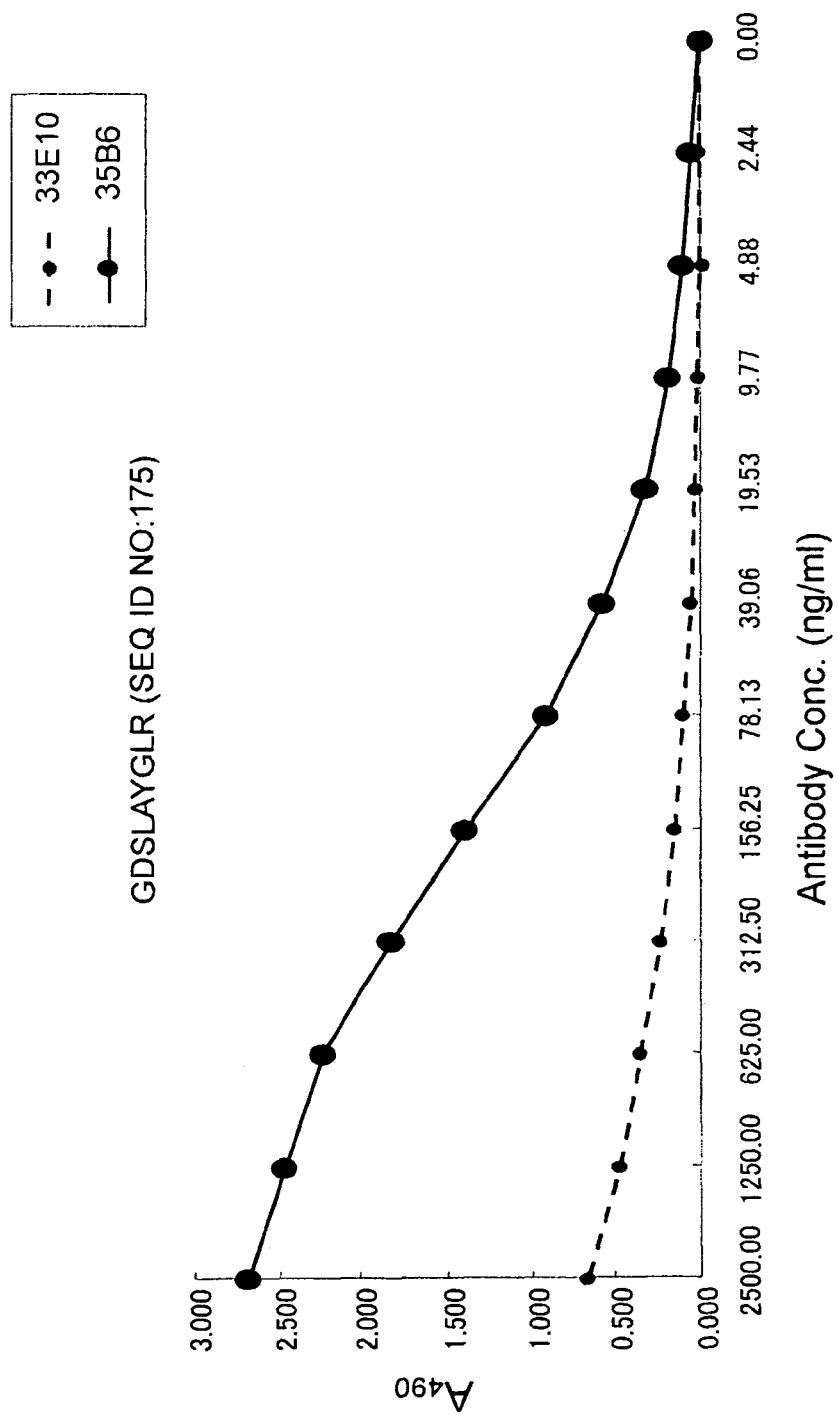
FIG. 5 shows the result of epitope analysis of monoclonal antibodies 33E10 and 35B6 by using partial peptides of murine OPN (CGDSLAYGLR; SEQ ID NO 156, FIG. 5. discloses "GDSLAYGLR" as SEQ ID NO: 175).
Figure 8:
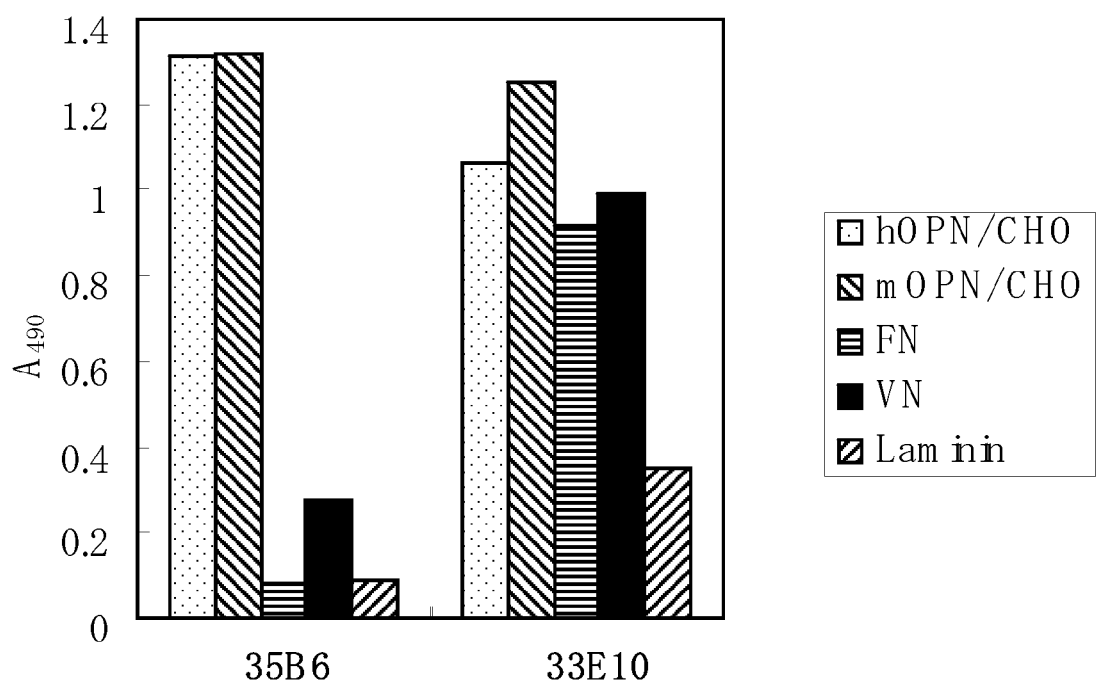
FIG. 8 shows the result of binding affinity of anti RGD antibodies with various ECM proteins which include the RGD sequence.
Figure 9:
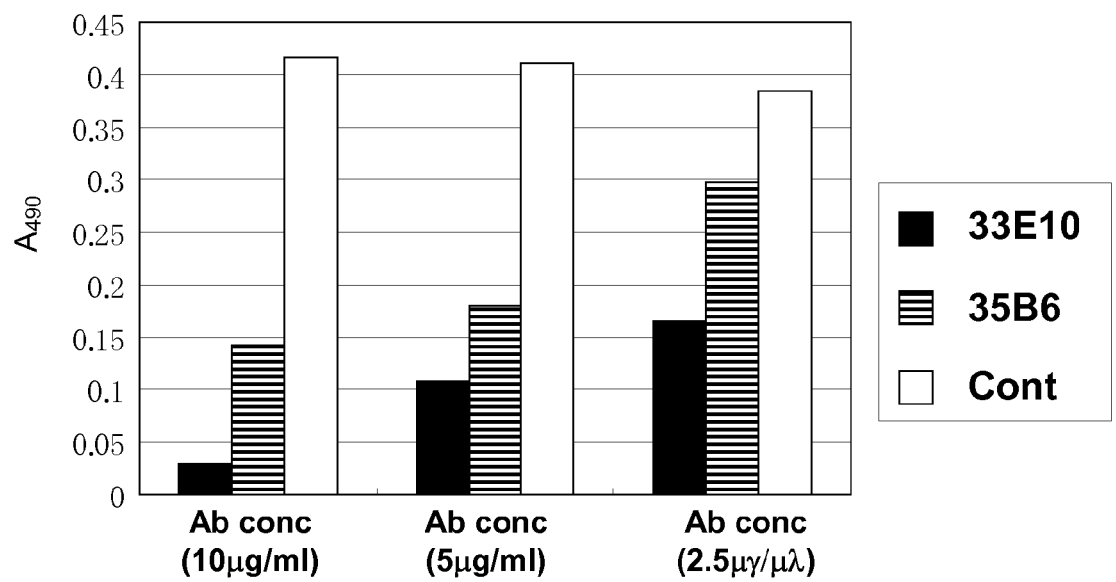
FIG. 9 shows the result of inhibition of binding of mOPN N-half to cancerous cells (NIH3T3 cells) by anti RGD antibodies.
Figures 10A, 10B, 10C:
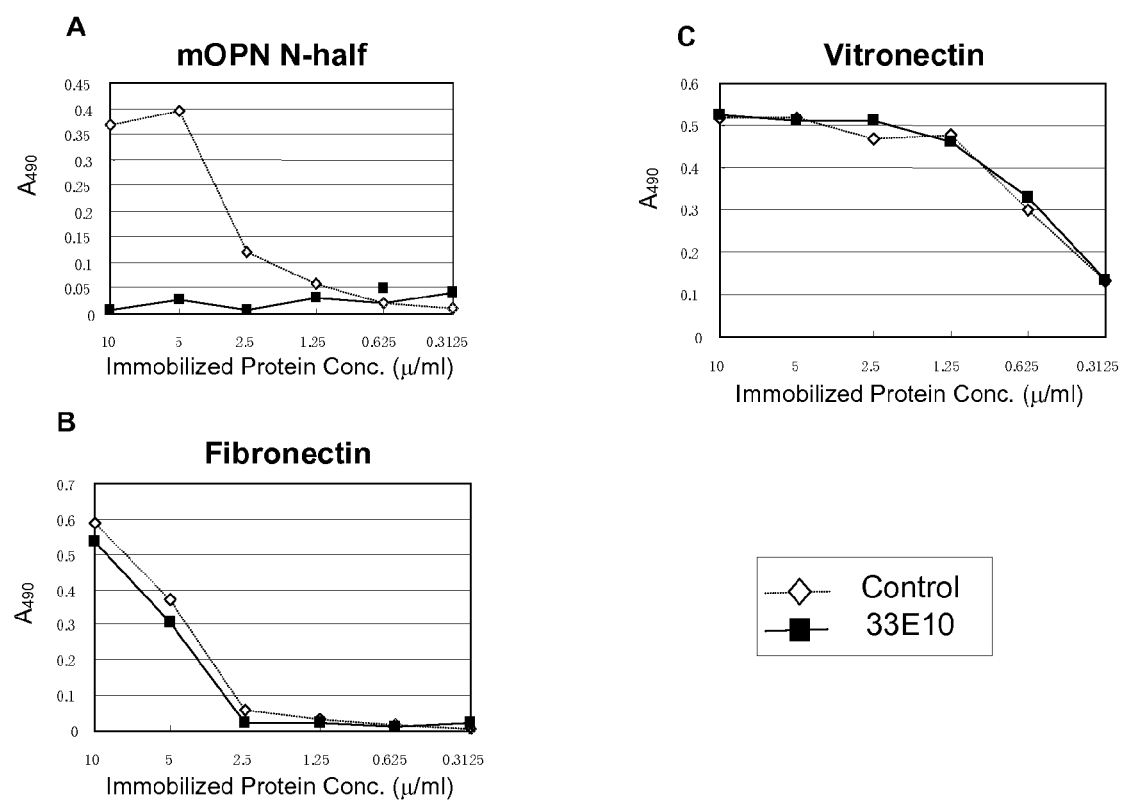
FIG. 10A-10C shows the result of inhibition of binding of various ECM proteins to cancerous cells (NIH3T3 cells) by anti RGD antibodies.

The result was shown in FIG. 8. Monoclonal antibody 33E10 was cross-reactive with all tested ECM proteins, but showed low reactivity with laminin. Monoclonal antibody 35B6 was reactive with hOPN and mOPN, but not with laminin.

6.5. Cell Adhesion Inhibitory Activity

Since it is known that cell adhesion involves the binding of the RGD peptide to its ligands, i.e., integrins and the like, the isolated anti-RGD antibodies were examined for their cell adhesion inhibitory activity. Each of a human OPN (hOPN) or a murine OPN (mOPN) was purified from culture supernatant of CHO-K1 cells introduced hOPN gene or mOPN gene respectively by using anti-OPN antibody column. N-half of mOPN was purified as a Glutathione S-transferase (GST) fusion protein with N-terminal portion of thrombin cleaved mOPN by isolating from *Escherichia coli*. A human FN and a human VN were obtained from Sigma Corporation.

50 μl of the proteins was added to each well of 96-well plate, incubated at 37° C. for 1 hour and immobilized onto the plate. After blocking the plate with a blocking solution (0.5% BSA/PBS) and washing with PBS once, the NIH3T3 cells suspended in 0.25% BSA-Minimum Essential Media (MEM) and the isolated monoclonal antibodies were mixed at final concentration of $1.0 \times 10^5$ cells/ml, and added to the plate at 200 μl/well and incubated at 37° C. for 1 hour under 5% $CO_2$. Non-adherent cells were rinsed off with PBS and adherent cells were fixed and stained with 0.5% Crystal Violet (by WAKO, Osaka, Japan)/20% methanol. The stained cells were allowed to stand at room temperature for 30 minutes. The plate was washed with distilled water and 20% acetic acid solution was added thereto to effect dissolution. The adhesion activity was quantified by measuring OD at 590 nm.

A mixture of NIH3T3 cells and monoclonal antibody 33E10 or 35B6 was added to 96-well plates immobilized mOPN N-half and examined the effect of antibody on binding of NIH3T3 cells to mOPN N-half. A mixture of NIH3T3 cells and monoclonal antibody 33E10 was added to 96-well plates each immobilized mOPN N-half, FN or VN, and examined the effect of antibody on binding of NIH3T3 cells to each protein.

As shown FIG. 9 and FIG. 10A-10C, NIH3T3 cells adhered to mOPN N-half and the adhesion was inhibited by anti-RGD antibodies. Monoclonal antibody 33E10 showed strong inhibitory activity as compared to monoclonal antibody 35B6. NIH3T3 cells adhered to all examined ECM proteins. Monoclonal antibody 33E10 inhibited cell adhesion with mOPN N-half, but did not inhibit cell adhesion with FN or VN. Thus, it is shown that the monoclonal antibody 33E10 specifically inhibits the adhesion between OPN and cells.

6.6. Therapeutic Effects of Anti-RGD Antibody

Therapeutic effects of anti-RGD antibodies were examined in a mouse system. The anti-RGD monoclonal antibodies (4P11, 11M6, 29R5, 30C7, 38I8, 33E10 and 35B6) were prepared substantially in the same manner as described for anti-RGD antibodies (see Section 6.1, supra).

6.6.1. Therapeutic Effect on Hepatitis

WO 02/081522 discloses that hepatitis can be treated by inhibiting the OPN functions. Accordingly, therapeutic effects of anti-RGD antibodies were studied in a mouse hepatitis model using mouse anti-RGD antibodies (4P11, 11M6, 29R5, 30C7, 38I8, 33E10 and 35B6). The blood AST and ALT levels in the mice (5 mice per group) were measured using GPT/ALT-PIII and GOT/AST-PIII (Fuji Film) 12 hours after an intravenous injection of 200 μg of concanavalin A (ConA) (Vector). Three hours before the ConA injection, 200 μg of the antibody were administered. A murine IgG was used as a control antibody.

Figure 11:
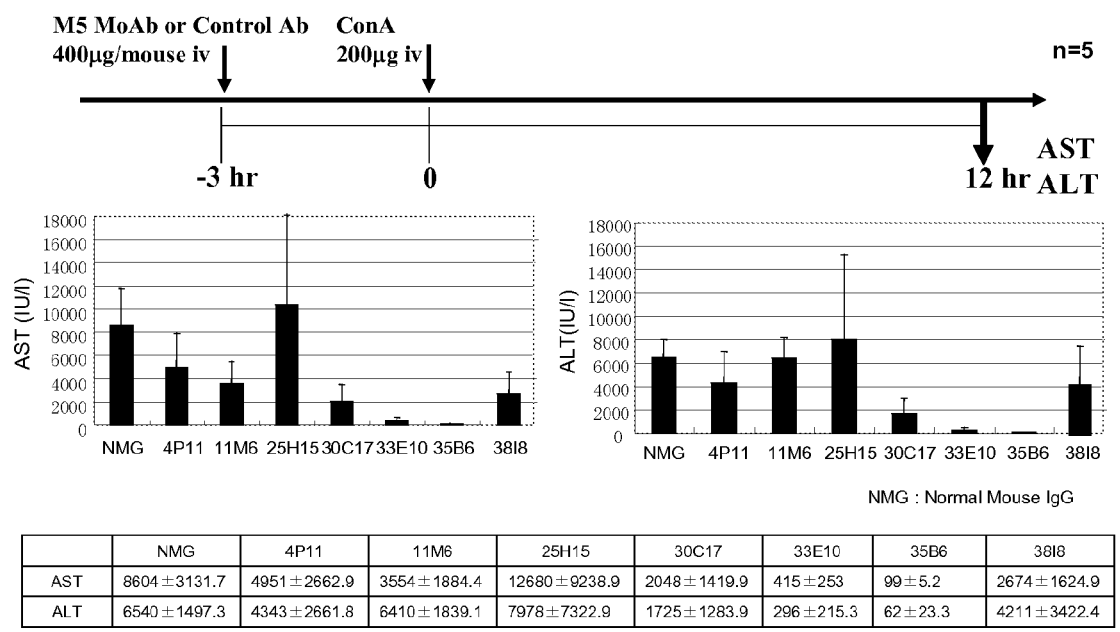
FIG. 11 shows the result of hepatitis inhibitory effect of anti RGD antibodies.

As shown in FIG. 11, monoclonal antibody 25H15 did not show any therapeutic effect, but monoclonal antibodies 4P11, 11M6, 29R5, 30C17 and 38I8 showed therapeutic effect. Mice administered with monoclonal antibody 33E10 or 35B6 showed no increase of AST and ALT levels. Hence, the results revealed that hepatitis may be treated by monoclonal antibody 33E10 or 35B6.

6.6.2. Effect of Anti-RGD Antibodies on Metastasis of Mouse Cancer Cell Line Effect of anti-RGD antibodies on metastasis was studied in mouse experimental model and spontaneous model of pulmonary metastasis.

In the experimental model, murine melanoma cell line B16-Luc cells ($1 \times 10^5$ cells/mouse) mixed with 400 μg/mouse of monoclonal antibodies were injected in tail vein of C57BL/6 mice, and 14 days after injection, number of pulmonary metastasis was counted. Antibodies of the same class (mIgG1) were used as controls.

In the spontaneous model, murine melanoma cell line B16-BL6 cells ($4\times10^5$ cells/mouse) were subcutaneously injected into the left footpad of C57BL/6 mice. 19 days after injection, original tumor was surgically resected, and 14 days after resection (33 days after injection of B16-BL6 cells), number of tumor colonies in lung from sacrificed mice were counted. 200 µg/mouse of monoclonal antibodies were intraperitoneally administered 8 times at 3, 5, 7, 9, 11, 13, 15 and 17 days after injection of tumor cells. Size of original tumor was measured until surgical resection. 14 days after the surgical resection, number of tumor colonies in lung was counted. Antibodies of the same class (mIgG1) were used as controls.

Figures 12A, 12B:
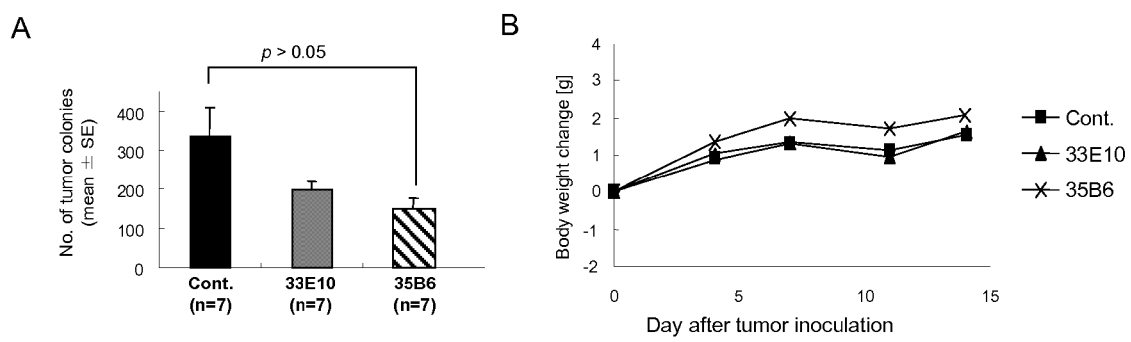
FIG. 12A-12B shows the result of pulmonary metastasis inhibitory effect of anti RGD antibodies in experimental metastasis model.

The result of the mouse experimental model is shown in FIG. 12A-12B. Compared to the control, the average number of pulmonary metastasis was low in the mice administered with monoclonal antibody 33E10 or 35B6. Monoclonal antibody 35B6 significantly inhibited pulmonary metastasis.

Figures 13A, 13B, 13C:
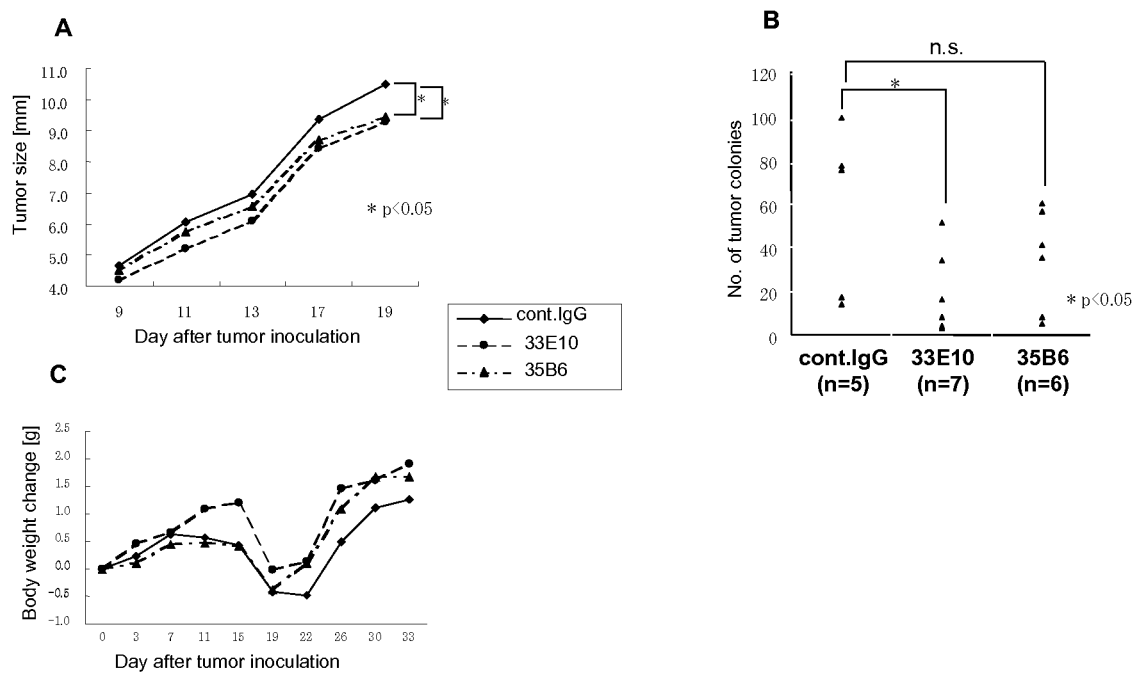
FIG. 13A-13C shows the result of pulmonary metastasis inhibitory effects of anti RGD antibodies in spontaneous metastasis model.

FIG. 13A-13C show the results of the mouse spontaneous model in the following format: original tumor size variation per day, the number of pulmonary metastasis colonies, and body weight change. Compared to the control mice, the size of original tumor was smaller in mice administered with either monoclonal antibody 33E10 or 35B6. Hence, the results show that tumor growth may be inhibited by monoclonal antibody 33E10 or 35B6. Since two of the five mice in control group showed too many pulmonary metastasis colonies, the statistically significant difference for 35B6 was not shown. However, the average number of pulmonary metastasis was low in the mice administered with monoclonal antibody 33E10 or 35B6 as compared to the control antibody; thus, showing that monoclonal antibody 33E10 or 35B6 inhibits tumor metastasis.

6.6.3. Therapeutic Effect of Anti-RGD Antibody in Mouse Rheumatoid Arthritis Model Rheumatoid arthritis was induced to mice using cocktail of type II collagen-specific monoclonal antibody (IBL, Japan) according to the supplier's protocol. Namely, mice (Balb/c) were injected cocktail of type II collagen-specific monoclonal antibody, after 3 days of injection LPS was injected to develop rheumatoid arthritis. Anti-RGD monoclonal antibodies or normal hamster IgG (NHG) were administered intraperitoneally total of 8 times at 200 µg/mouse/day from one day before the collagen antibody injection until 6 days after the of the collagen antibody injection. The mice were observed everyday from the day of the collagen antibody injection and the levels of arthritis were scored by grading each paw from 0-4 based on erythema and swelling of the joint (0=no erythema or swelling; 1=erythema or swelling of one small joint such as toe; 2=erythema or swelling of two or more of small joint or erythema or swelling of larger joint such as wrist or ankle; 3=erythma or swelling of the entire paw; 4=complete erythma or swelling of the entire paw; maximum score of one mouse (4 paws) is 16).

Figure 14:
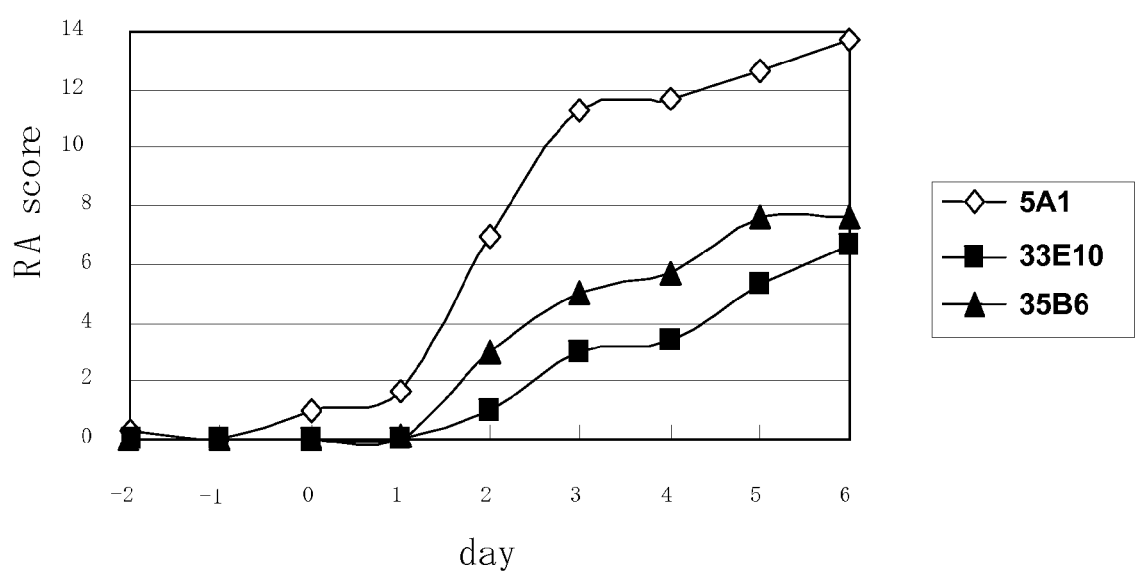
FIG. 14 shows the result of studies of therapeutic effects of anti RGD antibodies in rheumatoid arthritis model.

The result is shown in FIG. 14. Mice injected with control NHG had a high score and developed rheumatoid arthritis, whereas those injected with each of anti-RGD antibody 33E10 or 35B6 had a small score and the development of rheumatoid arthritis was completely blocked. Thus, in light of the results, anti-RGD antibodies showed to have prophylactic and therapeutic effects on rheumatoid arthritis.

6.6.4. Therapeutic Effect of Anti-RGD Antibody in Mouse Endometriosis Model

The symptom of endometriosis indicates the cyst formation, an inflammation in the surrounded stroma, smooth muscle metaplasia, neuropoiesis and angiogenesis by heterotopic growth of the endometrial epithelium. It was reported that osteopontin (OPN) is highly expressed in human endometriosis and rat endometriosis model, by the immuno-histochemical method. Therefore, the therapeutic effect on the animal model by anti-RGD antibody (33E10) was investigated as a new therapy to endometriosis.

C57BL/6J female mice (9 weeks) were used. Eighteen mice ware prepared the endometriosis model. The right uterus was removed, and auto-transplanted 2 pieces of 2 mm×2 mm square of the uterus to abdomen. The left uterus was not treated for reference. Mouse anti-RGD antibody (500 µg/head, ip) was given to 9 mice (Treated group), twice a week for 4 weeks (8 times administration, total administration amount: 4000 µg/head). Control group (9 mice) was not administrated with antibody. After administration, the number of the formed cyst was checked, and the pathological change was observed by histology.

The results were shown in TABLE 1. There were no differences in the weight in the two groups. The number of appeared endometriosis of the treated group was markedly reduced than of the control group. The weight of the formed cyst decreased clearly with about ⅓ by an average by treated group more than control group. It could be confirmed that the OPN expression in the endometrial epithelium was suppressed by antibody treatment by immuno-histochemical study. The thickness of the smooth muscle in the stroma of treated group decreased in ½ more than control group.

The therapeutic effect of the mice endometriosis model was indicated by the anti-RGD antibody administration.

TABLE 1

|  | Control group | Treated group |
|---|---|---|
| Total number of transplantation | 18 | 18 |
| Number of appeared endometriosis | 13 | 6 |
| Weight of cyst (mg)[1] | 21.00 ± 4.04 | 7.06 ± 2.55 |
| Size of cyst (mm²)[2] | 4.17 ± 0.92 | 1.22 ± 0.51 |
| Thickness of smooth muscle (µm)[3] | 10.00 ± 1.95 | 5.00 ± 1.78 |

[1] $p = 0.0437$
[2] $p = 0.0144$
[3] $p = 0.0787$ 6.7. Humanization of Non-Human Antibodies 6.7.1. Cloning and Sequencing of Mouse 33E10 Variable Region Genes Mouse 33E10 hybridoma cells were grown in TIL Media I (Immuno-Biological Laboratories, Gunma, Japan) containing 10% fetal bovine serum (FBS; HyClone, Logan, Utah) at 37° C. in a 7.5% $CO_2$ incubator. Total RNA was extracted from approximately $3\times10^6$ hybridoma cells using TRIzol reagent (Invitrogen, Carlsbad, Calif.) according to the supplier's protocol. Oligo dT-primed cDNA was synthesized using the GeneRacer Kit (Invitrogen) following the supplier's protocol. The variable region cDNAs for 35B6 heavy and light chains were amplified by polymerase chain reaction (PCR) with Phusion DNA polymerase (New England Biolabs, Beverly, Mass.) using 3' primers that anneal respectively to the mouse gamma-1 and kappa chain constant regions, and a GeneRacer 5' primer (5'-CGACTGGAGCACGAGGA-CACTGA-3') (SEQ ID NO:84) provided in the GeneRacer Kit. For PCR amplification of VH, the 3' primer has the sequence 5'-GCCAGTGGATAGACAGATGG-3' (SEQ ID NO:85). For PCR amplification of VL, the 3' primer has the sequence 5'-GATGGATACAGTTGGTGCAGC-3' (SEQ ID NO:86). The amplified VH and VL cDNAs were cloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of 33E10 VH and VL are shown in FIGS. 15 and 16, respectively.

6.7.2. Construction of Chimeric 33E10 IgG1/κ Antibody

A gene encoding 33E10 VH was generated as an exon including a splice donor signal and appropriate flanking restriction enzyme sites by PCR using 33E10 VH cDNA as a template, 5'-GGGACTAGTACCACCATGAAGTTGTGG-CTGAACTGGATT-3' (SpeI site is underlined) (SEQ ID NO:87) as a 5' primer, and 5'-GGGAAGCTTGAAGTT-AGGACTCACCTGCAGAGACAGTGACCAGAGTCCC-3' (HindIII site is underlined) (SEQ ID NO:88) as a 3' primer (FIG. 17). Likewise, a gene encoding 33E10 VL was generated as an exon including a splice donor signal and appropriate flanking restriction enzyme sites by PCR using 33E10 VL cDNA as a template, 5'-GGGGCTAGCACCACCAT-GAAGTTGCCTGTTAGGCTGTTG-3' (NheI site is underlined) (SEQ ID NO:89) as a 5' primer, and 5'-GGG-GAATTCTTTGGATTCTACTTACGTTTGATTTCCAGC-TTGGTGCCTCC-3' (EcoRI site is underlined) (SEQ ID NO:90) as a 3' primer (FIG. 18). The splice donor signals of the 33E10 VH and VL exons were derived from the mouse germline JH3 and Jκ1 sequences, respectively. PCR-amplified fragments were gel-purified using QIAquick Gel Extraction Kit (Qiagen, Valencia, Calif.), digested with SpeI and HindIII (for VH) or NheI and EcoRI (for VL), and cloned into a mammalian expression vector carrying human gamma-1 and kappa constant regions for production of chimeric 33E10 IgG1/κ antibody. The schematic structure of the resulting expression vector, pCh33E10, is shown in FIG. 19.

6.7.3. Generation of Humanized 33E10 VH and VL Genes

Humanization of the 33E10 variable regions was carried out as outlined by Queen et al. (Proc. Natl. Acad. Sci. USA 86: 10029-10033, 1989). First, a molecular model of the 33E10 variable regions was constructed with the aid of computer programs. Next, based on a homology search against human variable region sequences, the human amino acid sequence of U03400 (GenBank accession number), which has a high homology to 33E10 VH, was chosen as an acceptor to provide the frameworks for humanized 33E10 VH. Likewise, the human amino acid sequence of X72452 (GenBank accession number) was chosen as an acceptor for humanization of 33E10 VL.

At framework positions where the computer model suggested significant contact with the CDRs, the amino acids from the mouse 33E10 variable regions were substituted for the human framework amino acids. This was done at positions 30 and 48 to generate humanized 33E10 (Hu33E10) VH (FIG. 20). For the light chain, no replacements were needed to generate humanized 33E10 (Hu33E10) VL (FIG. 21). The alignments of 33E10, designed Hu33E10 and the human acceptor amino acid sequence are shown for VH in FIG. 20 and for VL in FIG. 21.

A gene encoding each of Hu33E10 VH and VL was designed as an exon including a signal peptide, a splice donor signal, and appropriate restriction enzyme sites for subsequent cloning into a mammalian expression vector. The splice donor signals of the Hu33E10 VH and VL exons were derived from the human germline JH4 and Jκ1 sequences, respectively. The signal peptide sequence of the mouse 33E10 VL gene was indicated to be suboptimal for precise cleavage by the SIG-Pred signal peptide prediction software (http://bmbpcu36.leeds.ac.uk/prot_analysis/Signal.html). Therefore, the signal peptide of the VL gene of the mouse monoclonal antibody 35B6 (Gene Techno Science), which was predicted to be cleaved efficiently and precisely by the SIG-Pred software, was used in the Hu33E10 VL exon. The signal peptide sequence in the Hu33E10 VH exon was derived from the corresponding mouse 33E10 VH sequence. The SIG-Pred software indicated that the signal peptide of the Hu33E10 VH gene is cleaved efficiently and precisely.

The Hu33E10 VH and VL genes were constructed by extension and PCR amplification of several overlapping synthetic oligonucleotide primers (SEQ ID NOS:91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122 and 123) using Phusion DNA polymerase as outlined by He et al. (J. Immunol. 160: 1029-1035, 1998). The oligonucleotides used for construction of Hu33E10 VH and VL genes are listed in FIG. 22 and FIG. 23, respectively. The location of the oligonucleotides in the Hu33E10 VH and VL genes is shown in FIGS. 24 and 25, respectively. PCR-amplified fragments were gel-purified using QIAquick Gel Extraction Kit (Qiagen) and cloned into pCR4Blunt-TOPO vector for sequence determination. After digestion with SpeI and HindIII (for VH) or NheI and EcoRI (for VL), Hu33E10 VH and VL genes were subcloned into corresponding sites in a mammalian expression vector for production in the human IgG1/κ form. The schematic structure of the resulting expression vector, pHu33E10, is shown in FIG. 19. The nucleotide sequences of the obtained Hu33E10 VH and VL genes along with deduced amino acid sequences are shown in FIG. 26 (SEQ ID NO:52) and FIG. 27 (SEQ ID NO:54), respectively.

6.7.4. Transient Expression of Chimeric and Humanized 33E10 IgG1/κ

Chimeric and humanized 33E10 IgG1/κ antibodies are transiently expressed by transfecting pCh35B6 and pHu35B6 plasmid DNA, respectively, to HEK293 cells using polyethylenimine according to Durocher et al. (Nucl. Acids Res. 30: e9, 2002). Transiently transfected HEK293 cells are maintained for two days in DMEM containing 10% FBS at 37° C. in a 7.5% $CO_2$ incubator. The expression level of each of Ch33E10 and Hu33E10 IgG1/κ antibodies in culture supernatant is measured by sandwich ELISA. An ELISA plate is coated overnight at 4° C. with 100 μl/well of 1/2,000-diluted goat anti-human IgG Fcγ-chain-specific polyclonal antibody (SouthernBiotech, Birmingham, Ala.) in PBS, washed with Wash Buffer (PBS containing 0.05% Tween 20), and blocked for 1 hr at room temperature with 300 μl/well of Blocking Buffer (PBS containing 2% Skim Milk and 0.05% Tween 20). After washing with Wash Buffer, 100 μl/well of samples appropriately diluted in ELISA Buffer (PBS containing 1% Skim Milk and 0.025% Tween 20) are applied to the ELISA plate. Human IgG1/κ antibody purified from human myeloma serum (SouthernBiotech) is used as a standard. After incubating the ELISA plate for 2 hr at room temperature and washing with Wash Buffer, bound antibodies are detected using 100 μl/well of 1/2,000-diluted HRP-conjugated goat anti-human kappa chain polyclonal antibody (SouthernBiotech). After incubating for 1 hr at room temperature and washing with Wash Buffer, color development is performed by adding 100 μl/well of ABTS substrate (bioWORLD, Dublin, Ohio). Color development is stopped by adding 100 μl/well of 2% oxalic acid. Absorbance is read at 405 nm.

6.7.5. Characterization of Humanized 35B6

The affinity of humanized 35B6 IgG1/κ is compared to that of chimeric 33E10 IgG1/κ by ELISA. As an antigen, synthetic oligopeptide (Cys-Val-Asp-Thr-Tyr-Asp-Gly-Arg-Gly-Asp-Ser-Val-Val-Tyr-Gly-Leu-Arg-Ser) (SEQ ID NO:

166) conjugated to bovine serum albumin (hOPN5-BSA) is used. In a typical experiment, an ELISA plate is coated with 100 µl/well of 1 µg/ml hOPN-BSA in PBS overnight at 4° C., washed with Wash Buffer, and blocked with 300 µl/well of Blocking Buffer for 1 hr at room temperature. After washing with Wash Buffer, 100 µl/well of samples appropriately diluted in ELISA Buffer are applied to the ELISA plate. After incubating the ELISA plate overnight at 4° C. and washing with Wash Buffer, bound antibodies are detected using 100 µl/well of 1/2,000-diluted HRP-conjugated goat anti-human γ chain polyclonal antibody (SouthernBiotech). After incubating for 1 hr at room temperature and washing with Wash Buffer, color development is performed by adding 100 µl/well of ABTS substrate and stopped with 100 µl/well of 2% oxalic acid. Absorbance is read at 405 nm.

6.7.6. Cloning and Sequencing of Mouse 35B6 Variable Region Genes

Mouse 35B6 hybridoma cells were grown in TIL Media I (Immuno-Biological Laboratories, Gunma, Japan) containing 10% fetal bovine serum (FBS; HyClone, Logan, Utah) at 37° C. in a 7.5% $CO_2$ incubator. Total RNA was extracted from approximately $3\times10^6$ hybridoma cells using TRIzol reagent (Invitrogen, Carlsbad, Calif.) according to the supplier's protocol. Oligo dT-primed cDNA was synthesized using the GeneRacer Kit (Invitrogen) following the supplier's protocol. The variable region cDNAs for 35B6 heavy and light chains were amplified by polymerase chain reaction (PCR) with Phusion DNA polymerase (New England Biolabs, Beverly, Mass.) using 3' primers that anneal respectively to the mouse gamma-1 and kappa chain constant regions, and a GeneRacer 5' primer (5'-CGACTGGAGCACGAGGA-CACTGA-3') (SEQ ID NO:84) provided in the GeneRacer Kit. For PCR amplification of VH, the 3' primer has the sequence 5'-GCCAGTGGATAGACAGATGG-3' (SEQ ID NO:124). For PCR amplification of VL, the 3' primer has the sequence 5'-GATGGATACAGTTGGTGCAGC-3' (SEQ ID NO:125). The amplified VH and VL cDNAs were cloned into the pCR4Blunt-TOPO vector (Invitrogen) for sequence determination. DNA sequencing of the variable regions was carried out at Tocore (Menlo Park, Calif.). Several heavy and light chain clones were sequenced and unique sequences homologous to typical mouse heavy and light chain variable regions were identified. The consensus cDNA sequences along with deduced amino acid sequences of 35B6 VH and VL are shown in FIGS. 28 and 29, respectively.

6.7.7. Construction of Chimeric 35B6 IgG1/κ Antibody

A gene encoding 35B6 VH was generated as an exon including a splice donor signal and appropriate flanking restriction enzyme sites by PCR using 35B6 VH cDNA as a template, 5'-GGGACTAGTACCACCATGGGATGGAGC-TGTATCCTC-3' (SpeI site is underlined) (SEQ ID NO:126) as a 5' primer, and 5'-GGGAAGCTTAAAAAAAGCC-AGCTTACCTGAGGAGACGGTGACCGTGGTCCC-3' (HindIII site is underlined) (SEQ ID NO:127) as a 3' primer (FIG. 30). Likewise, a gene encoding 35B6 VL was generated as an exon including a splice donor signal and appropriate flanking restriction enzyme sites by PCR using 35B6 VL cDNA as a template, 5'-GGGGCTAGCACCACCATGAG-GACCCCTGCTCAGTTTCTT-3' (NheI site is underlined) (SEQ ID NO:128) as a 5' primer, and 5'-GGG-GAATTCGCAAAAGTCTACTTACGTTTTATTTCCAAC-TTTGTCCCCGA-3' (EcoRI site is underlined) (SEQ ID NO:129) as a 3' primer (FIG. 31). The splice donor signals of the 35B6 VH and VL exons were derived from the mouse germline JH1 and Jκ4 sequences, respectively. PCR-amplified fragments were gel-purified using QIAquick Gel Extraction Kit (Qiagen, Valencia, Calif.), digested with SpeI and HindIII (for VH) or NheI and EcoRI (for VL), and cloned into a mammalian expression vector carrying human gamma-1 and kappa constant regions for production of chimeric 35B6 IgG1/κ antibody. The schematic structure of the resulting expression vector, pCh35B6, is shown in FIG. 32.

6.7.8. Generation of Humanized 35B6 VH and VL Genes

Humanization of the 35B6 variable regions was carried out as outlined by Queen et al. (Proc. Natl. Acad. Sci. USA 86: 10029-10033, 1989). First, a molecular model of the 35B6 variable regions was constructed with the aid of computer programs. Next, based on a homology search against human variable region sequences, the human amino acid sequence of Z47230 (GenBank accession number), which has a high homology to 35B6 VH, was chosen as an acceptor to provide the frameworks for humanized 35B6 VH. Likewise, the human amino acid sequence of X72479 (GenBank accession number) was chosen as an acceptor for humanization of 35B6 VL.

At framework positions where the computer model suggested significant contact with the CDRs, the amino acids from the mouse 35B6 variable regions were substituted for the human framework amino acids. This was done at positions 48, 66, 67, 68, 69 and 71 to generate humanized 35B6 (Hu35B6) VH (FIG. 33). For the light chain, replacements were made at positions 46 and 69 to generate humanized 35B6 (Hu35B6) VL (FIG. 34). The alignments of 35B6, designed Hu35B6, and the human acceptor amino acid sequence are shown for VH in FIG. 33 and for VL in FIG. 34.

A gene encoding each of Hu35B6 VH and VL was designed as an exon including a signal peptide, a splice donor signal, and appropriate restriction enzyme sites for subsequent cloning into a mammalian expression vector. The splice donor signals of the Hu35B6 VH and VL exons were derived from the human germline JH6 and Jκ1 sequences, respectively. The signal peptide sequence of the mouse 35B6 VH gene was indicated to be suboptimal for precise cleavage by the SIG-Pred signal peptide prediction software (http://bmbpcu36.leeds.ac.uk/prot_analysis/Signal.html). Therefore, the signal peptide of the VH gene of the mouse monoclonal antibody 33E10 (Gene Techno Science), which was predicted to be cleaved efficiently and precisely by the SIG-Pred software, was used in the Hu35B6 VH exon. The signal peptide sequence in the humanized Hu35B6 VL exon was derived from the corresponding mouse 35B6 VL sequence. The SIG-Pred software indicated that the signal peptide of the Hu35B6 VL gene is cleaved efficiently and precisely.

The Hu35B6 VH and VL genes were constructed by extension and PCR amplification of several overlapping synthetic oligonucleotide primers (SEQ ID NOS:91, 92, 130, 131, 132, 133, 134, 135, 136, 137, 138, 139, 140, 141, 142, 143, 107, 108, 144, 145, 146, 147, 148, 149, 150, 151, 152, 153, 154 and 155) using Phusion DNA polymerase as outlined by He et al. (J. Immunol. 160: 1029-1035, 1998). The oligonucleotides used for construction of Hu35B6 VH and VL genes are listed in FIG. 35 and FIG. 36, respectively. The location of the oligonucleotides in the Hu35B6 VH and VL genes is shown in FIGS. 37 and 38, respectively. PCR-amplified fragments were gel-purified using QIAquick Gel Extraction Kit (Qiagen) and cloned into pCR4Blunt-TOPO vector for sequence determination. After digestion with SpeI and HindIII (for VH) or NheI and EcoRI (for VL), Hu35B6 VH and VL genes were subcloned into corresponding sites in a mammalian expression vector for production in the human IgG1/κ form. The schematic structure of the resulting expression vector, pHu35B6, is shown in FIG. 32. The nucleotide sequences of the obtained Hu35B6 VH and VL genes along with deduced amino acid sequences are shown in FIG. 39 (SEQ ID NO:68) and FIG. 40 (SEQ ID NO:70), respectively.

6.7.9. Transient Expression of Chimeric and Humanized 35B6 IgG1/κ

Chimeric and humanized 35B6 IgG1/κ antibodies were transiently expressed by transfecting pCh35B6 and pHu35B6 plasmid DNA, respectively, to HEK293 cells using polyethylenimine according to Durocher et al. (Nucl. Acids Res. 30: e9, 2002). Transiently transfected HEK293 cells were maintained for two days in DMEM containing 10% FBS at 37° C. in a 7.5% $CO_2$ incubator. The expression level of each of Ch35B6 and Hu35B6 IgG1/κ antibodies in culture supernatant was measured by sandwich ELISA. An ELISA plate was coated overnight at 4° C. with 100 µl/well of 1/2,000-diluted goat anti-human IgG Fcγ-chain-specific polyclonal antibody (SouthernBiotech, Birmingham, Ala.) in PBS, washed with Wash Buffer (PBS containing 0.05% Tween 20), and blocked for 1 hr at room temperature with 300 µl/well of Blocking Buffer (PBS containing 2% Skim Milk and 0.05% Tween 20). After washing with Wash Buffer, 100 µl/well of samples appropriately diluted in ELISA Buffer (PBS containing 1% Skim Milk and 0.025% Tween 20) were applied to the ELISA plate. Human IgG1/κ antibody purified from human myeloma serum (SouthernBiotech) was used as a standard. After incubating the ELISA plate for 2 hr at room temperature and washing with Wash Buffer, bound antibodies were detected using 100 µl/well of 1/2,000-diluted HRP-conjugated goat anti-human kappa chain polyclonal antibody (SouthernBiotech). After incubating for 1 hr at room temperature and washing with Wash Buffer, color development was performed by adding 100 µl/well of ABTS substrate (bio-WORLD, Dublin, Ohio). Color development was stopped by adding 100 µl/well of 2% oxalic acid. Absorbance was read at 405 nm.

6.7.10. Characterization of Humanized 35B6

The affinity of humanized 35B6 IgG1/κ was compared to that of chimeric 35B6 IgG1/κ by ELISA. As an antigen, synthetic oligopeptide (Cys-Val-Asp-Thr-Tyr-Asp-Gly-Arg-Gly-Asp-Ser-Val-Val-Tyr-Gly-Leu-Arg-Ser) (SEQ ID NO: 166) conjugated to bovine serum albumin (hOPN5-BSA) was used. In a typical experiment, an ELISA plate was coated with 100 µl/well of 1 µg/ml hOPN-BSA in PBS overnight at 4° C., washed with Wash Buffer, and blocked with 300 µl/well of Blocking Buffer for 1 hr at room temperature. After washing with Wash Buffer, 100 µl/well of samples appropriately diluted in ELISA Buffer were applied to the ELISA plate. After incubating the ELISA plate overnight at 4° C. and washing with Wash Buffer, bound antibodies were detected using 100 µl/well of 1/2,000-diluted HRP-conjugated goat anti-human γ chain polyclonal antibody (SouthernBiotech). After incubating for 1 hr at room temperature and washing with Wash Buffer, color development was performed by adding 100 µl/well of ABTS substrate and stopped with 100 µl/well of 2% oxalic acid. Absorbance was read at 405 nm. As shown in FIG. 41A-41B, the binding of humanized 35B6 IgG1/κ to hOPN5-BSA was similar to (FIG. 41A) or indistinguishable from (FIG. 41B) that of chimeric 35B6 IgG1/κ. This results indicates that humanization of mouse 35B6 antibody is successful.

7. DEPOSITION

The hybridomas designated herein as 33E10 and 35B6 producing mouse anti-RGD monoclonal antibodies were deposited on Oct. 27, 2005 with International Patent Organisms Depository, National Institute of Advanced Industrial Science and Technology, located at Central 6, 1-1-1 Higashi, Tsukuba, Ibaraki (postal code: 305-8566) in accordance with the Budapest Treaty on the Deposit of Microorganisms, and accorded Accession Nos. FERM BP-10440 and FERM BP-10441, respectively, all of which are incorporated herein by reference in their entirety.

8. INDUSTRIAL APPLICABILITY

The humanized monoclonal antibodies of the present invention inhibit the function of RGD proteins to exhibit therapeutic effects on cancer, e.g., the growth or metastasis of cancer cells, and an inflammatory disease, e.g., rheumatoid arthritis, osteoarthritis, hepatitis, bronchial asthma, fibrosis, diabetes mellitus, arteriosclerosis, multiple sclerosis, granuloma, an inflammatory bowel disease (ulcerative colitis and Crohn's disease), an autoimmune disease, and the like. The pharmaceutical composition comprising both the anti-RGD antibody and anti-integrin antibody of the present invention exerts more improved therapeutic effects on cancer and an inflammatory disease.

9. LIST OF SEQUENCES

The sequences referenced throughout the specification are summarized below.

| SEQ ID NO. | TYPE | DESCRIPTION | SEQUENCE |
|---|---|---|---|
| 1 | AA | CDRH1 of 33E10 (FERM BP-10440) | GFTFTDYYMI |
| 2 | AA | CDRH2 of 33E10 (FERM BP-10440) | WLGFIRNKANGYTTEYSASVKG |
| 3 | AA | CDRH3 of 33E10 (FERM BP-10440) | GAY |
| 4 | AA | CDRL1 of 33E10 (FERM BP-10440) | RSSQSIVHSNGNTYLE |
| 5 | AA | CDRL2 of 33E10 (FERM BP-10440) | RVSNRFS |

| SEQ ID NO. | TYPE | DESCRIPTION | SEQUENCE |
|---|---|---|---|
| 6 | AA | CDRL3 of 33E10 (FERM BP-10440) | GSFVPW |
| 7 | AA | CDRH1 of 35B6 (FERM BP-10441) | GYTFTNYWMH |
| 8 | AA | CDRH2 of 35B6 (FERM BP-10441) | WIGNINPRNGDSNYNEKFRS |
| 9 | AA | CDRH3 of 35B6 (FERM BP-10441) | GYFDV |
| 10 | AA | CDRL1 of 35B6 (FERM BP-10441) | KASQDINSYLS |
| 11 | AA | CDRL2 of 35B6 (FERM BP-10441) | RANRLVD |
| 12 | AA | CDRL3 of 35B6 (FERM BP-10441) | YDEFPF |
| 13 | DNA | X65891 | ATGGACTGGACCTGGAGGGTCCTCTTTTTGGTGGC AGCAGCCACAGGTGCCCACTCCCAGGTCCAGCTTG TGCAGTCTGGGGCTGAGGTGAAGAAGCCTGGGGCC TCAGTGAAGGTTTCCTGCAAGGCTTCTGGATACAC CTTCACTAGCTATGCTATGCATTGGGTGCGCCAGG CCCCCGGACAAAGGCTTGAGTGGATGGGATGGATC AACGCTGGCAATGGTAACACAAAATATTCACAGAA GTTCCAGGGCAGAGTCACCATTACCAGGGACACAT CCGCGAGCACAGCCTACATGGAGCTGAGCAGCCTG AGATCTGAAGACACGGCTGTGTATTACTGTGCGAG AATACCCCGTATTAGCAGTGGCTGGTTGGGGGACT ACTTTGACTACTGGGGCCAGGGAACCCTGGTCACC GTCTCCTCA |
| 14 | AA | FRH1 of X65891 | QVQLVQSGAEVKKPGASVKVSCKASGYTFT |
| 15 | AA | FRH2 of X65891 | WVRQAPGQRLEWMG |
| 16 | AA | FRH3 of X65891 | RVTITRDTSASTAYMELSSLRSEDTAVYYCAR |
| 17 | AA | FRH4 of X65891 | WGQGTLVTVSS |
| 18 | DNA | X72441 | CGCTCAGCTCCTGGGGCTCCTGCTACTCTGGCTCC GAGGTGCCAGATGTGACATCCAGATGACCCAGTCT CCATCCTCCCTGTCTGCATCTGTAGGAGACAGAGT CACCATCACTTGCCGGGCAAGTCAGAGCATTAGCA GCTATTTAAATTGGTATCAGCAGAAACCAGGGAAA GCCCCTAAGCTCCTGATCTATGCTGCATCCAGTTT GCAAAGTGGGGTCCCATCAAGGTTCAGTGGCAGTG GATCTGGGACAGATTTCACTCTCACCATCAGCAGT CTGCAACCTGAAGATTTTGCAACTTACTACTGTCA ACAGAGTTACAGTACCCCTCGGACGTTCGGCCAAG GGACCAAGGTGGAAATCAAA |
| 19 | AA | FRL1 of X72441 | DIQMTQSPSSLSASVGDRVTITC |
| 20 | AA | FRL2 of X72441 | WYQQKPGKAPKLLIY |
| 21 | AA | FRL3 of X72441 | GVPSRFSGSGSGTDFTLTISSLQPEDFATYYC |
| 22 | AA | FRL4 of X72441 | FGQGTKVEIK |

-continued

| SEQ ID NO. | TYPE | DESCRIPTION | SEQUENCE |
|---|---|---|---|
| 23 | DNA | VH of Hu33E10 | GAAGTGCAGCTGGTGGAGTCTGGAGGAGGCTTGGT ACAGCCTGGGGGTTCTCTGAGACTCTCCTGTGCAG CTTCTGGATTCACCTTCACTGATTACTACATGATC TGGGTCCGCCAGGCTCCAGGGAAGGGACTTGAGTG GTTGGGTTTTATTAGAAACAAAGCTAATGGTTACA CAACAGAGTACAGTGCATCTGTGAAGGGTCGGTTC ACCATCTCCAGAGATAATGCCAAGAACTCACTCTA TCTTCAAATGAATTCCCTGAGAGCTGAGGACACGG CCGTGTATTACTGTGCAAGGGGCGCTTACTGGGGC CAAGGGACTATGGTCACTGTCTCTTCA |
| 24 | AA | VH of Hu33E10 | EVQLVESGGGLVQPGGSLRLSCAASGFTFTDYYMI WVRQAPGKGLEWLGRFTISRDNAKNSLYLQMNSLR AEDTAVYYCARGAYWGQGTMVTVSS |
| 25 | DNA | VL of Hu33E10 | GATATTGTGATGACCCAATCTCCACTCTCCCTGCC TGTCACTCCTGGAGAGCCAGCCTCCATCTCTTGCA GATCTAGTCAGAGCATTGTACATAGTAATGGAAAC ACCTATTTAGAATGGTACCTGCAGAAACCAGGCCA GTCTCCACAGCTCCTGATCTACAGAGTTTCCAACC GATTTTCTGGGGTCCCAGACAGGTTCAGTGGCAGT GGATCAGGGACAGATTTCACACTCAAGATCAGCAG GATGGAGGCTGAGGATGTCGGAGTTTATTACTGCT TTCAAGGTTCATTGTTCCGTGGACGTTCGGTCAA GGCACCAAAGTGGAAATCAAA |
| 26 | AA | VL of Hu33E10 | DIVMTQSPLSLPVTPGEPASISCRSSQSIVHSNGN TYLEWYLQKPGQSPQLLIYRVSNRFSGVPDRFSGS GSGTDFTLKISRVEAEDVGVYYCFQGSFVPWTFGQ GTKVEIK |
| 27 | DNA | VH of Hu35B6 | CAGGTCCAACTGGTGCAGTCTGGGGCTGAAGTGAA GAAGCCTGGGGCTTCAGTGAAGGTGTCCTGTAAGG CTTCTGGCTACACCTTCACCAACTACTGGATGCAC TGGGTGCGACAGGCCCCTGGACAAGGGCTTGAGTG GATTGGAAATATTAATCCTAGAAATGGTGATTCTA ACTACAATGAGAAGTTCAGGAGCAAGGCCTCACTG ACTGTAGACAAATCCACGAGCACAGTCTACATGGA GCTCAGTAGCCTGAGATCTGAGGACACTGCGGTCT ATTATTGTGCAAGAGGGTACTTCGATGTCTGGGGC CAAGGGACCACGGTCACCGTCTCCTCA |
| 28 | AA | VH of Hu35B6 | QVQLVQSGAEVKKPGASVKVSCKASGYTFTNYWMH WVRQAPGQGLEWIGNINPRNGDSNYNEKFRSKASL TVDKSTSTVYMELSSLRSEDTAVYYCARGYFDVWG QGTTVTVSS |
| 29 | DNA | VL of Hu35B6 | GACATCCAGATGACCCAGTCTCCATCTTCCCTGTC TGCATCTGTAGGAGACAGAGTCACTATCACTTGCA AGGCGAGTCAGGACATTAATAGCTATTTAAGCTGG TTCCAGCAGAAACCAGGGAAAGCTCCTAAGACCCT GATCTATCGTGCAAACAGATTGGTAGATGGGGTCC ACTCAAAGTTCAGTGGCAGTGGATCTGGGCAAGAT TTTACTCTCACCATCAGCAGCCTGCAGCCTGAAGA CTTTGCAACTTATTATTGTCTACAGTATGATGAGT TTCCATTCACGTTCGGCCAGGGGACAAAGTTGGAA ATCAAA |
| 30 | AA | VL of Hu35B6 | DIQMTQSPSSLSASVGDRVTITCKASQDINSYLSW FQQKPGKAPKTLIYRANRLVDGVPSKFSGSGSGQD FTLTISSLQPEDFATYYCLQYDEFPFTFGQGTKLE IK |
| 31 | DNA | Signal peptide of VH of Hu33E10 | ATGAAGTTGTGGCTGAACTGGATTTTCCTTGTAAC ACTTTTAAATGGTTTCCAGTGT |
| 32 | AA | Signal peptide of VH of Hu33E10 | *MKLWLNWIFLVTLLNGFQC* |
| 33 | DNA | Signal peptide of VL of Hu33E10 | ATGAGGACCCCTGCTCAGTTTCTTGGAATCTTGTT GCTCTGGTTTCCAGGTATCAAATGT |

| SEQ ID NO. | TYPE | DESCRIPTION | SEQUENCE |
|---|---|---|---|
| 34 | AA | Signal peptide of VL of Hu33E10 | MRTPAQFLGILLLWFPGIKC |
| 35 | DNA | Signal peptide of VH of Hu35B6 | ATGAAGTTGTGGCTGAACTGGATTTTCCTTGTAAC ACTTTTAAATGGTTTCCAGTGT |
| 36 | AA | Signal peptide of VH of Hu35B6 | MKLWLNWIFLVTLLNGFQC |
| 37 | DNA | Signal peptide of VL of Hu35B6 | ATGAGGACCCCTGCTCAGTTTCTTGGAATCTTGTT GCTCTGGTTTCCAGGTATCAAATGT |
| 38 | AA | Signal peptide of VL of Hu35B6 | MRTPAQFLGILLLWFPGIKC |
| 39 | DNA | VH of 33E10 (FERM BP-10440) | GAGGTGAAGCTGGTGGAGTCTGGAGGAGGCTTGGT ACAGCCTGGGGGTTCTCTGAGTCTCTCCTGTGCAG CTTCTGGATTCACCTTCACTGATTACTACATGATC TGGGTCCGCCAGCCTCCAGGGAAGGCACTTGAGTG GTTGGGTTTTATTAGAAACAAAGCTAATGGTTACA CAACAGAGTACAGTGCATCTGTGAAGGGTCGGTTC ACCATCTCCAGAGATAATTCCCAAAGCATCCTCTA TCTTCAAATGAATGCCCTGAGAGCTGAGGACAGTG CCACTTATTACTGTGCAAGGGGGGCTTACTGGGGC CAAGGGACTCTGGTCACTGTCTCTGCA |
| 40 | AA | VH of 33E10 (FERM BP-10440) | EVKLVESGGGLVQPGGSLSLSCAASGFTFTDYYMI WVRQPPGKALEWLGFIRNKANGYTTEYSASVKGRF TISRDNSQSILYLQMNALRAEDSATYYCARGAYWG QGTLVTVSA |
| 41 | AA | Signal peptide of VH of 33E10 | MKLWLNWIFLVTLLNGFQC |
| 42 | DNA | VL of 33E10 (FERM BP-10440) | GATGTTTTGATGACCCAAACTCCACTCTCCCTGCC TGTCAGTCTTGGAGATCAAGCCTCCATCTCTTGCA GATCTAGTCAGAGCATTGTACATAGTAATGGAAAC ACCTATTTAGAATGGTACCTGCAGAAACCAGGCCA GTCTCCAAAGCTCCTGATCTACAGAGTTTCCAACC GATTTTCTGGGGTCCCAGACAGGTTCAGTGGCAGT GGATCAGGGACAGATTTCACACTCAAGATCAGCAG AGTGGAGGCTGAGGATCTGGGAGTTTATTACTGCT TTCAAGGTTCATTTGTTCCGTGGAACGTTCGGTGG AGGCACCAAGCTGGAAATCAAA |
| 43 | AA | VL of 33E10 (FERM BP-10440) | DVLMTQTPLSLPVSLGDQASISCRSSQSIVHSNGN TYLEWYLQKPGQSPKLLIYRVSNRFSGVPDRFSGS GSGTDFTLKISRVEAEDLGVYYCFQGSFVPWTFGG GTKLEIK |
| 44 | AA | Signal peptide of VL of 33E10 | MKLPVRLLVLMFWIPASSS |
| 45 | DNA | Designed Hu33E10 VH gene including sequence encoding signal peptide, flanked by SpeI and HindIII sites (FIG. 17) | ACTAGTACCACCATGAAGTTGTGGCTGAACTGGAT TTTCCTTGTAACACTTTTAAATGGTTTCCAGTGTG AGGTGAAGCTGGTGGAGTCTGGAGGAGGCTTGGTA CAGCCTGGGGGTTCTCTGAGTCTCTCCTGTGCAGC TTCTGGATTCACCTTCACTGATTACTACATGATCT GGGTCCGCCAGCCTCCAGGGAAGGCACTTGAGTGG TTGGGTTTTATTAGAAACAAAGCTAATGGTTACAC AACAGAGTACAGTGCATCTGTGAAGGGTCGGTTCA CCATCTCCAGAGATAATTCCCAAAGCATCCTCTAT CTTCAAATGAATGCCCTGAGAGCTGAGGACAGTGC CACTTATTACTGTGCAAGGGGGGCTTACTGGGGCC AAGGGACTCTGGTCACTGTCTCTGCAGGTGAGTCC TAACTTCAAGCTT |

| SEQ ID NO. | TYPE | DESCRIPTION | SEQUENCE |
|---|---|---|---|
| 46 | AA | Designed Hu33E10 VH including sequence encoding signal peptide (FIG. 17) | MKLWLNWIFLVTLLNGFQCEVKLVESGGGLVQPGG SLSLSCAASGFTFTDYYMIWVRQPPGKALEWLGFI RNKANGYTTEYSASVKGRFTISRDNSQSILYLQMN ALRAEDSATYYCARGAYWGQGTLVTVSA |
| 47 | AA | Signal peptide of designed Hu33E10 VH | MKLWLNWIFLVTLLNGFQC |
| 48 | DNA | Designed Hu33E10 VL gene including sequence encoding signal peptide, flanked by NheI and EcoRI sites (FIG. 18) | GCTAGCACCACCATGAAGTTGCCTGTTAGGCTGTT GGTGCTGATGTTCTGGATTCCTGCTTCCAGCAGTG ATGTTTTGATGACCCAAACTCCACTCTCCCTGCCT GTCAGTCTTGGAGATCAAGCCTCCATCTCTTGCAG ATCTAGTCAGAGCATTGTACATAGTAATGGAAACA CCTATTTAGAATGGTACCTGCAGAAACCAGGCCAG TCTCCAAAGCTCCTGATCTACAGAGTTTCCAACCG ATTTTCTGGGGTCCCAGACAGGTTCAGTGGCAGTG GATCAGGGACAGATTTCACACTCAAGATCAGCAGA GTGGAGGCTGAGGATCTGGGAGTTTATTACTGCTT TCAAGGTTCATTTGTTCCGTGGACGTTCGGTGGAG GCACCAAGCTGGAAATCAAACGTAAGTAGAATCCA AAGAATTC |
| 49 | AA | Designed Hu33E10 VL including sequence encoding signal peptide (FIG. 17) | MKLPVRLLVLMFWIPASSSDVLMTQTPLSLPVSLG DQASISCRSSQSIVHSNGNTYLEWYLQKPGQSPKL LIYRVSNRFSGVPDRFSGSGSGTDFTLKISRVEAE DLGVYYCFQGSFVPWTFGGGTKLEIK |
| 50 | AA | Signal peptide of designed Hu33E10 VL | MKLPVRLLVLMFWIPASSS |
| 51 | DNA | FIG. 24 Hu33E10 VH gene flanked by SpeI and HindIII (5'-GGG & CCC-3') | GGGACTAGTACCACCATGAAGTTGTGGCTGAACTGG ATTTTCCTTGTAACACTTTTAAATGGTTTCCAGT GTGAAGTGCAGCTGGTGGAGTCTGGAGGAGGCTTG GTACAGCCTGGGGGTTCTCTGAGACTCTCCTGTGC AGCTTCTGGATTCACCTTCACTGATTACTACATGA TCTGGGTCCGCCAGGCTCCAGGGAAGGGACTTGAG TGGTTGGGTTTTATTAGAAACAAAGCTAATGGTTA CACAACAGAGTACAGTGCATCTGTGAAGGGTCGGT TCACCATCTCCAGAGATAATGCCAAGAACTCACTC TATCTTCAAATGAACTCCCTGAGAGCTGAGGACAC GGCCGTGTATTACTGTGCAAGGGGCGCTTACTGGG GCCAAGGGACTATGGTCACTGTCTCTTCAGGTAAG ATGGGCTTTCCAAGCTTCCC |
| 52 | DNA | FIG. 26 Hu33E10 VH gene flanked by SpeI and HindIII | ACTAGTACCACCATGAAGTTGTGGCTGAACTGGAT TTTCCTTGTAACACTTTTAAATGGTTTCCAGTGTG AAGTGCAGCTGGTGGAGTCTGGAGGAGGCTTGGTA CAGCCTGGGGGTTCTCTGAGACTCTCCTGTGCAGC TTCTGGATTCACCTTCACTGATTACTACATGATCT GGGTCCGCCAGGCTCCAGGGAAGGGACTTGAGTGG TTGGGTTTTATTAGAAACAAAGCTAATGGTTACAC AACAGAGTACAGTGCATCTGTGAAGGGTCGGTTCA CCATCTCCAGAGATAATGCCAAGAACTCACTCTAT CTTCAAATGAATTCCCTGAGAGCTGAGGACACGGC CGTGTATTACTGTGCAAGGGGCGCTTACTGGGGCC AAGGGACTATGGTCACTGTCTCTTCAGGTAAGATG GGCTTTCCAAGCTT |
| 53 | DNA | FIG. 25 Hu33E10 VL gene flanked by NheI and EcorI (5'-GGG & CCC-3') | GGGGCTAGCACCACCATGAGGACCCCTGCTCAGTT TCTTGGAATCTTGTTGCTCTGGTTTCCAGGTATCA AATGTGATATTGTGATGACCCAATCTCCACTCTCC CTGCCTGTCACTCCTGGAGAGCCAGCCTCCATCTC TTGCAGATCTAGTCAGAGCATTGTACATAGTAATG GAAACACCTATTTAGAATGGTACCTGCAGAAACCA GGCCAGTCTCCACAGCTCCTGATCTACAGAGTTTC CAACCGATTTTCTGGGGTCCCAGACAGGTTCAGTG GCAGTGGATCAGGGACAGATTTCACACTCAAGATC AGCAGAGTGGAGGCTGAGGATGTCGGAGTTTATTA CTGCTTTCAAGGTTCATTTGTTCCGTGGACGTTCG |

| SEQ ID NO. | TYPE | DESCRIPTION | SEQUENCE |
|---|---|---|---|
| | | | GTCAAGGCACCAAAGTGGAAATCAAAC*GTGAGTAG* *AATTTAAAGAATTCCCC* |
| 54 | DNA | FIG. 27 Hu33E10 VL gene flanked by NheI and EcorI | GCTAGCACCACCATGAGGACCCCTGCTCAGTTTCT TGGAATCTTGTTGCTCTGGTTTCCAGGTATCAAAT GTGATATTGTGATGACCCAATCTCCACTCTCCCTG CCTGTCACTCCTGGAGAGCCAGCCTCCATCTCTTG CAGATCTAGTCAGAGCATTGTACATAGTAATGGAA ACACCTATTTAGAATGGTACCTGCAGAAACCAGGC CAGTCTCCACAGCTCCTGATCTACAGAGTTTCCAA CCGATTTTCTGGGGTCCCAGACAGGTTCAGTGGCA GTGGATCAGGGACAGATTTCACACTCAAGATCAGC AGAGTGGAGGCTGAGGATGTCGGAGTTTATTACTG CTTTCAAGGTTCATTTGTTCCGTGGACGTTCGGTC AAGGCACCAAAGTGGAAATCAAAC*GTGAGTAGAAT* *TTAAAGAATTC* |
| 55 | DNA | VH of 35B6 (FERM BP-10441) | CAGGTCCAACTGCAGCAGCCTGGGACTGAACTGGT GAAGCCTGGGGCTTCAGTGAAGCTGTCCTGTAAGG CTTCTGGCTACACCTTCACCAACTACTGGATGCAC TGGGTGAAGCAGAGGCCTGGACAAGGCCTTGAGTG GATTGGAAATATTAATCCTAGAAATGGTGATTCTA ACTACAATGAGAAGTTCAGGAGCAAGGCCTCACTG ACTGTAGACAAATCCTCCAGCACAGTCTACATGCA GCTCAGTAGCCTGACATCTGAGGACTCTGCGGTCT ATTATTGTGCAAGAGGGTACTTCGATGTCTGGGGC ACAGGGACCACGGTCACCGTCTCCTCA |
| 56 | AA | VH of 35B6 (FERM BP-10440) | QVQLQQPGTELVKPGASVKLSCKASGYTFTNYWMH WVKQRPGQGLEWIGNINPRNGDSNYNEKFRSKASL TVDKSSSTVYMQLSSLTSEDSAVYYCARGYFDVWG TGTTVTVSS |
| 57 | AA | Signal peptide of VH of 35B6 | *MGWSCIILFLVAAATGVHS* |
| 58 | DNA | VL of 35B6 (FERM BP-10441) | GACATCAAGATGACCCAGTCTCCATCTTCCATGTA TGCATCTCTAGGAGAGAGAGTCTCTATCACTTGCA AGGCGAGTCAGGACATTAATAGCTATTTAAGCTGG TTCCAGCAGAAATCAGGGAAATCTCCTAAGACCCT GATCTATCGTGCAAACAGATTGGTAGATGGGGTCC CATCAAGGTTCAGTGGCAGTGGATCTGGGCAAGAT TTTTCTCTCACCATCAGCAGCCTGGAGTATGAAGA CATGGGAATTTATTATTGTCTACAGTATGATGAGT TTCCATTCACGTTCGGCTCGGGGACAAAGTTGGAA ATAAAA |
| 59 | AA | VL of 35B6 (FERM BP-10441) | DIKMTQSPSSMYASLGERVSITCKASQDINSYLSW FQQKSGKSPKTLIYRANRLVDGVPSRFSGSGSGQD FSLTISSLEYEDMGIYYCLQYDEFPFTFGSGTKLE IK |
| 60 | AA | Signal peptide of VL of 35B6 | *MRTPAQFLGILLLWFPGIKC* |
| 61 | DNA | Designed Hu35B6 VH gene including sequence encoding signal peptide, flanked by SpeI and HindIII sites (FIG. 30) | ACTAGTACCACCATGGGATGGAGCTGTATCATCCT CTTTTTGGTAGCAGCAGCTACAGGTGTCCACTCCC AGGTCCAACTGCAGCAGCCTGGGACTGAACTGGTG AAGCCTGGGGCTTCAGTGAAGCTGTCCTGTAAGGC TTCTGGCTACACCTTCACCAACTACTGGATGCACT GGGTGAAGCAGAGGCCTGGACAAGGCCTTGAGTGG ATTGGAAATATTAATCCTAGAAATGGTGATTCTAA CTACAATGAGAAGTTCAGGAGCAAGGCCTCACTGA CTGTAGACAAATCCTCCAGCACAGTCTACATGCAG CTCAGTAGCCTGACATCTGAGGACTCTGCGGTCTA TTATTGTGCAAGAGGGTACTTCGATGTCTGGGGCA CAGGGACCACGGTCACCGTCTCCTCA*GGTAAGCTG* *GCTTTTTTAAGCTT* |
| 62 | AA | Designed Hu35B6 VH including sequence encoding signal peptide (FIG. 30) | *MGWSCIILFLVAAATGVHS*QVQLQQPGTELVKPGA SVKLSCKASGYTFTNYWMHWVKQRPGQGLEWIGNI NPRNGDSNYNEKFRSKASLTVDKSSSTVYMQLSSL TSEDSAVYYCARGYFDVWGTGTTVTVSS |

| SEQ ID NO. | TYPE | DESCRIPTION | SEQUENCE |
|---|---|---|---|
| 63 | AA | Signal peptide of designed Hu35B6 VH | MGWSCIILFLVAAATGVHS |
| 64 | DNA | Designed Hu35B6 VL gene including sequence encoding signal peptide, flanked by NheI and EcoRI sites (FIG. 31) | GCTAGCACCACCATGAGGACCCCTGCTCAGTTTCT TGGAATCTTGTTGCTCTGGTTTCCAGGTATCAAAT GTGACATCAAGATGACCCAGTCTCCATCTTCCATG TATGCATCTCTAGGAGAGAGTCTCTATCACTTG CAAGGCGAGTCAGGACATTAATAGCTATTTAAGCT GGTTCCAGCAGAAATCAGGGAAATCTCCTAAGACC CTGATCTATCGTGCAAACAGATTGGTAGATGGGGT CCCATCAAGGTTCAGTGGCAGTGGATCTGGGCAAG ATTTTTCTCTCACCATCAGCAGCCTGGAGTATGAA GACATGGGAATTTATTATTGTCTACAGTATGATGA GTTTCCATTCACGTTCGGCTCGGGGACAAAGTTGG AAATAAAACGTAAGTAGACTTTTGCGAATTC |
| 65 | AA | Designed Hu35B6 VL including sequence encoding signal peptide (FIG. 31) | MRTPAQFLGILLLWFPGIKCDIKMTQSPSSMYASL GERVSITCKASQDINSYLSWFQQKSGKSPKTLIYR ANRLVDGVPSRFSGSGSGQDFSLTISSLEYEDMGI YYCLQYDEFPFTFGSGTKLEIK |
| 66 | AA | Signal peptide of designed Hu35B6 VL | MRTPAQFLGILLLWFPGIKC |
| 67 | DNA | FIG. 37 Hu35B6 VH gene flanked by SpeI and HindIII(5'-GG G & CCC-3') | GGGACTAGTACCACCATGAAGTTGTGGCTGAACTG GATTTTCCTTGTAACACTTTTAAATGGTTTCCAGT GTCAGGTCCAACTGGTGCAGTCTGGGGCTGAAGTG AAGAAGCCTGGGGCTTCAGTGAAGGTGTCCTGTAA GGCTTCTGGCTACACCTTCACCAACTACTGGATGC ACTGGGTGCGACAGGCCCCTGGACAAGGGCTTGAG TGGATTGGAAATATTAATCCTAGAAATGGTGATTC TAACTACAATGAGAAGTTCAGGAGCAAGGCCTCAC TGACTGTAGACAAATCCACGAGCACAGTCTACATG GAGCTCAGTAGCCTGAGATCTGAGGACACTGCGGT CTATTATTGTGCAAGAGGGTACTTCGATGTCTGGG GCCAAGGGACCACGGTCACCGTCTCCTCAGGTAAG AATGGCCACTCAAGCTTCCC |
| 68 | DNA | FIG. 39 Hu33E10 VH gene flanked by SpeI and HindIII | ACTAGTACCACCATGAAGTTGTGGCTGAACTGGAT TTTCCTTGTAACACTTTTAAATGGTTTCCAGTGTC AGGTCCAACTGGTGCAGTCTGGGGCTGAAGTGAAG AAGCCTGGGGCTTCAGTGAAGGTGTCCTGTAAGGC TTCTGGCTACACCTTCACCAACTACTGGATGCACT GGGTGCGACAGGCCCCTGGACAAGGGCTTGAGTGG ATTGGAAATATTAATCCTAGAAATGGTGATTCTAA CTACAATGAGAAGTTCAGGAGCAAGGCCTCACTGA CTGTAGACAAATCCACGAGCACAGTCTACATGGAG CTCAGTAGCCTGAGATCTGAGGACACTGCGGTCTA TTATTGTGCAAGAGGGTACTTCGATGTCTGGGGCC AAGGGACCACGGTCACCGTCTCCTCAGGTAAGAAT GGCCACTCAAGCTT |
| 69 | DNA | FIG. 38 Hu35B6 VL gene flanked by NheI and EcoRI (5'-GGG & CCC-3') | GGGGCTAGCACCACCATGAGGACCCCTGCTCAGTT CTTTGGAATCTTGTTGCTCTGGTTTCCAGGTATCA TAAGTGACATCCAGATGACCCAGTCTCCATCTTCC CTGTCTGCATCTGTAGGAGACAGAGTCACTATCAC TTGCAAGGCGAGTCAGGACATTAATAGCTATTTAA GCTGGTTCCAGCAGAAACCAGGGAAAGCTCCTAAG ACCCTGATCTATCGTGCAAACAGATTGGTAGATGG GGTCCCATCAAGGTTCAGTGGCAGTGGATCTGGGC AAGATTTTACTCTCACCATCAGCAGCCTGCAGCCT GAAGACTTTGCAACTTATTATTGTCTACAGTATGA TTGAGTTTCCATCACGTTCGGCCAGGGGACAAAGT TGGAAATCAAACGTGAGTAGAATTTAAAGAATTCC CC |
| 70 | DNA | FIG. 40 Hu33E10 VL gene flanked by SpeI and HindIII | GCTAGCACCACCATGAGGACCCCTGCTCAGTTTCT TGGAATCTTGTTGCTCTGGTTTCCAGGTATCAAAT GTGACATCCAGATGACCCAGTCTCCATCTTCCCTG TCTGCATCTGTAGGAGACAGAGTCACTATCACTTG CAAGGCGAGTCAGGACATTAATAGCTATTTAAGCT CGGTTCAGCAGAAACCAGGGAAAGCTCCTAAGACC |

| SEQ ID NO. | TYPE | DESCRIPTION | SEQUENCE |
|---|---|---|---|
| | | | CTGATCTATCGTGCAAACAGATTGGTAGATGGGGT CCCATCAAAGTTCAGTGGCAGTGGATCTGGGCAAG ATTTTACTCTCACCATCAGCAGCCTGCAGCCTGAA GACTTTGCAACTTATTATTGTCTACAGTATGATGA GTTTCCATTCACGTTCGGCCAGGGGACAAAGTTGG AAATCAAACGTGAGTAGAATTTAAAGAATTC |
| 71 | AA | Partial aa sequence of mOPN (Synthetic peptide) | (C)VDVPNGRGDSLAYGLR |
| 72 | AA | Partial aa sequence of mOPN (Synthetic peptide) | (C)SLAYGLR |
| 73 | AA | Partial aa sequence of mOPN (Synthetic peptide) | (C)LPVKTDSGSSEEKLY |
| 74 | AA | Partial aa sequence of mOPN (Synthetic peptide) | (C)VDVPNGRGDS |
| 75 | AA | Partial aa sequence of mOPN (Synthetic peptide) | (C)PNGRGD |
| 76 | AA | Partial aa sequence of mOPN (Synthetic peptide) | (C)GRGDSLAYGLR |
| 77 | AA | Partial aa sequence of mOPN (Synthetic peptide) | (C)GDSLAYG |
| 78 | AA | Partial aa sequence of mOPN (Synthetic peptide) | (C)GDSLAYGLR |
| 79 | AA | Partial aa sequence of hOPN (Synthetic peptide) | (C)VDTYDGRGDSVVYGLRS |
| 80 | AA | Partial aa sequence of hOPN (Synthetic peptide) | (C)SVVYGLR |
| 81 | AA | Partial aa sequence of mOPN and hOPN (Synthetic peptide) | (C)GRGDS |
| 82 | DNA | 5' RACE primer | GCCAGTGGATAGACTGATGG |

-continued

| SEQ ID NO. | TYPE | DESCRIPTION | SEQUENCE |
|---|---|---|---|
| 83 | DNA | 5' RACE primer | GATGGATACAGTTGGTGCAGC |
| 84 | DNA | Gene Racer 5' primer | CGACTGGAGCACGAGGACACTGA |
| 85 | DNA | 33E10 VH 3' primer | GCCAGTGGATAGACAGATGG |
| 86 | DNA | 33E10 VL 3' primer | GATGGATACAGTTGGTGCAGC |
| 87 | DNA | 33E10 VH 5' primer | GGGACTAGTACCACCATGAAGTTGTGGCTGAACTG GATT |
| 88 | DNA | 33E10 VH 3' primer | GGGAAGCTTGAAGTTAGGACTCACCTGCAGAGACA GTGACCAGAGTCCC |
| 89 | DNA | 33E10 VH 5' primer | GGGGGCTAGCACCACCATGAAGTTGCCTGTTAGGCT GTTG |
| 90 | DNA | 33E10 VH 3' primer | GGGGAATTCTTTGGATTCTACTTACGTTTGATTTC CAGCTTGGTGCCTCC |
| 91 | DNA | JNJ220 | GGGACTAGTACCACCATGAAG |
| 92 | DNA | JNJ206 | GGGACTAGTACCACCATGAAGTTGTGGCTGAACTG GATTTTCCTTGTAACACTT |
| 93 | DNA | JNJ207 | CAGCTGCACTTCACACTGGAAACCATTTAAAAGTG TTACAAGGAAAATCCA |
| 94 | DNA | JNJ208 | TTCCAGTGTGAAGTGCAGCTGGTGGAGTCTGGAGG AGGCTTGGTACAGCCT |
| 95 | DNA | JNJ209 | AGCTGCACAGGAGAGTCTCAGAGAACCCCCAGGCT GTACCAAGCCTCCTCC |
| 96 | DNA | JNJ210 | CTGAGACTCTCCTGTGCAGCTTCTGGATTCACCTT CACTGATTACTACATG |
| 97 | DNA | JNJ211 | TCCCTTCCCTGGAGCCTGGCGGACCCAGATCATGT AGTAATCAGTGAAGGT |
| 98 | DNA | JNJ212 | CGCCAGGCTCCAGGGAAGGGACTTGAGTGGTTGGG TTTTATTAGAAACAAA |
| 99 | DNA | JNJ213 | TGCACTGTACTCTGTTGTGTAACCATTAGCTTTGT TTCTAATAAAACCCAA |
| 100 | DNA | JNJ214 | TACACAACAGAGTACAGTGCATCTGTGAAGGGTCG GTTCACCATCTCCAGA |
| 101 | DNA | JNJ215 | TTGAAGATAGAGTGAGTTCTTGGCATTATCTCTGG AGATGGTGAACCGACC |
| 102 | DNA | JNJ216 | AAGAACTCACTCTATCTTCAAATGAACTCCCTGAG AGCTGAGGACACGGCC |
| 103 | DNA | JNJ217 | CCAGTAAGCGCCCCTTGCACAGTAATACACGGCCG TGTCCTCAGCTCTCAG |
| 104 | DNA | JNJ218 | TGTGCAAGGGGCGCTTACTGGGGCCAAGGGACTAT GGTCACTGTCTCTTCA |
| 105 | DNA | JNJ219 | GGGAAGCTTGGAAAGCCCATCTTACCTGAAGAGAC AGTGACCATAGT |
| 106 | DNA | JNJ221 | GGGAAGCTTGGAAAGCCCATC |
| 107 | DNA | JNJ116 | GGGCTAGCACCACCATGAGG |
| 108 | DNA | JNJ193 | GGGCTAGCACCACCATGAGGACCCCTGCTCAGTTT CTTGGAATCTTGTTGCTC |
| 109 | DNA | JNJ194 | CACAATATCACATTTGATACCTGGAAACCAGAGCA ACAAGATTCCAAGAAA |

-continued

| SEQ ID NO. | TYPE | DESCRIPTION | SEQUENCE |
|---|---|---|---|
| 110 | DNA | JNJ195 | GGTATCAAATGTGATATTGTGATGACCCAATCTCCACTCTCCCTGCCTGTC |
| 111 | DNA | JNJ196 | GCAAGAGATGGAGGCTGGCTCTCCAGGAGTGACAGGCAGGGAGAGTGGAGA |
| 112 | DNA | JNJ197 | GAGCCAGCCTCCATCTCTTGCAGATCTAGTCAGAGCATTGTACATAGTAAT |
| 113 | DNA | JNJ198 | CTGCAGGTACCATTCTAAATAGGTGTTTCCATTACTATGTACAATGCTCTG |
| 114 | DNA | JNJ199 | TATTTAGAATGGTACCTGCAGAAACCAGGCCAGTCTCCACAGCTCCTGATC |
| 115 | DNA | JNJ200 | GACCCCAGAAAATCGGTTGGAAACTCTGTAGATCAGGAGCTGTGGAGACTG |
| 116 | DNA | JNJ201 | TCCAACCGATTTTCTGGGGTCCCAGACAGGTTCAGTGGCAGTGGATCAGGG |
| 117 | DNA | JNJ202 | CACTCTGCTGATCTTGAGTGTGAAATCTGTCCCTGATCCACTGCCACTGAA |
| 118 | DNA | JNJ203 | ACACTCAAGATCAGCAGAGTGGAGGCTGAGGATGTCGGAGTTTATTACTGC |
| 119 | DNA | JNJ204 | GAACGTCCACGGAACAAATGAACCTTGAAAGCAGTAATAAACTCCGACATC |
| 120 | DNA | JNJ205 | TCATTTGTTCCGTGGACGTTCGGTCAAGGCACCAAAGTGGAAATCAAACGTGAGTAG |
| 121 | DNA | JNJ206 | GGGACTAGTACCACCATGAAGTTGTGGCTGAACTGGATTTTCCTTGTAACACTT |
| 122 | DNA | JNJ101 | GGGGAATTCTTTAAATTCTACTCACGTTTGATTTCCA |
| 123 | DNA | JNJ117 | GGGGAATTCTTTAAATTCTA |
| 124 | DNA | 35B6 VH 3' primer | GCCAGTGGATAGACAGATGG |
| 125 | DNA | 35B6 VL 3' primer | GATGGATACAGTTGGTGCAGC |
| 126 | DNA | 35B6 VH 5' primer | GGGACTAGTACCACCATGGGATGGAGCTGTATCCTC |
| 127 | DNA | 35B6 VH 3' primer | GGGAAGCTTAAAAAAAGCCAGCTTACCTGAGGAGACGGTGACCGTGGTCCC |
| 128 | DNA | 35B6 VH 5' primer | GGGGCTAGCACCACCATGAGGACCCCTGCTCAGTTTCTT |
| 129 | DNA | 35B6 VH 3' primer | GGGGAATTCGCAAAAGTACTTACGTTTTATTTCCAACTTTGTCCCCGA |
| 130 | DNA | JNJ234 | CAGTTGGACCTGACACTGGAAACCATTTAAAAGTGTTACAAGGAAAATCCA |
| 131 | DNA | JNJ235 | TTCCAGTGTCAGGTCCAACTGGTGCAGTCTGGGGCTGAAGTGAAGAAGCCT |
| 132 | DNA | JNJ236 | AGCCTTACAGGACACCTTCACTGAAGCCCCAGGCTTCTTCACTTCAGCCCC |
| 133 | DNA | JNJ237 | GTGAAGGTGTCCTGTAAGGCTTCTGGCTACACCTTCACCAACTACTGGATG |
| 134 | DNA | JNJ238 | GCCTTGTCCAGGGGCCTGTCGCACCCAGTGCATCCAGTAGTTGGTGAAGGT |
| 135 | DNA | JNJ239 | CGACAGGCCCCTGGACAAGGCCTTGAGTGGATTGGAAATATTAATCCTAGA |

| SEQ ID NO. | TYPE | DESCRIPTION | SEQUENCE |
|---|---|---|---|
| 136 | DNA | JNJ240 | GAACTTCTCATTGTAGTTAGAATCACCATTTCTAG GATTAATATTTCCAAT |
| 137 | DNA | JNJ241 | TCTAACTACAATGAGAAGTTCAGGAGCAAGGCCTC ACTGACTGTAGACAAA |
| 138 | DNA | JNJ242 | ACTGAGCTCCATGTAGACTGTGCTCGTGGATTTGT CTACAGTCAGTGAGGC |
| 139 | DNA | JNJ243 | ACAGTCTACATGGAGCTCAGTAGCCTGAGATCTGA GGACACTGCGGTCTAT |
| 140 | DNA | JNJ244 | CCAGACATCGAAGTACCCTCTTGCACAATAATAGA CCGCAGTGTCCTCAGA |
| 141 | DNA | JNJ245 | AGAGGGTACTTCGATGTCTGGGGCCAAGGGACCAC GGTCACCGTCTCCTCA |
| 142 | DNA | JNJ246 | GGGAAGCTTGAGTGGCCATTCTTACCTGAGGAGAC GGTGACCGTGGT |
| 143 | DNA | JNJ247 | GGGAAGCTTGAGTGGCCATTC |
| 144 | DNA | JNJ222 | CTGGATGTCACATTTGATACCTGGAAACCAGAGCA ACAAGATTCCAAGAAA |
| 145 | DNA | JNJ223 | GGTATCAAATGTGACATCCAGATGACCCAGTCTCC ATCTTCCCTGTCTGCA |
| 146 | DNA | JNJ224 | GCAAGTGATAGTGACTCTGTCTCCTACAGATGCAG ACAGGGAAGATGGAGA |
| 147 | DNA | JNJ225 | GACAGAGTCACTATCACTTGCAAGGCGAGTCAGGA CATTAATAGCTATTTA |
| 148 | DNA | JNJ226 | AGCTTTCCCTGGTTTCTGCTGGAACCAGCTTAAAT AGCTATTAATGTCCTG |
| 149 | DNA | JNJ227 | CAGCAGAAACCAGGGAAAGCTCCTAAGACCCTGAT CTATCGTGCAAACAGA |
| 150 | DNA | JNJ228 | ACTGAACTTTGATGGGACCCCATCTACCAATCTGT TTGCACGATAGATCAG |
| 151 | DNA | JNJ229 | GGGGTCCCATCAAAGTTCAGTGGCAGTGGATCTGG GCAAGATTTTACTCTC |
| 152 | DNA | JNJ230 | AAAGTCTTCAGGCTGCAGGCTGCTGATGGTGAGAG TAAAATCTTGCCCAGA |
| 153 | DNA | JNJ231 | AGCCTGCAGCCTGAAGACTTTGCAACTTATTATTG TCTACAGTATGATGAG |
| 154 | DNA | JNJ232 | CTTTGTCCCCTGGCCGAACGTGAATGGAAACTCAT CATACTGTAGACAATA |
| 155 | DNA | JNJ233 | ACGTTCGGCCAGGGGACAAAGTTGGAAATCAAACG TGAGTAGAA |

What is claimed is:

1. A humanized antibody or an antigen-binding fragment thereof that immunospecifically recognizes the RGD sequence, comprising:
(i) a H-chain comprising FRH1-4 of a VH of a human antibody, and the amino acid sequences of SEQ ID NOS: 1, 2 and 3 as CDRH1, CDRH2 and CDRH3 respectively; and
(i) a L-chain comprising FRL1-4 of a VL of a human antibody, and the amino acid sequences of SEQ ID NOS: 4, 5 and 6 as CDRL1, CDRL2 and CDRL3 respectively, wherein said FRH1-4 consists of the amino acid sequences of SEQ ID NOS: 14, 15, 16 and 17, respectively, and said FRL1-4 consists of the amino acid sequences of SEQ ID NOS: 19, 20, 21 and 22, respectively.

2. The humanized antibody or the antigen-binding fragment thereof of claim 1, wherein said VH comprises the amino acid sequence of SEQ ID NO: 24, and said VL comprises the amino acid sequence of SEQ ID NO: 26.

3. A humanized antibody or an antigen-binding fragment thereof that immunospecifically recognizes the RGD sequence, comprising:
(ii) a H-chain comprising FRH1-4 of a VH of a human antibody, and the amino acid sequences of SEQ ID NOS: 7, 8 and 9 as CDRH1, CDRH2 and CDRH3 respectively; and
(ii) a L-chain comprising FRL1-4 of a VL of a human antibody, and the amino acid sequences of SEQ ID NOS: 10, 11 and 12 as CDRL1, CDRL2 and CDRL3 respectively, wherein said FRH1-4 consists of the amino acid sequences of SEQ ID NOS: 14, 15, 16 and 17, respectively, and said FRL1-4 consists of the amino acid sequences of SEQ ID NOS: 19, 20, 21 and 22, respectively.

4. The humanized antibody or the antigen-binding fragment thereof of claim 3, wherein said VH comprises the amino acid sequence of SEQ ID NO: 28, and said VL comprises the amino acid sequence of SEQ ID NO: 30.

5. A pharmaceutical composition for treating endometriosis comprising the humanized antibody or an antigen-binding fragment thereof of claim 1, and a pharmaceutically acceptable carrier.

6. A pharmaceutical composition for treating endometriosis comprising the humanized antibody or an antigen-binding fragment thereof of claim 3, and a pharmaceutically acceptable carrier.

7. A method for preventing or treating endometriosis comprising:
   administering an effective amount of the humanized antibody or an antigen-binding fragment thereof of claim 1 to a subject in need thereof.

8. A method for preventing or treating endometriosis comprising:
   administering an effective amount of the humanized antibody or an antigen-binding fragment thereof of claim 3 to a subject in need thereof.

9. The humanized antibody or antigen-binding fragment thereof of claim 1, wherein said FRH1-4 comprise the amino acid sequences of SEQ ID NOS: 14, 15, 16 and 17, respectively, and said FRL1-4 comprise the amino acid sequences of SEQ ID NOS: 19, 20, 21 and 22, respectively.

10. The humanized antibody or antigen-binding fragment thereof of claim 3, wherein said FRH1-4 comprise the amino acid sequences of SEQ ID NOS: 14, 15, 16 and 17, respectively, and said FRL1-4 comprise the amino acid sequences of SEQ ID NOS: 19, 20, 21 and 22, respectively.

* * * * *

UNITED STATES PATENT AND TRADEMARK OFFICE
CERTIFICATE OF CORRECTION

PATENT NO.        : 8,614,296 B2
APPLICATION NO. : 12/989208
DATED             : December 24, 2013
INVENTOR(S)       : Kumar et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 122 days.

Signed and Sealed this
Twenty-second Day of September, 2015

Michelle K. Lee
*Director of the United States Patent and Trademark Office*

SEQUENCE LISTING

<160> NUMBER OF SEQ ID NOS: 195

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic peptide -continued

```
<400> SEQUENCE: 1

Gly Phe Thr Phe Thr Asp Tyr Tyr Met Ile
1               5                   10

<210> SEQ ID NO 2
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Leu Gly Phe Ile Arg Asn Lys Ala Asn Gly Tyr Thr Thr Glu Tyr
1               5                   10                  15

Ser Ala Ser Val Lys Gly
            20

<210> SEQ ID NO 3
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ala Tyr
1

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Ser Gln Ser Ile Val His Ser Asn Gly Asn Thr Tyr Leu Glu
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Val Ser Asn Arg Phe Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Phe Val Pro Trp
1               5
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Thr Asn Tyr Trp Met His
1               5                   10

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ile Gly Asn Ile Asn Pro Arg Asn Gly Asp Ser Asn Tyr Asn Glu
1               5                   10                  15

Lys Phe Arg Ser
            20

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Phe Asp Val
1               5

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ala Ser Gln Asp Ile Asn Ser Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Asn Arg Leu Val Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 12

Tyr Asp Glu Phe Pro Phe
1               5

<210> SEQ ID NO 13
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
atggactgga cctggagggt cctcttttttg gtggcagcag ccacaggtgc ccactcccag    60
gtccagcttg tgcagtctgg ggctgaggtg aagaagcctg gggcctcagt gaaggtttcc   120
tgcaaggctt ctggatacac cttcactagc tatgctatgc attgggtgcg ccaggccccc   180
ggacaaaggc ttgagtggat gggatggatc aacgctggca atggtaacac aaaatattca   240
cagaagttcc agggcagagt caccattacc agggacacat ccgcgagcac agcctacatg   300
gagctgagca gcctgagatc tgaagacacg gctgtgtatt actgtgcgag aatacccgt    360 attagcagtg gctggttggg ggactacttt gactactggg gccagggaac cctggtcacc   420
gtctcctca                                                            429
```

<210> SEQ ID NO 14
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Val Arg Gln Ala Pro Gly Gln Arg Leu Glu Trp Met Gly
1               5                   10

<210> SEQ ID NO 16
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Trp Gly Gln Gly Thr Leu Val Thr Val Ser Ser
1               5                   10

<210> SEQ ID NO 18
<211> LENGTH: 370
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
cgctcagctc ctggggctcc tgctactctg gctccgaggt gccagatgtg acatccagat      60
gacccagtct ccatcctccc tgtctgcatc tgtaggagac agagtcacca tcacttgccg     120
ggcaagtcag agcattagca gctatttaaa ttggtatcag cagaaaccag ggaaagcccc     180
taagctcctg atctatgctg catccagttt gcaaagtggg gtcccatcaa ggttcagtgg     240
cagtggatct gggacagatt tcactctcac catcagcagt ctgcaacctg aagattttgc     300
aacttactac tgtcaacaga gttacagtac ccctcggacg ttcggccaag ggaccaaggt     360
ggaaatcaaa                                                            370

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Tyr Gln Gln Lys Pro Gly Lys Ala Pro Lys Leu Leu Ile Tyr
1               5                   10                  15

<210> SEQ ID NO 21
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Gly Gln Gly Thr Lys Val Glu Ile Lys
1               5                   10

<210> SEQ ID NO 23
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gaagtgcagc tggtggagtc tggaggaggc ttggtacagc ctggggggttc tctgagactc     60 tcctgtgcag cttctggatt caccttcact gattactaca tgatctgggt ccgccaggct    120
ccagggaagg gacttgagtg gttgggtttt attagaaaca agctaatgg ttacacaaca     180 gagtacagtg catctgtgaa gggtcggttc accatctcca gagataatgc caagaactca    240
ctctatcttc aaatgaattc cctgagagct gaggacacgg ccgtgtatta ctgtgcaagg    300
ggcgcttact gggggccaagg gactatggtc actgtctctt ca                      342

<210> SEQ ID NO 24
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ile Trp Val Arg Gln Ala Pro Gly Lys Gly Leu Glu Trp Leu
        35                  40                  45

Gly Arg Phe Thr Ile Ser Arg Asp Asn Ala Lys Asn Ser Leu Tyr Leu
    50                  55                  60

Gln Met Asn Ser Leu Arg Ala Glu Asp Thr Ala Val Tyr Tyr Cys Ala
65                  70                  75                  80

Arg Gly Ala Tyr Trp Gly Gln Gly Thr Met Val Thr Val Ser Ser
                85                  90                  95

<210> SEQ ID NO 25
<211> LENGTH: 336
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 25
gatattgtga tgacccaatc tccactctcc ctgcctgtca ctcctggaga gccagcctcc      60
atctcttgca gatctagtca gagcattgta catagtaatg gaaacaccta tttagaatgg     120
tacctgcaga aaccaggcca gtctccacag ctcctgatct acagagtttc aaccgattt      180 tctggggtcc cagacaggtt cagtggcagt ggatcaggga cagatttcac actcaagatc     240
agcagagtgg aggctgagga tgtcggagtt tattactgct ttcaaggttc atttgttccg     300
tggacgttcg gtcaaggcac caaagtggaa atcaaa                                336

<210> SEQ ID NO 26
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Phe Val Pro Trp Thr Phe Gly Gln Gly Thr Lys Val Glu Ile Lys
            100                 105                 110

<210> SEQ ID NO 27
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
caggtccaac tggtgcagtc tggggctgaa gtgaagaagc tggggcttc agtgaaggtg        60 tcctgtaagg cttctggcta caccttcacc aactactgga tgcactgggt gcgacaggcc     120
cctggacaag gcttgagtg gattggaaat attaatccta gaaatggtga ttctaactac      180
aatgagaagt tcaggagcaa ggcctcactg actgtagaca atccacgag cacagtctac      240 atggagctca gtagcctgag atctgaggac actgcggtct attattgtgc aagagggtac     300
ttcgatgtct ggggccaagg gaccacggtc accgtctcct ca                         342

<210> SEQ ID NO 28
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
            20                  25                  30
Trp Met His Trp Val Arg Gln Ala Pro Gly Gln Gly Leu Glu Trp Ile
        35                  40                  45
Gly Asn Ile Asn Pro Arg Asn Gly Asp Ser Asn Tyr Asn Glu Lys Phe
    50                  55                  60
Arg Ser Lys Ala Ser Leu Thr Val Asp Lys Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Tyr Phe Asp Val Trp Gly Gln Gly Thr Thr Val Thr Val
            100                 105                 110
Ser Ser

<210> SEQ ID NO 29
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gacatccaga tgacccagtc tccatcttcc ctgtctgcat ctgtaggaga cagagtcact    60
atcacttgca aggcgagtca ggacattaat agctatttaa ctggttccaa gcagaaacca   120
gggaaagctc ctaagaccct gatctatcgt gcaaacagat tggtagatgg ggtcccatca   180
aagttcagtg gcagtggatc tgggcaagat tttactctca ccatcagcag cctgcagcct   240
gaagactttg caacttatta ttgtctacag tatgatgagt ttccattcac gttcggccag   300
gggacaaagt tggaaatcaa a                                             321

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Ile Asn Ser Tyr
            20                  25                  30
Leu Ser Trp Phe Gln Gln Lys Pro Gly Lys Ala Pro Lys Thr Leu Ile
        35                  40                  45
Tyr Arg Ala Asn Arg Leu Val Asp Gly Val Pro Ser Lys Phe Ser Gly
    50                  55                  60
Ser Gly Ser Gly Gln Asp Phe Thr Leu Thr Ile Ser Ser Leu Gln Pro
65                  70                  75                  80
Glu Asp Phe Ala Thr Tyr Tyr Cys Leu Gln Tyr Asp Glu Phe Pro Phe
                85                  90                  95
Thr Phe Gly Gln Gly Thr Lys Leu Glu Ile Lys
            100                 105

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
atgaagttgt ggctgaactg gattttcctt gtaacactt taaatggttt ccagtgt         57

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Met Lys Leu Trp Leu Asn Trp Ile Phe Leu Val Thr Leu Leu Asn Gly
1               5                   10                  15

Phe Gln Cys

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
atgaggaccc ctgctcagtt tcttggaatc ttgttgctct ggtttccagg tatcaaatgt     60

<210> SEQ ID NO 34
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Met Arg Thr Pro Ala Gln Phe Leu Gly Ile Leu Leu Leu Trp Phe Pro
1               5                   10                  15

Gly Ile Lys Cys
            20

<210> SEQ ID NO 35
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
atgaagttgt ggctgaactg gattttcctt gtaacactt taaatggttt ccagtgt         57

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Met Lys Leu Trp Leu Asn Trp Ile Phe Leu Val Thr Leu Leu Asn Gly
1               5                   10                  15

Phe Gln Cys

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgaggaccc ctgctcagtt tcttggaatc ttgttgctct ggtttccagg tatcaaatgt      60

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Arg Thr Pro Ala Gln Phe Leu Gly Ile Leu Leu Leu Trp Phe Pro
1               5                   10                  15

Gly Ile Lys Cys
            20

<210> SEQ ID NO 39
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtgaagc tggtggagtc tggaggaggc ttggtacagc ctgggggttc tctgagtctc      60
tcctgtgcag cttctggatt caccttcact gattactaca tgatctgggt ccgccagcct     120
ccagggaagg cacttgagtg gttgggtttt attagaaaca agctaatgg ttacacaaca      180 gagtacagtg catctgtgaa gggtcggttc accatctcca gagataattc ccaaagcatc     240
ctctatcttc aaatgaatgc cctgagagct gaggacagtg ccacttatta ctgtgcaagg     300
ggggcttact ggggccaagg gactctggtc actgtctctg ca                       342

<210> SEQ ID NO 40
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ile Trp Val Arg Gln Pro Pro Gly Lys Ala Leu Glu Trp Leu

```
                35                  40                  45
Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asn Ser Gln Ser Ile
 65                  70                  75                  80

Leu Tyr Leu Gln Met Asn Ala Leu Arg Ala Glu Asp Ser Ala Thr Tyr
                 85                  90                  95

Tyr Cys Ala Arg Gly Ala Tyr Trp Gly Gln Gly Thr Leu Val Thr Val
            100                 105                 110

Ser Ala

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Met Lys Leu Trp Leu Asn Trp Ile Phe Leu Val Thr Leu Leu Asn Gly
 1               5                  10                  15

Phe Gln Cys

<210> SEQ ID NO 42
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gatgttttga tgacccaaac tccactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acagagtttc aaccgatttt     180
tctggggtcc cagacaggtt cagtggcagt ggatcaggga cagatttcac actcaagatc     240
agcagagtgg aggctgagga tctgggagtt tattactgct ttcaaggttc atttgttccg     300
tggacgttcg gtggaggcac caagctggaa atcaaa                                336

<210> SEQ ID NO 43
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
             20                  25                  30

Asn Gly Asn Thr Tyr Leu Glu Trp Tyr Leu Gln Lys Pro Gly Gln Ser
         35                  40                  45

Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Tyr Cys Phe Gln Gly
                85                  90                  95

Ser Phe Val Pro Trp Thr Phe Gly Gly Gly Thr Lys Leu Glu Ile Lys
            100                 105                 110

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Met Lys Leu Pro Val Arg Leu Leu Val Leu Met Phe Trp Ile Pro Ala
1               5                   10                  15

Ser Ser Ser

<210> SEQ ID NO 45
<211> LENGTH: 433
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(411)

<400> SEQUENCE: 45
actagtacca cc atg aag ttg tgg ctg aac tgg att ttc ctt gta aca ctt     51
              Met Lys Leu Trp Leu Asn Trp Ile Phe Leu Val Thr Leu
                1               5                   10 tta aat ggt ttc cag tgt gag gtg aag ctg gtg gag tct gga gga ggc      99
Leu Asn Gly Phe Gln Cys Glu Val Lys Leu Val Glu Ser Gly Gly Gly
        15                  20                  25 ttg gta cag cct ggg ggt tct ctg agt ctc tcc tgt gca gct tct gga     147
Leu Val Gln Pro Gly Gly Ser Leu Ser Leu Ser Cys Ala Ala Ser Gly
30                  35                  40                  45 ttc acc ttc act gat tac tac atg atc tgg gtc cgc cag cct cca ggg     195
Phe Thr Phe Thr Asp Tyr Tyr Met Ile Trp Val Arg Gln Pro Pro Gly
                50                  55                  60 aag gca ctt gag tgg ttg ggt ttt att aga aac aaa gct aat ggt tac     243
Lys Ala Leu Glu Trp Leu Gly Phe Ile Arg Asn Lys Ala Asn Gly Tyr
            65                  70                  75 aca aca gag tac agt gca tct gtg aag ggt cgg ttc acc atc tcc aga     291
Thr Thr Glu Tyr Ser Ala Ser Val Lys Gly Arg Phe Thr Ile Ser Arg
        80                  85                  90 gat aat tcc caa agc atc ctc tat ctt caa atg aat gcc ctg aga gct     339
Asp Asn Ser Gln Ser Ile Leu Tyr Leu Gln Met Asn Ala Leu Arg Ala
    95                  100                 105 gag gac agt gcc act tat tac tgt gca agg ggg gct tac tgg ggc caa     387
Glu Asp Ser Ala Thr Tyr Tyr Cys Ala Arg Gly Ala Tyr Trp Gly Gln
110                 115                 120                 125 ggg act ctg gtc act gtc tct gca ggtgagtcct aacttcaagc tt            433
Gly Thr Leu Val Thr Val Ser Ala
                130

<210> SEQ ID NO 46
<211> LENGTH: 133
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 46

Met Lys Leu Trp Leu Asn Trp Ile Phe Leu Val Thr Leu Leu Asn Gly
1               5                   10                  15

Phe Gln Cys Glu Val Lys Leu Val Glu Ser Gly Gly Gly Leu Val Gln
            20                  25                  30

Pro Gly Gly Ser Leu Ser Leu Ser Cys Ala Ala Ser Gly Phe Thr Phe
        35                  40                  45

Thr Asp Tyr Tyr Met Ile Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

Gln Ser Ile Leu Tyr Leu Gln Met Asn Ala Leu Arg Ala Glu Asp Ser
            100                 105                 110

Ala Thr Tyr Tyr Cys Ala Arg Gly Ala Tyr Trp Gly Gln Gly Thr Leu
        115                 120                 125

Val Thr Val Ser Ala
    130

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Lys Leu Trp Leu Asn Trp Ile Phe Leu Val Thr Leu Leu Asn Gly
1               5                   10                  15

Phe Gln Cys

<210> SEQ ID NO 48
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(405)

<400> SEQUENCE: 48
gctagcacca cc atg aag ttg cct gtt agg ctg ttg gtg ctg atg ttc tgg      51
           Met Lys Leu Pro Val Arg Leu Leu Val Leu Met Phe Trp
           1               5                   10 att cct gct tcc agc agt gat gtt ttg atg acc caa act cca ctc tcc       99
Ile Pro Ala Ser Ser Ser Asp Val Leu Met Thr Gln Thr Pro Leu Ser
    15                  20                  25 ctg cct gtc agt ctt gga gat caa gcc tcc atc tct tgc aga tct agt       147
Leu Pro Val Ser Leu Gly Asp Gln Ala Ser Ile Ser Cys Arg Ser Ser
30                  35                  40                  45 cag agc att gta cat agt aat gga aac acc tat tta gaa tgg tac ctg       195
Gln Ser Ile Val His Ser Asn Gly Asn Thr Tyr Leu Glu Trp Tyr Leu
                50                  55                  60 cag aaa cca ggc cag tct cca aag ctc ctg atc tac aga gtt tcc aac       243
Gln Lys Pro Gly Gln Ser Pro Lys Leu Leu Ile Tyr Arg Val Ser Asn
            65                  70                  75

```
cga ttt tct ggg gtc cca gac agg ttc agt ggc agt gga tca ggg aca    291
Arg Phe Ser Gly Val Pro Asp Arg Phe Ser Gly Ser Gly Ser Gly Thr
        80                  85                  90 gat ttc aca ctc aag atc agc aga gtg gag gct gag gat ctg gga gtt    339
Asp Phe Thr Leu Lys Ile Ser Arg Val Glu Ala Glu Asp Leu Gly Val
     95                 100                 105 tat tac tgc ttt caa ggt tca ttt gtt ccg tgg acg ttc ggt gga ggc    387
Tyr Tyr Cys Phe Gln Gly Ser Phe Val Pro Trp Thr Phe Gly Gly Gly
110                 115                 120                 125 acc aag ctg gaa atc aaa cgtaagtaga atccaaagaa ttc                  428
Thr Lys Leu Glu Ile Lys
                130
```

<210> SEQ ID NO 49
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Arg Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser Phe Val Pro Trp Thr Phe Gly Gly Gly Thr Lys Leu
        115                 120                 125

Glu Ile Lys
        130
```

<210> SEQ ID NO 50
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Met Lys Leu Pro Val Arg Leu Leu Val Leu Met Phe Trp Ile Pro Ala
1               5                   10                  15

Ser Ser Ser
```

<210> SEQ ID NO 51
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

```
<221> NAME/KEY: CDS
<222> LOCATION: (16)..(414)

<400> SEQUENCE: 51
gggactagta ccacc atg aag ttg tgg ctg aac tgg att ttc ctt gta aca      51
                 Met Lys Leu Trp Leu Asn Trp Ile Phe Leu Val Thr
                  1               5                  10 ctt tta aat ggt ttc cag tgt gaa gtg cag ctg gtg gag tct gga gga      99
Leu Leu Asn Gly Phe Gln Cys Glu Val Gln Leu Val Glu Ser Gly Gly
            15                  20                  25 ggc ttg gta cag cct ggg ggt tct ctg aga ctc tcc tgt gca gct tct     147
Gly Leu Val Gln Pro Gly Gly Ser Leu Arg Leu Ser Cys Ala Ala Ser
 30                  35                  40 gga ttc acc ttc act gat tac tac atg atc tgg gtc cgc cag gct cca     195
Gly Phe Thr Phe Thr Asp Tyr Tyr Met Ile Trp Val Arg Gln Ala Pro
45                  50                  55                  60 ggg aag gga ctt gag tgg ttg ggt ttt att aga aac aaa gct aat ggt     243
Gly Lys Gly Leu Glu Trp Leu Gly Phe Ile Arg Asn Lys Ala Asn Gly
                 65                  70                  75 tac aca aca gag tac agt gca tct gtg aag ggt cgg ttc acc atc tcc     291
Tyr Thr Thr Glu Tyr Ser Ala Ser Val Lys Gly Arg Phe Thr Ile Ser
                 80                  85                  90 aga gat aat gcc aag aac tca ctc tat ctt caa atg aac tcc ctg aga     339
Arg Asp Asn Ala Lys Asn Ser Leu Tyr Leu Gln Met Asn Ser Leu Arg
             95                 100                 105 gct gag gac acg gcc gtg tat tac tgt gca agg ggc gct tac tgg ggc     387
Ala Glu Asp Thr Ala Val Tyr Tyr Cys Ala Arg Gly Ala Tyr Trp Gly
        110                 115                 120 caa ggg act atg gtc act gtc tct tca ggtaagatgg ctttccaag cttccc     440
Gln Gly Thr Met Val Thr Val Ser Ser
125                 130

<210> SEQ ID NO 52
<211> LENGTH: 434
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(411)

<400> SEQUENCE: 52
actagtacca cc atg aag ttg tgg ctg aac tgg att ttc ctt gta aca ctt      51
              Met Lys Leu Trp Leu Asn Trp Ile Phe Leu Val Thr Leu
               1               5                  10 tta aat ggt ttc cag tgt gaa gtg cag ctg gtg gag tct gga gga ggc      99
Leu Asn Gly Phe Gln Cys Glu Val Gln Leu Val Glu Ser Gly Gly Gly
            15                  20                  25 ttg gta cag cct ggg ggt tct ctg aga ctc tcc tgt gca gct tct gga     147
Leu Val Gln Pro Gly Gly Ser Leu Arg Leu Ser Cys Ala Ala Ser Gly
 30                  35                  40                  45 ttc acc ttc act gat tac tac atg atc tgg gtc cgc cag gct cca ggg     195
Phe Thr Phe Thr Asp Tyr Tyr Met Ile Trp Val Arg Gln Ala Pro Gly
                 50                  55                  60 aag gga ctt gag tgg ttg ggt ttt att aga aac aaa gct aat ggt tac     243
Lys Gly Leu Glu Trp Leu Gly Phe Ile Arg Asn Lys Ala Asn Gly Tyr
             65                  70                  75 aca aca gag tac agt gca tct gtg aag ggt cgg ttc acc atc tcc aga     291
Thr Thr Glu Tyr Ser Ala Ser Val Lys Gly Arg Phe Thr Ile Ser Arg
         80                  85                  90 gat aat gcc aag aac tca ctc tat ctt caa atg aat tcc ctg aga gct     339
```

```
Asp Asn Ala Lys Asn Ser Leu Tyr Leu Gln Met Asn Ser Leu Arg Ala
 95                 100                 105 gag gac acg gcc gtg tat tac tgt gca agg ggc gct tac tgg ggc caa      387
Glu Asp Thr Ala Val Tyr Tyr Cys Ala Arg Gly Ala Tyr Trp Gly Gln
110                 115                 120                 125 ggg act atg gtc act gtc tct tca ggtaagatgg ctttccaag ctt              434
Gly Thr Met Val Thr Val Ser Ser
                130

<210> SEQ ID NO 53
<211> LENGTH: 437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(411)

<400> SEQUENCE: 53
ggggctagca ccacc atg agg acc cct gct cag ttt ctt gga atc ttg ttg      51
                Met Arg Thr Pro Ala Gln Phe Leu Gly Ile Leu Leu
                  1               5                  10 ctc tgg ttt cca ggt atc aaa tgt gat att gtg atg acc caa tct cca      99
Leu Trp Phe Pro Gly Ile Lys Cys Asp Ile Val Met Thr Gln Ser Pro
         15                  20                  25 ctc tcc ctg cct gtc act cct gga gag cca gcc tcc atc tct tgc aga     147
Leu Ser Leu Pro Val Thr Pro Gly Glu Pro Ala Ser Ile Ser Cys Arg
 30                  35                  40 tct agt cag agc att gta cat agt aat gga aac acc tat tta gaa tgg     195
Ser Ser Gln Ser Ile Val His Ser Asn Gly Asn Thr Tyr Leu Glu Trp
45                  50                  55                  60 tac ctg cag aaa cca ggc cag tct cca cag ctc ctg atc tac aga gtt     243
Tyr Leu Gln Lys Pro Gly Gln Ser Pro Gln Leu Leu Ile Tyr Arg Val
                 65                  70                  75 tcc aac cga ttt tct ggg gtc cca gac agg ttc agt ggc agt gga tca     291
Ser Asn Arg Phe Ser Gly Val Pro Asp Arg Phe Ser Gly Ser Gly Ser
             80                  85                  90 ggg aca gat ttc aca ctc aag atc agc aga gtg gag gct gag gat gtc     339
Gly Thr Asp Phe Thr Leu Lys Ile Ser Arg Val Glu Ala Glu Asp Val
         95                 100                 105 gga gtt tat tac tgc ttt caa ggt tca ttt gtt ccg tgg acg ttc ggt     387
Gly Val Tyr Tyr Cys Phe Gln Gly Ser Phe Val Pro Trp Thr Phe Gly
     110                 115                 120 caa ggc acc aaa gtg gaa atc aaa cgtgagtaga atttaaagaa ttcccc        437
Gln Gly Thr Lys Val Glu Ile Lys
125                 130

<210> SEQ ID NO 54
<211> LENGTH: 431
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(408)

<400> SEQUENCE: 54
gctagcacca cc atg agg acc cct gct cag ttt ctt gga atc ttg ttg ctc    51
              Met Arg Thr Pro Ala Gln Phe Leu Gly Ile Leu Leu Leu
                1               5                  10 tgg ttt cca ggt atc aaa tgt gat att gtg atg acc caa tct cca ctc      99
Trp Phe Pro Gly Ile Lys Cys Asp Ile Val Met Thr Gln Ser Pro Leu
```

```
                 Trp Phe Pro Gly Ile Lys Cys Asp Ile Val Met Thr Gln Ser Pro Leu
                     15                  20                  25 tcc ctg cct gtc act cct gga gag cca gcc tcc atc tct tgc aga tct                147
Ser Leu Pro Val Thr Pro Gly Glu Pro Ala Ser Ile Ser Cys Arg Ser
 30                  35                  40                  45 agt cag agc att gta cat agt aat gga aac acc tat tta gaa tgg tac                195
Ser Gln Ser Ile Val His Ser Asn Gly Asn Thr Tyr Leu Glu Trp Tyr
                     50                  55                  60 ctg cag aaa cca ggc cag tct cca cag ctc ctg atc tac aga gtt tcc                243
Leu Gln Lys Pro Gly Gln Ser Pro Gln Leu Leu Ile Tyr Arg Val Ser
                 65                  70                  75 aac cga ttt tct ggg gtc cca gac agg ttc agt ggc agt gga tca ggg                291
Asn Arg Phe Ser Gly Val Pro Asp Arg Phe Ser Gly Ser Gly Ser Gly
         80                  85                  90 aca gat ttc aca ctc aag atc agc aga gtg gag gct gag gat gtc gga                339
Thr Asp Phe Thr Leu Lys Ile Ser Arg Val Glu Ala Glu Asp Val Gly
     95                 100                 105 gtt tat tac tgc ttt caa ggt tca ttt gtt ccg tgg acg ttc ggt caa                387
Val Tyr Tyr Cys Phe Gln Gly Ser Phe Val Pro Trp Thr Phe Gly Gln
110                 115                 120                 125 ggc acc aaa gtg gaa atc aaa cgtgagtaga atttaaagaa ttc                          431
Gly Thr Lys Val Glu Ile Lys
                    130

<210> SEQ ID NO 55
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
caggtccaac tgcagcagcc tgggactgaa ctggtgaagc ctggggcttc agtgaagctg        60
tcctgtaagg cttctggcta caccttcacc aactactgga tgcactgggt gaagcagagg       120
cctggacaag gccttgagtg gattggaaat attaatccta gaaatggtga ttctaactac       180
aatgagaagt tcaggagcaa ggcctcactg actgtagaca atcctccag cacagtctac        240 atgcagctca gtagcctgac atctgaggac tctgcggtct attattgtgc aagagggtac       300
ttcgatgtct ggggcacagg gaccacggtc accgtctcct ca                          342

<210> SEQ ID NO 56
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Gln Gln Pro Gly Thr Glu Leu Val Lys Pro Gly Ala
 1               5                  10                  15

Ser Val Lys Leu Ser Cys Lys Ala Ser Gly Tyr Thr Phe Thr Asn Tyr
             20                  25                  30

Trp Met His Trp Val Lys Gln Arg Pro Gly Gln Gly Leu Glu Trp Ile
         35                  40                  45

Gly Asn Ile Asn Pro Arg Asn Gly Asp Ser Asn Tyr Asn Glu Lys Phe
     50                  55                  60

Arg Ser Lys Ala Ser Leu Thr Val Asp Lys Ser Ser Thr Val Tyr
 65                  70                  75                  80
```

```
Met Gln Leu Ser Ser Leu Thr Ser Glu Asp Ser Ala Val Tyr Tyr Cys
                85                  90                  95

Ala Arg Gly Tyr Phe Asp Val Trp Gly Thr Gly Thr Thr Val Thr Val
            100                 105                 110

Ser Ser

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Met Gly Trp Ser Cys Ile Ile Leu Phe Leu Val Ala Ala Ala Thr Gly
1               5                   10                  15

Val His Ser

<210> SEQ ID NO 58
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
gacatcaaga tgacccagtc tccatcttcc atgtatgcat ctctaggaga gagagtctct      60
atcacttgca aggcgagtca ggacattaat agctatttaa gctggttcca gcagaaatca     120
gggaaatctc ctaagaccct gatctatcgt gcaaacagat tggtagatgg ggtcccatca     180
aggttcagtg gcagtggatc tgggcaagat ttttctctca ccatcagcag cctggagtat     240
gaagacatgg gaatttatta ttgtctacag tatgatgagt ttccattcac gttcggctcg     300
gggacaaagt tggaaataaa a                                               321

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Lys Met Thr Gln Ser Pro Ser Ser Met Tyr Ala Ser Leu Gly
1               5                   10                  15

Glu Arg Val Ser Ile Thr Cys Lys Ala Ser Gln Asp Ile Asn Ser Tyr
            20                  25                  30

Leu Ser Trp Phe Gln Gln Lys Ser Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Ser Leu Thr Ile Ser Ser Leu Glu Tyr
65                  70                  75                  80

Glu Asp Met Gly Ile Tyr Tyr Cys Leu Gln Tyr Asp Glu Phe Pro Phe
                85                  90                  95

Thr Phe Gly Ser Gly Thr Lys Leu Glu Ile Lys
            100                 105
```

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Met Arg Thr Pro Ala Gln Phe Leu Gly Ile Leu Leu Leu Trp Phe Pro
1               5                   10                  15

Gly Ile Lys Cys
            20

<210> SEQ ID NO 61
<211> LENGTH: 434
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (13)..(411)

<400> SEQUENCE: 61
actagtacca cc atg gga tgg agc tgt atc atc ctc ttt ttg gta gca gca         51
              Met Gly Trp Ser Cys Ile Ile Leu Phe Leu Val Ala Ala
              1               5                   10 gct aca ggt gtc cac tcc cag gtc caa ctg cag cag cct ggg act gaa           99
Ala Thr Gly Val His Ser Gln Val Gln Leu Gln Gln Pro Gly Thr Glu
    15                  20                  25 ctg gtg aag cct ggg gct tca gtg aag ctg tcc tgt aag gct tct ggc          147
Leu Val Lys Pro Gly Ala Ser Val Lys Leu Ser Cys Lys Ala Ser Gly
30                  35                  40                  45 tac acc ttc acc aac tac tgg atg cac tgg gtg aag cag agg cct gga          195
Tyr Thr Phe Thr Asn Tyr Trp Met His Trp Val Lys Gln Arg Pro Gly
                50                  55                  60 caa ggc ctt gag tgg att gga aat att aat cct aga aat ggt gat tct          243
Gln Gly Leu Glu Trp Ile Gly Asn Ile Asn Pro Arg Asn Gly Asp Ser
            65                  70                  75 aac tac aat gag aag ttc agg agc aag gcc tca ctg act gta gac aaa          291
Asn Tyr Asn Glu Lys Phe Arg Ser Lys Ala Ser Leu Thr Val Asp Lys
        80                  85                  90 tcc tcc agc aca gtc tac atg cag ctc agt agc ctg aca tct gag gac          339
Ser Ser Ser Thr Val Tyr Met Gln Leu Ser Ser Leu Thr Ser Glu Asp
    95                  100                 105 tct gcg gtc tat tat tgt gca aga ggg tac ttc gat gtc tgg ggc aca          387
Ser Ala Val Tyr Tyr Cys Ala Arg Gly Tyr Phe Asp Val Trp Gly Thr
110                 115                 120                 125 ggg acc acg gtc acc gtc tcc tca ggtaagctgg ctttttttaag ctt              434
Gly Thr Thr Val Thr Val Ser Ser
                130

<210> SEQ ID NO 62
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Met Gly Trp Ser Cys Ile Ile Leu Phe Leu Val Ala Ala Ala Thr Gly
1               5                   10                  15

```
Val His Ser Gln Val Gln Leu Gln Gln Pro Gly Thr Glu Leu Val Lys
         20                  25                  30

Pro Gly Ala Ser Val Lys Leu Ser Cys Lys Ala Ser Gly Tyr Thr Phe
         35                  40                  45

Thr Asn Tyr Trp Met His Trp Val Lys Gln Arg Pro Gly Gln Gly Leu
 50                  55                  60

Glu Trp Ile Gly Asn Ile Asn Pro Arg Asn Gly Asp Ser Asn Tyr Asn
 65                  70                  75                  80

Glu Lys Phe Arg Ser Lys Ala Ser Leu Thr Val Asp Lys Ser Ser Ser
                 85                  90                  95

Thr Val Tyr Met Gln Leu Ser Ser Leu Thr Ser Glu Asp Ser Ala Val
             100                 105                 110

Tyr Tyr Cys Ala Arg Gly Tyr Phe Asp Val Trp Gly Thr Gly Thr Thr
         115                 120                 125

Val Thr Val Ser Ser
        130

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Gly Trp Ser Cys Ile Ile Leu Phe Leu Val Ala Ala Ala Thr Gly
1               5                   10                  15

Val His Ser

<210> SEQ ID NO 64
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(393)

<400> SEQUENCE: 64
gctagcacca cc atg agg acc cct gct cag ttt ctt gga atc ttg ttg ctc      51
              Met Arg Thr Pro Ala Gln Phe Leu Gly Ile Leu Leu Leu
              1               5                   10 tgg ttt cca ggt atc aaa tgt gac atc aag atg acc cag tct cca tct       99
Trp Phe Pro Gly Ile Lys Cys Asp Ile Lys Met Thr Gln Ser Pro Ser
 15                  20                  25 tcc atg tat gca tct cta gga gag aga gtc tct atc act tgc aag gcg      147
Ser Met Tyr Ala Ser Leu Gly Glu Arg Val Ser Ile Thr Cys Lys Ala
 30                  35                  40                  45 agt cag gac att aat agc tat tta agc tgg ttc cag cag aaa tca ggg      195
Ser Gln Asp Ile Asn Ser Tyr Leu Ser Trp Phe Gln Gln Lys Ser Gly
                 50                  55                  60 aaa tct cct aag acc ctg atc tat cgt gca aac aga ttg gta gat ggg      243
Lys Ser Pro Lys Thr Leu Ile Tyr Arg Ala Asn Arg Leu Val Asp Gly
             65                  70                  75 gtc cca tca agg ttc agt ggc agt gga tct ggg caa gat ttt tct ctc      291
Val Pro Ser Arg Phe Ser Gly Ser Gly Ser Gly Gln Asp Phe Ser Leu
         80                  85                  90 acc atc agc agc ctg gag tat gaa gac atg gga att tat tat tgt cta      339
Thr Ile Ser Ser Leu Glu Tyr Glu Asp Met Gly Ile Tyr Tyr Cys Leu
```

93                                              94
                                                                -continued 95                  100                 105
cag tat gat gag ttt cca ttc acg ttc ggc tcg ggg aca aag ttg gaa      387
Gln Tyr Asp Glu Phe Pro Phe Thr Phe Gly Ser Gly Thr Lys Leu Glu
110                 115                 120                 125 ata aaa cgtaagtaga cttttgcgaa ttc                                    416
Ile Lys <210> SEQ ID NO 65
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Arg Thr Pro Ala Gln Phe Leu Gly Ile Leu Leu Leu Trp Phe Pro
1               5                   10                  15

Gly Ile Lys Cys Asp Ile Lys Met Thr Gln Ser Pro Ser Ser Met Tyr
            20                  25                  30

Ala Ser Leu Gly Glu Arg Val Ser Ile Thr Cys Lys Ala Ser Gln Asp
        35                  40                  45

Ile Asn Ser Tyr Leu Ser Trp Phe Gln Gln Lys Ser Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Phe Ser Leu Thr Ile Ser
                85                  90                  95

Ser Leu Glu Tyr Glu Asp Met Gly Ile Tyr Tyr Cys Leu Gln Tyr Asp
            100                 105                 110

Glu Phe Pro Phe Thr Phe Gly Ser Gly Thr Lys Leu Glu Ile Lys
        115                 120                 125

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Arg Thr Pro Ala Gln Phe Leu Gly Ile Leu Leu Leu Trp Phe Pro
1               5                   10                  15

Gly Ile Lys Cys
            20

<210> SEQ ID NO 67
<211> LENGTH: 440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(414)

<400> SEQUENCE: 67
gggactagta ccacc atg aag ttg tgg ctg aac tgg att ttc ctt gta aca     51
                 Met Lys Leu Trp Leu Asn Trp Ile Phe Leu Val Thr
                 1               5                   10 ctt tta aat ggt ttc cag tgt cag gtc caa ctg gtg cag tct ggg gct     99

```
Leu Leu Asn Gly Phe Gln Cys Gln Val Gln Leu Val Gln Ser Gly Ala
        15                  20                  25 gaa gtg aag aag cct ggg gct tca gtg aag gtg tcc tgt aag gct tct         147
Glu Val Lys Lys Pro Gly Ala Ser Val Lys Val Ser Cys Lys Ala Ser
    30                  35                  40 ggc tac acc ttc acc aac tac tgg atg cac tgg gtg cga cag gcc cct         195
Gly Tyr Thr Phe Thr Asn Tyr Trp Met His Trp Val Arg Gln Ala Pro
45                  50                  55                  60 gga caa ggg ctt gag tgg att gga aat att aat cct aga aat ggt gat         243
Gly Gln Gly Leu Glu Trp Ile Gly Asn Ile Asn Pro Arg Asn Gly Asp
                65                  70                  75 tct aac tac aat gag aag ttc agg agc aag gcc tca ctg act gta gac         291
Ser Asn Tyr Asn Glu Lys Phe Arg Ser Lys Ala Ser Leu Thr Val Asp
            80                  85                  90 aaa tcc acg agc aca gtc tac atg gag ctc agt agc ctg aga tct gag         339
Lys Ser Thr Ser Thr Val Tyr Met Glu Leu Ser Ser Leu Arg Ser Glu
        95                 100                 105 gac act gcg gtc tat tat tgt gca aga ggg tac ttc gat gtc tgg ggc         387
Asp Thr Ala Val Tyr Tyr Cys Ala Arg Gly Tyr Phe Asp Val Trp Gly
    110                 115                 120 caa ggg acc acg gtc acc gtc tcc tca ggtaagaatg gccactcaag cttccc        440
Gln Gly Thr Thr Val Thr Val Ser Ser
125                 130

<210> SEQ ID NO 68
<211> LENGTH: 434
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(411)

<400> SEQUENCE: 68
actagtacca cc atg aag ttg tgg ctg aac tgg att ttc ctt gta aca ctt       51
              Met Lys Leu Trp Leu Asn Trp Ile Phe Leu Val Thr Leu
              1               5                  10 tta aat ggt ttc cag tgt cag gtc caa ctg gtg cag tct ggg gct gaa         99
Leu Asn Gly Phe Gln Cys Gln Val Gln Leu Val Gln Ser Gly Ala Glu
        15                  20                  25 gtg aag aag cct ggg gct tca gtg aag gtg tcc tgt aag gct tct ggc         147
Val Lys Lys Pro Gly Ala Ser Val Lys Val Ser Cys Lys Ala Ser Gly
    30                  35                  40                  45 tac acc ttc acc aac tac tgg atg cac tgg gtg cga cag gcc cct gga         195
Tyr Thr Phe Thr Asn Tyr Trp Met His Trp Val Arg Gln Ala Pro Gly
                50                  55                  60 caa ggg ctt gag tgg att gga aat att aat cct aga aat ggt gat tct         243
Gln Gly Leu Glu Trp Ile Gly Asn Ile Asn Pro Arg Asn Gly Asp Ser
            65                  70                  75 aac tac aat gag aag ttc agg agc aag gcc tca ctg act gta gac aaa         291
Asn Tyr Asn Glu Lys Phe Arg Ser Lys Ala Ser Leu Thr Val Asp Lys
        80                  85                  90 tcc acg agc aca gtc tac atg gag ctc agt agc ctg aga tct gag gac         339
Ser Thr Ser Thr Val Tyr Met Glu Leu Ser Ser Leu Arg Ser Glu Asp
    95                 100                 105 act gcg gtc tat tat tgt gca aga ggg tac ttc gat gtc tgg ggc caa         387
Thr Ala Val Tyr Tyr Cys Ala Arg Gly Tyr Phe Asp Val Trp Gly Gln
110                 115                 120                 125 ggg acc acg gtc acc gtc tcc tca ggtaagaatg gccactcaag ctt              434
Gly Thr Thr Val Thr Val Ser Ser
                130
```

<210> SEQ ID NO 69
<211> LENGTH: 422
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(396)

<400> SEQUENCE: 69

```
ggggctagca ccacc atg agg acc cct gct cag ttt ctt gga atc ttg ttg        51
                Met Arg Thr Pro Ala Gln Phe Leu Gly Ile Leu Leu
                  1               5                  10 ctc tgg ttt cca ggt atc aaa tgt gac atc cag atg acc cag tct cca         99
Leu Trp Phe Pro Gly Ile Lys Cys Asp Ile Gln Met Thr Gln Ser Pro
         15                  20                  25 tct tcc ctg tct gca tct gta gga gac aga gtc act atc act tgc aag        147
Ser Ser Leu Ser Ala Ser Val Gly Asp Arg Val Thr Ile Thr Cys Lys
     30                  35                  40 gcg agt cag gac att aat agc tat tta agc tgg ttc cag cag aaa cca        195
Ala Ser Gln Asp Ile Asn Ser Tyr Leu Ser Trp Phe Gln Gln Lys Pro
 45                  50                  55                  60 ggg aaa gct cct aag acc ctg atc tat cgt gca aac aga ttg gta gat        243
Gly Lys Ala Pro Lys Thr Leu Ile Tyr Arg Ala Asn Arg Leu Val Asp
                 65                  70                  75 ggg gtc cca tca aag ttc agt ggc agt gga tct ggg caa gat ttt act        291
Gly Val Pro Ser Lys Phe Ser Gly Ser Gly Ser Gly Gln Asp Phe Thr
             80                  85                  90 ctc acc atc agc agc ctg cag cct gaa gac ttt gca act tat tat tgt        339
Leu Thr Ile Ser Ser Leu Gln Pro Glu Asp Phe Ala Thr Tyr Tyr Cys
         95                 100                 105 cta cag tat gat gag ttt cca ttc acg ttc ggc cag ggg aca aag ttg        387
Leu Gln Tyr Asp Glu Phe Pro Phe Thr Phe Gly Gln Gly Thr Lys Leu
    110                 115                 120 gaa atc aaa cgtgagtaga atttaaagaa ttcccc                              422
Glu Ile Lys
125
```

<210> SEQ ID NO 70
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (13)..(393)

<400> SEQUENCE: 70

```
gctagcacca cc atg agg acc cct gct cag ttt ctt gga atc ttg ttg ctc       51
              Met Arg Thr Pro Ala Gln Phe Leu Gly Ile Leu Leu Leu
                1               5                  10 tgg ttt cca ggt atc aaa tgt gac atc cag atg acc cag tct cca tct         99
Trp Phe Pro Gly Ile Lys Cys Asp Ile Gln Met Thr Gln Ser Pro Ser
     15                  20                  25 tcc ctg tct gca tct gta gga gac aga gtc act atc act tgc aag gcg        147
Ser Leu Ser Ala Ser Val Gly Asp Arg Val Thr Ile Thr Cys Lys Ala
 30                  35                  40                  45 agt cag gac att aat agc tat tta agc tgg ttc cag cag aaa cca ggg        195
Ser Gln Asp Ile Asn Ser Tyr Leu Ser Trp Phe Gln Gln Lys Pro Gly
                 50                  55                  60
```

```
aaa gct cct aag acc ctg atc tat cgt gca aac aga ttg gta gat ggg      243
Lys Ala Pro Lys Thr Leu Ile Tyr Arg Ala Asn Arg Leu Val Asp Gly
            65                  70                  75 gtc cca tca aag ttc agt ggc agt gga tct ggg caa gat ttt act ctc      291
Val Pro Ser Lys Phe Ser Gly Ser Gly Ser Gly Gln Asp Phe Thr Leu
        80                  85                  90 acc atc agc agc ctg cag cct gaa gac ttt gca act tat tat tgt cta      339
Thr Ile Ser Ser Leu Gln Pro Glu Asp Phe Ala Thr Tyr Tyr Cys Leu
        95                 100                 105 cag tat gat gag ttt cca ttc acg ttc ggc cag ggg aca aag ttg gaa      387
Gln Tyr Asp Glu Phe Pro Phe Thr Phe Gly Gln Gly Thr Lys Leu Glu
110                 115                 120                 125 atc aaa cgtgagtaga atttaaagaa ttc                                    416
Ile Lys
```

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 71

```
Cys Val Asp Val Pro Asn Gly Arg Gly Asp Ser Leu Ala Tyr Gly Leu
1               5                   10                  15

Arg
```

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 72

```
Cys Ser Leu Ala Tyr Gly Leu Arg
1               5
```

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 73

```
Cys Leu Pro Val Lys Thr Asp Ser Gly Ser Ser Glu Glu Lys Leu Tyr
1               5                   10                  15
```

<210> SEQ ID NO 74
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 74

Cys Val Asp Val Pro Asn Gly Arg Gly Asp Ser
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 75

Cys Pro Asn Gly Arg Gly Asp
1               5

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 76

Cys Gly Arg Gly Asp Ser Leu Ala Tyr Gly Leu Arg
1               5                   10

<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 77

Cys Gly Asp Ser Leu Ala Tyr Gly
1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
```

<400> SEQUENCE: 78

Cys Gly Asp Ser Leu Ala Tyr Gly Leu Arg
1               5                   10

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 79

Cys Val Asp Thr Tyr Asp Gly Arg Gly Asp Ser Val Val Tyr Gly Leu
1               5                   10                  15

Arg Ser

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 80

Cys Ser Val Val Tyr Gly Leu Arg
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present

<400> SEQUENCE: 81

Cys Gly Arg Gly Asp Ser
1               5

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gccagtggat agactgatgg                                           20

<210> SEQ ID NO 83
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 83
gatggataca gttggtgcag c                                               21

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cgactggagc acgaggacac tga                                             23

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gccagtggat agacagatgg                                                 20

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
gatggataca gttggtgcag c                                               21

<210> SEQ ID NO 87
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gggactagta ccaccatgaa gttgtggctg aactggatt                            39

<210> SEQ ID NO 88
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gggaagcttg aagttaggac tcacctgcag agacagtgac cagagtccc                 49

<210> SEQ ID NO 89
<211> LENGTH: 39
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 89
ggggctagca ccaccatgaa gttgcctgtt aggctgttg                                    39

<210> SEQ ID NO 90
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggggaattct ttggattcta cttacgtttg atttccagct tggtgcctcc                        50

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gggactagta ccaccatgaa g                                                       21

<210> SEQ ID NO 92
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gggactagta ccaccatgaa gttgtggctg aactggattt ccttgtaac actt                    54

<210> SEQ ID NO 93
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
cagctgcact tcacactgga aaccatttaa aagtgttaca aggaaaatcc a                      51

<210> SEQ ID NO 94
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ttccagtgtg aagtgcagct ggtggagtct ggaggaggct tggtacagcc t                      51

<210> SEQ ID NO 95
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 95
agctgcacag gagagtctca gagaacccc aggctgtacc aagcctcctc c            51

<210> SEQ ID NO 96
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
ctgagactct cctgtgcagc ttctggattc accttcactg attactacat g            51

<210> SEQ ID NO 97
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
tcccttccct ggagcctggc ggacccagat catgtagtaa tcagtgaagg t            51

<210> SEQ ID NO 98
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
cgccaggctc cagggaaggg acttgagtgg ttgggtttta ttagaaacaa a            51

<210> SEQ ID NO 99
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tgcactgtac tctgttgtgt aaccattagc tttgtttcta ataaaaccca a            51

<210> SEQ ID NO 100
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tacacaacag agtacagtgc atctgtgaag ggtcggttca ccatctccag a            51

<210> SEQ ID NO 101
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101

-continued ttgaagatag agtgagttct tggcattatc tctggagatg gtgaaccgac c         51

<210> SEQ ID NO 102
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
aagaactcac tctatcttca aatgaactcc ctgagagctg aggacacggc c         51

<210> SEQ ID NO 103
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
ccagtaagcg ccccttgcac agtaatacac ggccgtgtcc tcagctctca g         51

<210> SEQ ID NO 104
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
tgtgcaaggg gcgcttactg gggccaaggg actatggtca ctgtctcttc a         51

<210> SEQ ID NO 105
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gggaagcttg gaaagcccat cttacctgaa gagacagtga ccatagt              47

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gggaagcttg gaaagcccat c                                          21

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gggctagcac caccatgagg                                            20

<210> SEQ ID NO 108
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gggctagcac caccatgagg acccctgctc agtttcttgg aatcttgttg ctc            53

<210> SEQ ID NO 109
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
cacaatatca catttgatac ctggaaacca gagcaacaag attccaagaa a              51

<210> SEQ ID NO 110
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggtatcaaat gtgatattgt gatgacccaa tctccactct ccctgcctgt c              51

<210> SEQ ID NO 111
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcaagagatg gaggctggct ctccaggagt gacaggcagg gagagtggag a              51

<210> SEQ ID NO 112
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gagccagcct ccatctcttg cagatctagt cagagcattg tacatagtaa t              51

<210> SEQ ID NO 113
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
ctgcaggtac cattctaaat aggtgtttcc attactatgt acaatgctct g              51

<210> SEQ ID NO 114

```
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tatttagaat ggtacctgca gaaaccaggc cagtctccac agctcctgat c           51

<210> SEQ ID NO 115
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gaccccagaa aatcggttgg aaactctgta gatcaggagc tgtggagact g           51

<210> SEQ ID NO 116
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tccaaccgat tttctggggt cccagacagg ttcagtggca gtggatcagg g           51

<210> SEQ ID NO 117
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cactctgctg atcttgagtg tgaaatctgt ccctgatcca ctgccactga a           51

<210> SEQ ID NO 118
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
acactcaaga tcagcagagt ggaggctgag gatgtcggag tttattactg c           51

<210> SEQ ID NO 119
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gaacgtccac ggaacaaatg aaccttgaaa gcagtaataa actccgacat c           51

<210> SEQ ID NO 120
<211> LENGTH: 57
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 120
tcatttgttc cgtggacgtt cggtcaaggc accaaagtgg aaatcaaacg tgagtag        57

<210> SEQ ID NO 121
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
gggactagta ccaccatgaa gttgtggctg aactggattt tccttgtaac actt           54

<210> SEQ ID NO 122
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
ggggaattct ttaaattcta ctcacgtttg atttcca                              37

<210> SEQ ID NO 123
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
ggggaattct ttaaattcta                                                 20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gccagtggat agacagatgg                                                 20

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gatggataca gttggtgcag c                                               21

<210> SEQ ID NO 126
<211> LENGTH: 36
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 126
gggactagta ccaccatggg atggagctgt atcctc                                    36

<210> SEQ ID NO 127
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
gggaagctta aaaaaagcca gcttacctga ggagacggtg accgtggtcc c                   51

<210> SEQ ID NO 128
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
ggggctagca ccaccatgag gaccccctgct cagtttctt                                39

<210> SEQ ID NO 129
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggggaattcg caaaagtcta cttacgtttt atttccaact ttgtccccga                     50

<210> SEQ ID NO 130
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
cagttggacc tgacactgga aaccatttaa aagtgttaca aggaaaatcc a                   51

<210> SEQ ID NO 131
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ttccagtgtc aggtccaact ggtgcagtct ggggctgaag tgaagaagcc t                   51

<210> SEQ ID NO 132
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 132
agccttacag gacaccttca ctgaagcccc aggcttcttc acttcagccc c        51

<210> SEQ ID NO 133
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtgaaggtgt cctgtaaggc ttctggctac accttcacca actactggat g        51

<210> SEQ ID NO 134
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gccttgtcca ggggcctgtc gcacccagtg catccagtag ttggtgaagg t        51

<210> SEQ ID NO 135
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cgacaggccc ctggacaagg ccttgagtgg attggaaata ttaatcctag a        51

<210> SEQ ID NO 136
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gaacttctca ttgtagttag aatcaccatt tctaggatta atatttccaa t        51

<210> SEQ ID NO 137
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tctaactaca atgagaagtt caggagcaag gcctcactga ctgtagacaa a        51

<210> SEQ ID NO 138
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
```

```
actgagctcc atgtagactg tgctcgtgga tttgtctaca gtcagtgagg c        51
```

<210> SEQ ID NO 139
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139

```
acagtctaca tggagctcag tagcctgaga tctgaggaca ctgcggtcta t        51
```

<210> SEQ ID NO 140
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140

```
ccagacatcg aagtaccctc ttgcacaata atagaccgca gtgtcctcag a        51
```

<210> SEQ ID NO 141
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141

```
agagggtact tcgatgtctg gggccaaggg accacggtca ccgtctcctc a        51
```

<210> SEQ ID NO 142
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142

```
gggaagcttg agtggccatt cttacctgag gagacggtga ccgtggt            47
```

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143

```
gggaagcttg agtggccatt c                                        21
```

<210> SEQ ID NO 144
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144

```
ctggatgtca catttgatac ctggaaacca gagcaacaag attccaagaa a        51
```

```
<210> SEQ ID NO 145
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
ggtatcaaat gtgacatcca gatgacccag tctccatctt ccctgtctgc a            51

<210> SEQ ID NO 146
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
gcaagtgata gtgactctgt ctcctacaga tgcagacagg gaagatggag a            51

<210> SEQ ID NO 147
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
gacagagtca ctatcacttg caaggcgagt caggacatta atagctattt a            51

<210> SEQ ID NO 148
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
agctttccct ggtttctgct ggaaccagct taaatagcta ttaatgtcct g            51

<210> SEQ ID NO 149
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
cagcagaaac cagggaaagc tcctaagacc ctgatctatc gtgcaaacag a            51

<210> SEQ ID NO 150
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
actgaacttt gatgggaccc catctaccaa tctgtttgca cgatagatca g            51
```

```
<210> SEQ ID NO 151
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
ggggtcccat caaagttcag tggcagtgga tctgggcaag attttactct c          51

<210> SEQ ID NO 152
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
aaagtcttca ggctgcaggc tgctgatggt gagagtaaaa tcttgcccag a          51

<210> SEQ ID NO 153
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
agcctgcagc ctgaagactt tgcaacttat tattgtctac agtatgatga g          51

<210> SEQ ID NO 154
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ctttgtcccc tggccgaacg tgaatggaaa ctcatcatac tgtagacaat a          51

<210> SEQ ID NO 155
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
acgttcggcc aggggacaaa gttggaaatc aaacgtgagt agaa             44

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Gly Asp Ser Leu Ala Tyr Gly Leu Arg
1               5                   10

<210> SEQ ID NO 157
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Val Asp Val Pro Asn Gly Arg Gly Asp Ser Leu Ala Tyr Gly Leu
1               5                   10                  15

Arg

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Leu Ala Tyr Gly Leu Arg
1               5

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Leu Pro Val Lys Thr Asp Ser Gly Ser Ser Glu Glu Lys Leu Tyr
1               5                   10                  15

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Cys Val Asp Val Pro Asn Gly Arg Gly Asp Ser
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Pro Asn Gly Arg Gly Asp
1               5

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162
```

Cys Gly Arg Gly Asp Ser Leu Ala Tyr Gly Leu Arg
1               5                   10

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Gly Asp Ser Leu Ala Tyr Gly
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Gly Asp Ser Leu Ala Tyr Gly Leu Arg
1               5                   10

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Ser Leu Ala Tyr Gly Leu Arg
1               5

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Val Asp Thr Tyr Asp Gly Arg Gly Asp Ser Val Val Tyr Gly Leu
1               5                   10                  15

Arg Ser

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Ser Val Val Tyr Gly Leu Arg
1               5

<210> SEQ ID NO 168
<211> LENGTH: 6
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 168

Cys Gly Arg Gly Asp Ser
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Arg Gly Asp Ser
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Asp Val Pro Asn Gly Arg Gly Asp Ser
1               5                   10

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Pro Asn Gly Arg Gly Asp
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Val Val Tyr Gly Leu Arg
1               5

<210> SEQ ID NO 173
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Arg Gly Asp Ser Leu Ala Tyr Gly Leu Arg
1               5                   10
```

```
<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Asp Ser Leu Ala Tyr Gly
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Asp Ser Leu Ala Tyr Gly Leu Arg
1               5

<210> SEQ ID NO 176
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Val Asp Val Pro Asn Gly Arg Gly Asp Ser Leu Ala Tyr Gly Leu Arg
1               5                   10                  15

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Leu Pro Val Lys Thr Asp Ser Gly Ser Ser Glu Glu Lys Leu Tyr
1               5                   10                  15

<210> SEQ ID NO 178
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Val Asp Thr Tyr Asp Gly Arg Gly Asp Ser Val Val Tyr Gly Leu Arg
1               5                   10                  15

Ser

<210> SEQ ID NO 179
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 179

Val Lys Leu Gln Glu Ser Gly Gly Leu Val Gln Pro Gly Gly Ser
1               5                   10                  15

Leu Ser Leu Ser Cys Ala Ala Ser Gly Phe Thr Phe Thr Asp Tyr Tyr
            20                  25                  30

Met Ile Trp Val Arg Gln Pro Pro Gly Lys Ala Leu Glu Trp Leu Gly
        35                  40                  45

Phe Ile Arg Asn Lys Ala Asn Gly Tyr Thr Thr Glu Tyr Ser Ala Ser
    50                  55                  60

Val Lys Gly Arg Phe Thr Ile Ser Arg Asp Asn Ser Gln Ser Ile Leu
65                  70                  75                  80

Tyr Leu Gln Met Asn Ala Leu Arg Ala Glu Asp Ser Ala Thr Tyr Tyr
                85                  90                  95

Cys Ala Phe Gly Ala Tyr Trp Gly Gln Gly Thr Thr Val Thr Val Ser
            100                 105                 110

Ser

<210> SEQ ID NO 180
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Val Lys Leu Gln Glu Ser Gly Thr Glu Leu Val Lys Pro Gly Ala Ser
1               5                   10                  15

Val Lys Leu Ser Cys Lys Ala Ser Gly Tyr Thr Phe Thr Asn Tyr Trp
            20                  25                  30

Met His Trp Val Lys Gln Arg Pro Gly Gln Gly Leu Glu Trp Ile Gly
        35                  40                  45

Asn Ile Asn Pro Arg Asn Gly Asp Ser Asn Tyr Asn Glu Lys Phe Arg
    50                  55                  60

Ser Lys Ala Ser Leu Thr Val Asp Lys Ser Ser Ser Thr Val Tyr Met
65                  70                  75                  80

Gln Leu Ser Ser Leu Thr Ser Glu Asp Ser Ala Val Tyr Tyr Cys Ala
                85                  90                  95

Phe Gly Tyr Phe Asp Val Trp Gly Gln Gly Thr Thr Val Thr Val Ser
            100                 105                 110

Ser

<210> SEQ ID NO 181
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45
```

```
Pro Lys Leu Leu Ile Tyr Arg Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Phe Val Pro Trp Thr Phe Gly Gly Gly Thr Lys Leu Glu Ile Lys
            100                 105                 110

Arg
```

<210> SEQ ID NO 182
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

```
Asp Ile Gln Met Thr Gln Ser Pro Ser Ser Met Tyr Ala Ser Leu Gly
 1               5                  10                  15

Glu Arg Val Ser Ile Thr Cys Lys Ala Ser Gln Asp Ile Asn Ser Tyr
             20                  25                  30

Leu Ser Trp Phe Gln Gln Lys Ser Gly Lys Ser Pro Lys Thr Leu Ile
         35                  40                  45

Tyr Arg Ala Asn Arg Leu Val Asp Gly Val Pro Ser Arg Phe Ser Gly
     50                  55                  60

Ser Gly Ser Gly Gln Asp Phe Ser Leu Thr Ile Ser Ser Leu Glu Tyr
 65                  70                  75                  80

Glu Asp Met Gly Ile Tyr Tyr Cys Leu Gln Tyr Asp Glu Phe Pro Phe
                 85                  90                  95

Thr Phe Gly Ser Gly Thr Lys Leu Glu Ile Lys Arg
            100                 105
```

<210> SEQ ID NO 183
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(399)

<400> SEQUENCE: 183

```
atg aag ttg tgg ctg aac tgg att ttc ctt gta aca ctt tta aat ggt      48
Met Lys Leu Trp Leu Asn Trp Ile Phe Leu Val Thr Leu Leu Asn Gly
 1               5                  10                  15 ttc cag tgt gag gtg aag ctg gtg gag tct gga gga ggc ttg gta cag     96
Phe Gln Cys Glu Val Lys Leu Val Glu Ser Gly Gly Gly Leu Val Gln
             20                  25                  30 cct ggg ggt tct ctg agt ctc tcc tgt gca gct tct gga ttc acc ttc    144
Pro Gly Gly Ser Leu Ser Leu Ser Cys Ala Ala Ser Gly Phe Thr Phe
         35                  40                  45 act gat tac tac atg atc tgg gtc cgc cag cct cca ggg aag gca ctt    192
Thr Asp Tyr Tyr Met Ile Trp Val Arg Gln Pro Pro Gly Lys Ala Leu
     50                  55                  60 gag tgg ttg ggt ttt att aga aac aaa gct aat ggt tac aca aca gag    240
Glu Trp Leu Gly Phe Ile Arg Asn Lys Ala Asn Gly Tyr Thr Thr Glu
 65                  70                  75                  80
```

-continued

```
tac agt gca tct gtg aag ggt cgg ttc acc atc tcc aga gat aat tcc    288
Tyr Ser Ala Ser Val Lys Gly Arg Phe Thr Ile Ser Arg Asp Asn Ser
                85                  90                  95 caa agc atc ctc tat ctt caa atg aat gcc ctg aga gct gag gac agt    336
Gln Ser Ile Leu Tyr Leu Gln Met Asn Ala Leu Arg Ala Glu Asp Ser
            100                 105                 110 gcc act tat tac tgt gca agg ggg gct tac tgg ggc caa ggg act ctg    384
Ala Thr Tyr Tyr Cys Ala Arg Gly Ala Tyr Trp Gly Gln Gly Thr Leu
        115                 120                 125 gtc act gtc tct gca                                                399
Val Thr Val Ser Ala
    130

<210> SEQ ID NO 184
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(393)

<400> SEQUENCE: 184 atg aag ttg cct gtt agg ctg ttg gtg ctg atg ttc tgg att cct gct    48
Met Lys Leu Pro Val Arg Leu Leu Val Leu Met Phe Trp Ile Pro Ala
1               5                   10                  15 tcc agc agt gat gtt ttg atg acc caa act cca ctc tcc ctg cct gtc    96
Ser Ser Ser Asp Val Leu Met Thr Gln Thr Pro Leu Ser Leu Pro Val
            20                  25                  30 agt ctt gga gat caa gcc tcc atc tct tgc aga tct agt cag agc att   144
Ser Leu Gly Asp Gln Ala Ser Ile Ser Cys Arg Ser Ser Gln Ser Ile
        35                  40                  45 gta cat agt aat gga aac acc tat tta gaa tgg tac ctg cag aaa cca   192
Val His Ser Asn Gly Asn Thr Tyr Leu Glu Trp Tyr Leu Gln Lys Pro
    50                  55                  60 ggc cag tct cca aag ctc ctg atc tac aga gtt tcc aac cga ttt tct   240
Gly Gln Ser Pro Lys Leu Leu Ile Tyr Arg Val Ser Asn Arg Phe Ser
65                  70                  75                  80 ggg gtc cca gac agg ttc agt ggc agt gga tca ggg aca gat ttc aca   288
Gly Val Pro Asp Arg Phe Ser Gly Ser Gly Ser Gly Thr Asp Phe Thr
                85                  90                  95 ctc aag atc agc aga gtg gag gct gag gat ctg gga gtt tat tac tgc   336
Leu Lys Ile Ser Arg Val Glu Ala Glu Asp Leu Gly Val Tyr Tyr Cys
            100                 105                 110 ttt caa ggt tca ttt gtt ccg tgg acg ttc ggt gga ggc acc aag ctg   384
Phe Gln Gly Ser Phe Val Pro Trp Thr Phe Gly Gly Gly Thr Lys Leu
        115                 120                 125 gaa atc aaa                                                       393
Glu Ile Lys
    130

<210> SEQ ID NO 185
<211> LENGTH: 87
<212> TYPE: PRT
<213> ORGANISM: Homo sapiens

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30
```

```
Arg Gln Ala Pro Gly Lys Gly Leu Glu Trp Val Gly Arg Phe Thr Ile
         35                  40                  45

Ser Arg Asp Asn Ala Lys Asn Ser Leu Tyr Leu Gln Met Asn Ser Leu
 50                      55                  60

Arg Ala Glu Asp Thr Ala Val Tyr Tyr Cys Ala Arg Trp Gly Gln Gly
 65                  70                  75                  80

Thr Met Val Thr Val Ser Ser
                 85

<210> SEQ ID NO 186
<211> LENGTH: 80
<212> TYPE: PRT
<213> ORGANISM: Homo sapiens

<400> SEQUENCE: 186

Asp Ile Val Met Thr Gln Ser Pro Leu Ser Leu Pro Val Thr Pro Gly
 1               5                  10                  15

Glu Pro Ala Ser Ile Ser Cys Trp Tyr Leu Gln Lys Pro Gly Gln Ser
             20                  25                  30

Pro Gln Leu Leu Ile Tyr Gly Val Pro Asp Arg Phe Ser Gly Ser Gly
         35                  40                  45

Ser Gly Thr Asp Phe Thr Leu Lys Ile Ser Arg Val Glu Ala Glu Asp
 50                      55                  60

Val Gly Val Tyr Tyr Cys Phe Gln Gly Thr Lys Val Glu Ile Lys
 65                  70                  75                  80

<210> SEQ ID NO 187
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Met Lys Leu Trp Leu Asn Trp Ile Phe Leu Val Thr Leu Leu Asn Gly
 1               5                  10                  15

Phe Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Phe Thr Phe
         35                  40                  45

Thr Asp Tyr Tyr Met Ile Trp Val Arg Gln Ala Pro Gly Lys Gly Leu
 50                      55                  60

Glu Trp Leu Gly Phe Ile Arg Asn Lys Ala Asn Gly Tyr Thr Thr Glu
 65                  70                  75                  80

Tyr Ser Ala Ser Val Lys Gly Arg Phe Thr Ile Ser Arg Asp Asn Ala
                 85                  90                  95

Lys Asn Ser Leu Tyr Leu Gln Met Asn Ser Leu Arg Ala Glu Asp Thr
             100                 105                 110

Ala Val Tyr Tyr Cys Ala Arg Gly Ala Tyr Trp Gly Gln Gly Thr Met
         115                 120                 125

Val Thr Val Ser Ser
         130

<210> SEQ ID NO 188
<211> LENGTH: 132
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 188

Met Arg Thr Pro Ala Gln Phe Leu Gly Ile Leu Leu Leu Trp Phe Pro
1               5                   10                  15

Gly Ile Lys Cys Asp Ile Val Met Thr Gln Ser Pro Leu Ser Leu Pro
            20                  25                  30

Val Thr Pro Gly Glu Pro Ala Ser Ile Ser Cys Arg Ser Ser Gln Ser
        35                  40                  45

Ile Val His Ser Asn Gly Asn Thr Tyr Leu Glu Trp Tyr Leu Gln Lys
    50                  55                  60

Pro Gly Gln Ser Pro Gln Leu Leu Ile Tyr Arg Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Phe Gln Gly Ser Phe Val Pro Trp Thr Phe Gly Gln Gly Thr Lys
        115                 120                 125

Val Glu Ile Lys
    130

<210> SEQ ID NO 189
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(399)

<400> SEQUENCE: 189 atg gga tgg agc tgt atc atc ctc ttt ttg gta gca gca gct aca ggt      48
Met Gly Trp Ser Cys Ile Ile Leu Phe Leu Val Ala Ala Ala Thr Gly
1               5                   10                  15 gtc cac tcc cag gtc caa ctg cag cag cct ggg act gaa ctg gtg aag      96
Val His Ser Gln Val Gln Leu Gln Gln Pro Gly Thr Glu Leu Val Lys
            20                  25                  30 cct ggg gct tca gtg aag ctg tcc tgt aag gct tct ggc tac acc ttc     144
Pro Gly Ala Ser Val Lys Leu Ser Cys Lys Ala Ser Gly Tyr Thr Phe
        35                  40                  45 acc aac tac tgg atg cac tgg gtg aag cag agg cct gga caa ggc ctt     192
Thr Asn Tyr Trp Met His Trp Val Lys Gln Arg Pro Gly Gln Gly Leu
    50                  55                  60 gag tgg att gga aat att aat cct aga aat ggt gat tct aac tac aat     240
Glu Trp Ile Gly Asn Ile Asn Pro Arg Asn Gly Asp Ser Asn Tyr Asn
65                  70                  75                  80 gag aag ttc agg agc aag gcc tca ctg act gta gac aaa tcc tcc agc     288
Glu Lys Phe Arg Ser Lys Ala Ser Leu Thr Val Asp Lys Ser Ser Ser
                85                  90                  95 aca gtc tac atg cag ctc agt agc ctg aca tct gag gac tct gcg gtc     336
Thr Val Tyr Met Gln Leu Ser Ser Leu Thr Ser Glu Asp Ser Ala Val
            100                 105                 110

```
tat tat tgt gca aga ggg tac ttc gat gtc tgg ggc aca ggg acc acg     384
Tyr Tyr Cys Ala Arg Gly Tyr Phe Asp Val Trp Gly Thr Gly Thr Thr
            115                 120                 125 gtc acc gtc tcc tca                                                 399
Val Thr Val Ser Ser
    130
```

<210> SEQ ID NO 190
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(381)

<400> SEQUENCE: 190

```
atg agg acc cct gct cag ttt ctt gga atc ttg ttg ctc tgg ttt cca      48
Met Arg Thr Pro Ala Gln Phe Leu Gly Ile Leu Leu Leu Trp Phe Pro
1               5                   10                  15 ggt atc aaa tgt gac atc aag atg acc cag tct cca tct tcc atg tat      96
Gly Ile Lys Cys Asp Ile Lys Met Thr Gln Ser Pro Ser Ser Met Tyr
            20                  25                  30 gca tct cta gga gag aga gtc tct atc act tgc aag gcg agt cag gac     144
Ala Ser Leu Gly Glu Arg Val Ser Ile Thr Cys Lys Ala Ser Gln Asp
        35                  40                  45 att aat agc tat tta agc tgg ttc cag cag aaa tca ggg aaa tct cct     192
Ile Asn Ser Tyr Leu Ser Trp Phe Gln Gln Lys Ser Gly Lys Ser Pro
    50                  55                  60 aag acc ctg atc tat cgt gca aac aga ttg gta gat ggg gtc cca tca     240
Lys Thr Leu Ile Tyr Arg Ala Asn Arg Leu Val Asp Gly Val Pro Ser
65                  70                  75                  80 agg ttc agt ggc agt gga tct ggg caa gat ttt tct ctc acc atc agc     288
Arg Phe Ser Gly Ser Gly Ser Gly Gln Asp Phe Ser Leu Thr Ile Ser
                85                  90                  95 agc ctg gag tat gaa gac atg gga att tat tat tgt cta cag tat gat     336
Ser Leu Glu Tyr Glu Asp Met Gly Ile Tyr Tyr Cys Leu Gln Tyr Asp
            100                 105                 110 gag ttt cca ttc acg ttc ggc tcg ggg aca aag ttg gaa ata aaa         381
Glu Phe Pro Phe Thr Phe Gly Ser Gly Thr Lys Leu Glu Ile Lys
        115                 120                 125
```

<210> SEQ ID NO 191
<211> LENGTH: 87
<212> TYPE: PRT
<213> ORGANISM: Homo sapiens

<400> SEQUENCE: 191

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Met
        35                  40                  45

Thr Arg Asp Thr Ser Thr Ser Thr Val Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Thr Val Thr Val Ser Ser
                85
```

```
<210> SEQ ID NO 192
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Phe Thr Leu Thr Ile Ser Ser Leu Gln Pro
65                  70                  75                  80

Glu Asp Phe Ala Thr Tyr Tyr Cys Leu Gln Tyr Asp Glu Phe Pro Phe
                85                  90                  95

Thr Phe Gly Gln Gly Thr Lys Leu Glu Ile Lys
            100                 105

<210> SEQ ID NO 193
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Trp Phe Gln Gln Lys Pro Gly Lys Ala
            20                  25                  30

Pro Lys Ser Leu Ile Tyr Gly Val Pro Ser Lys Phe Ser Gly Ser Gly
        35                  40                  45

Ser Gly Thr Asp Phe Thr Leu Thr Ile Ser Ser Leu Gln Pro Glu Asp
    50                  55                  60

Phe Ala Thr Tyr Tyr Cys Phe Gly Gln Gly Thr Lys Leu Glu Ile Lys
65                  70                  75                  80

<210> SEQ ID NO 194
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Met Lys Leu Trp Leu Asn Trp Ile Phe Leu Val Thr Leu Leu Asn Gly
1               5                   10                  15

Phe Gln Cys Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Gly Leu
    50                  55                  60
```

```
Glu Trp Ile Gly Asn Ile Asn Pro Arg Asn Gly Asp Ser Asn Tyr Asn
 65                  70                  75                  80

Glu Lys Phe Arg Ser Lys Ala Ser Leu Thr Val Asp Lys Ser Thr Ser
                 85                  90                  95

Thr Val Tyr Met Glu Leu Ser Ser Leu Arg Ser Glu Asp Thr Ala Val
                100                 105                 110

Tyr Tyr Cys Ala Arg Gly Tyr Phe Asp Val Trp Gly Gln Gly Thr Thr
            115                 120                 125

Val Thr Val Ser Ser
            130

<210> SEQ ID NO 195
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Met Arg Thr Pro Ala Gln Phe Leu Gly Ile Leu Leu Leu Trp Phe Pro
  1               5                  10                  15

Gly Ile Lys Cys Asp Ile Gln Met Thr Gln Ser Pro Ser Ser Leu Ser
                 20                  25                  30

Ala Ser Val Gly Asp Arg Val Thr Ile Thr Cys Lys Ala Ser Gln Asp
             35                  40                  45

Ile Asn Ser Tyr Leu Ser Trp Phe Gln Gln Lys Pro Gly Lys Ala Pro
         50                  55                  60

Lys Thr Leu Ile Tyr Arg Ala Asn Arg Leu Val Asp Gly Val Pro Ser
 65                  70                  75                  80

Lys Phe Ser Gly Ser Gly Ser Gly Gln Asp Phe Thr Leu Thr Ile Ser
                 85                  90                  95

Ser Leu Gln Pro Glu Asp Phe Ala Thr Tyr Tyr Cys Leu Gln Tyr Asp
                100                 105                 110

Glu Phe Pro Phe Thr Phe Gly Gln Gly Thr Lys Leu Glu Ile Lys
            115                 120                 125
```